United States Patent [19]
Weiss

[11] 4,194,055
[45] Mar. 18, 1980

[54] 15,16-DIOXY PROSTENOIC ACIDS AND ESTERS

[75] Inventor: Martin J. Weiss, Oradell, N.J.

[73] Assignee: American Cyanamid Company, Stamford, Conn.

[21] Appl. No.: 893,781

[22] Filed: Apr. 5, 1978

Related U.S. Application Data

[63] Continuation-in-part of Ser. No. 767,864, Feb. 11, 1977, Pat. No. 4,111,959, which is a continuation of Ser. No. 663,603, Mar. 3, 1976, abandoned.

[51] Int. Cl.$^2$ .................................................. C07C 177/00
[52] U.S. Cl. ........................................ 562/503; 560/121
[58] Field of Search .......................... 560/121; 562/503

[56] References Cited

U.S. PATENT DOCUMENTS 4,064,350  12/1977  Collins et al. ...................... 560/121

FOREIGN PATENT DOCUMENTS 2601646  7/1976  Fed. Rep. of Germany ........... 560/121
50-70340  6/1975  Japan ..................................... 560/121

OTHER PUBLICATIONS

Bornatsch et al., Prostaglandins 14, 617 (1977).
Samuelsson et al., Advances's in Prostaglandin and Thromboxane Research.

*Primary Examiner*—Robert Gerstl
*Attorney, Agent, or Firm*—Norton S. Johnson

[57] ABSTRACT

This disclosure describes novel 15,16-dioxy prostenoic acids and esters useful as bronochodilators, anti-inflammatory agents, hypotensives and gastric acid secretion inhibitors.

7 Claims, No Drawings

15,16-DIOXY PROSTENOIC ACIDS AND ESTERS

DESCRIPTION OF THE INVENTION

This invention relates to 15,16-dioxy prostenoic acids and esters of the formula:

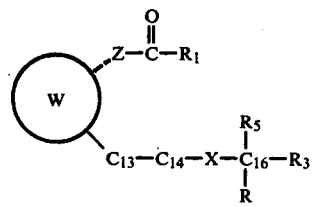

wherein W is selected from the group comprising

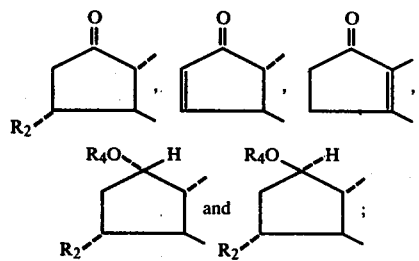

wherein R is selected from the group comprising hydroxy, lower alkoxy ($C_1$ to $C_3$), triloweralkylsilyloxy and alkanoyloxy groups ($C_2$ to $C_5$);

$R_1$ is selected from the group comprising hydroxy, tetrahydropyranyloxy, triloweralkylsilyloxy ($C_1$ to $C_4$) and straight or branched-chain alkoxy ($C_1$ to $C_{12}$);

$R_2$ is selected from the group comprising hydrogen, hydroxy, tetrahydropyranyloxy, triloweralkylsilyloxy ($C_1$ to $C_4$) and alkanoyloxy ($C_2$ to $C_5$);

$R_3$ is selected from the group comprising straight or branched-chain alkyl groups ($C_3$ to $C_6$) and straight or branched-chain alkenyl groups ($C_3$ to $C_6$);

$R_4$ is selected from the group comprising hydrogen, triloweralkylsilyl and alkanoyl ($C_2$ to $C_5$); $R_5$ is a hydrogen or lower alkyl group of from 1 to 3 carbon atoms; the moiety $C_{13}-C_{14}$ is ethylene or trans vinylene;

X is a divalent radical selected from the group comprising

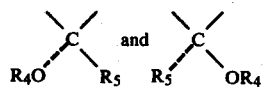

wherein $R_4$ and $R_5$ are as hereinabove described;

Z is a divalent radical selected from the group comprising —$(CH_2)_m$— (m=6-8),

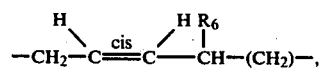

[wherein $R_6$ is hydrogen or lower alkyl ($C_1$ to $C_3$), and n is one of four], —$(CH_2)_Q$—O—$CH_2$—, —$(CH_2)_Q$—S—$CH_2$— (wherein Q=3 to 5),

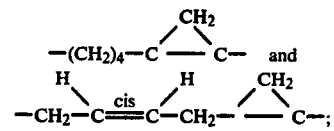

The divalent moiety

may be the divalent moiety

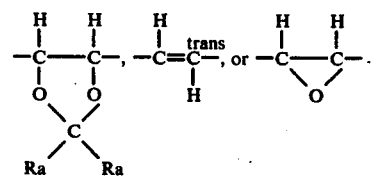

wherein Ra is a lower alkyl ($C_1$ to $C_3$) with the proviso that when

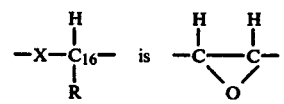

then Z does not embrace a double bond and $C_{13}-C_{14}$ is ethylene; and when $R_1$ is hydrogen the pharmaceutically acceptable salts thereof.

DETAILED DESCRIPTION OF THE INVENTION

Useful pharmacologically acceptable salts of the above formula wherein $R_1$ is hydrogen are those with pharmacologically acceptable metal cations, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are the methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di, and triethnolamine, ethyldiethanolamine, N-butylethanolamine, 2-amino-1-butanol, 2-amino-2-ethyl-1,3-propanediol, 2-amino-2-methyl-1-propanol, tris-(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds of this invention are administered in various ways for various purposes, e.g., intravenously, intramuscularly, subcutaneously, orally, intravaginally, rectally, bucally, sublinqually, topically and in the form of sterile implants for prolonged action, and as aerosol inhalants.

For intravenous injection or infusion, sterile aqueous isotonic solutions are preferred. For that purpose, it is preferred because of increased water solubility that $R_1$ be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixers, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain ocassions it may be advantageous to administer the compounds of this invention as clathrate compounds with substances such as β-cyclodextrin.

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstom et al., *J. Biol. Chem.*, 238, 3555 (1963) and Horton, *Experientia*, 21, 113 (1965) and references cited therein. All of the so called natural prostaglandins are derivatives of prostanoic acid:

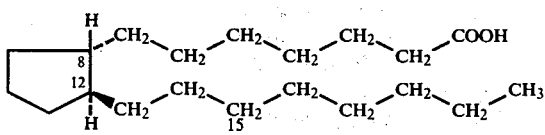

The hydrogen atoms attached to C-8 and C-12 are in trans-configuration. The natural prostaglandins represent only one of the possible optical isomers. The compounds of this invention include all possible optical isomers.

The $C_{15}$ position is a particularly important one and when it is substituted by a hydroxy or an alkanoyloxy group, and a hydrogen atom or lower alkyl group ($R_5$), it is assymetric, with the possibility of two configurations, deemed S or R. In partial formulae (A) below is shown the "natural" configuration of $C_8$, $C_{12}$, and $C_{15}$ as it is found in all known mammallian prostaglandins. The configuration at $C_8$ and $C_{12}$ is referred to as l and at $C_{15}$ as S; thus formula (A) is the l 15(S) or nat form. The enantiomer of (A) is represented by partial formula (B), the d 15(R) or ent form, and a substance deemed a dl-racemate without designation with regard to the situation at $C_{15}$ consists of enantiomers (A) and (B). Partial formula (C) represents a structure wherein the configuration at $C_8$ and $C_{12}$ is as in (A), the l form, but the configuration at $C_{15}$ is inverted to the R form. A structure embracing the configuration at $C_8$, $C_{12}$, and $C_{15}$ as shown in (C) is referred to as an l 15-epi derivative, the enantiomeric structure is represented by partial formula (D), the d 15-epi derivative, and (C) and (D) constitute a dl-15-epi racemate.

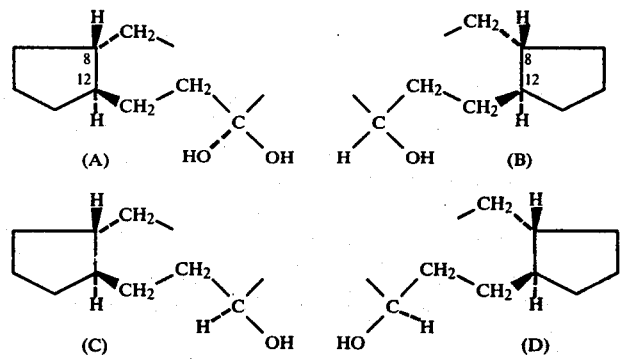

The compounds of this invention include all possible antipodes and particularly both possible configurations for $C_{15}$.

$C_{16}$ of the compounds of this invention is also an assymetric carbon atom and this invention embraces both the R and S configurations at $C_{16}$. When the oxy substituents at $C_{15}$ and $C_{16}$ are to each other as in (E) they are in the erythro configuration, and its mirror image; threo refers to a relationship as in (F) and its mirror image.

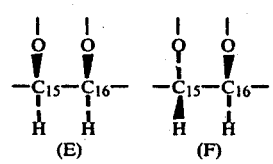

The novel compounds of this invention can be prepared by the reaction sequences illustrated in the following Flowsheets, wherein $R_3$, and Ra are as hereinbefore defined and Rc is a lower alkyl group of from 1 to 3 carbon atoms, inclusive.

The key reaction of these sequences is the conjugate 1,4-addition by an organometallo derivative of β-chain ($C_{13}$–$C_{20}$) to a 4-unsubstituted or 4-oxycyclopent-2-en-1-one substituted at the 2-position with the α-chain ($C_1$–$C_7$). The preparation of the β-chain required for this synthesis is described in Flowsheet A, which follows.
FLOWSHEET A
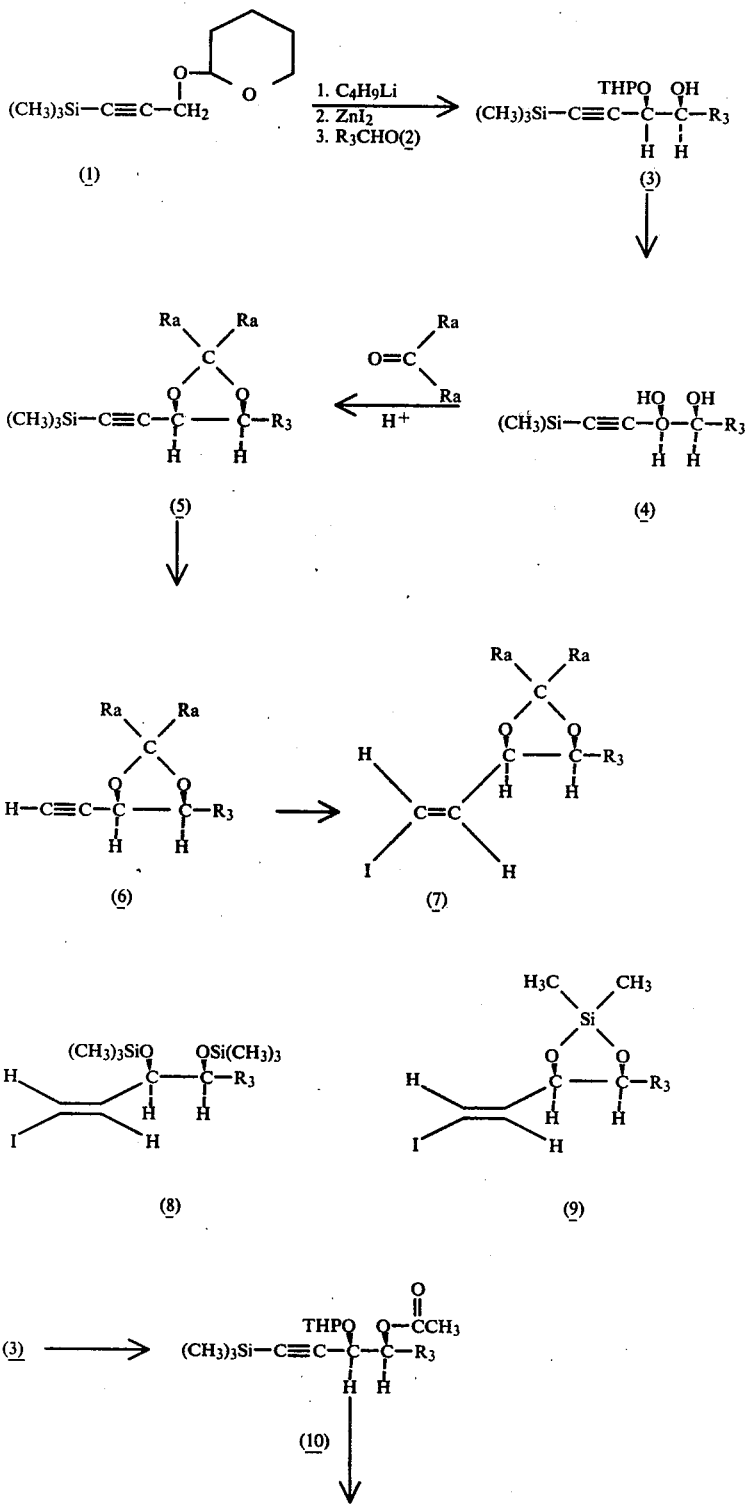

4,194,055
-continued
FLOWSHEET A
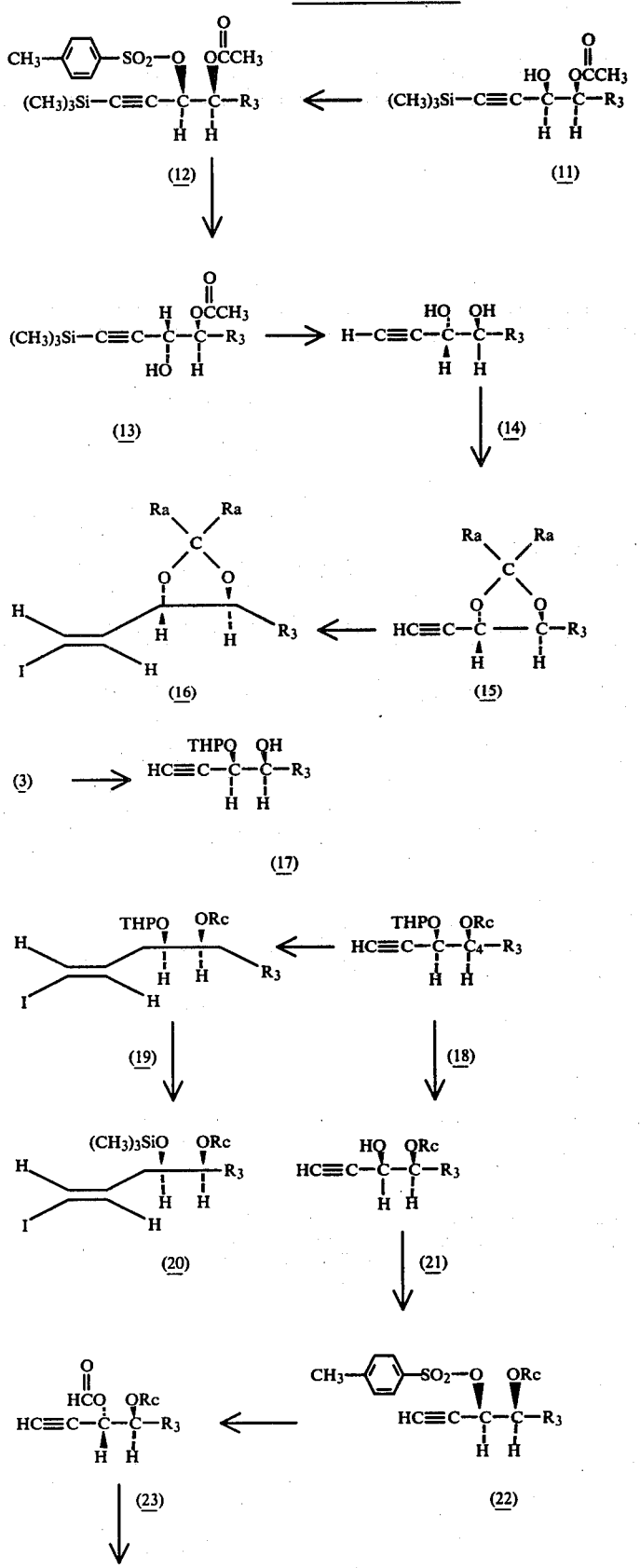

FLOWSHEET A

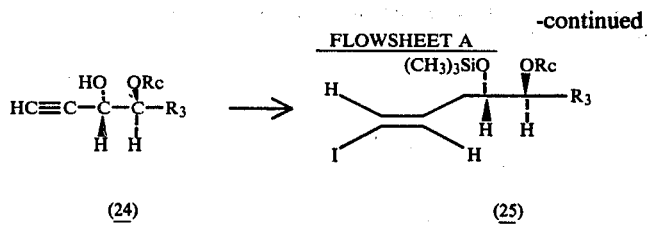

(24) (25)

In accordance with the scheme as outlined hereinabove in Flowsheet A, 1-trimethylsilyl-3-tetrahydropyranyloxy-1-propyne (1) is treated with n-butyllithium at −78° C. and then with a freshly prepared solution of zinc iodide in anhydrous tetrahydrofuran, also at −78° C. Reaction of aldehyde (2) with the resulting reagent then provides the 4-hydroxy-3-tetrahydropyranyloxy-1-alkyne (3). This reaction procedes with great stereoselectivity and the product (3) is in the erythro configuration. [For additional information concerning this reaction see the examples which follow and F. Mercier, R. Epsztein and S. Holland, *Bull. Soc. Chim. France*, 690 (1972).]

The tetrahydropyranyl group in (3) is removed on weak acid treatment and the resulting erythro diol (4) can be reblocked by treating with an appropriate aldehyde or ketone

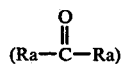

in the presence of strong acid catalyst in the usual way to give the ketal or acetal (5). Acetone is a useful ketone for this purpose and the product (5) is then a 3,4-isopropylidenedioxy-1-alkyne. It is also possible to utilize silyl blocking groups (introduced after removal of the 1-trimethylsilyl group) to ultimately give the vinyl iodides (8) or (9). Weak base treatment of (5), for example heating for about 1 hour in refluxing methanol with potassium carbonate, results in desilylation to give (6). The 1-alkyne (6) is converted to the corresponding 1-iodo-trans-1-alkene (7) by treatment with disiamylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give (7).

For the preparation of the threo derivatives, the 4-hydroxy-3-tetrahydropyranyloxy-1-alkyne (3) is acetylated to provide the corresponding 4-acetoxy derivative (10). The tetrahydropyranyl group is preferentially hydrolized with weak acid to (11), which is then tosylated in the usual manner to afford the erythro-3-tosyloxy-4-acetoxy-1-alkyne (12). Solvolysis of (12) under essentially neutral conditions by heating in aqueous tetrahydrofuran in the presence of an insoluble acid-acceptor, such as calcium carbonate, results in inversion of $C_3$, furnishing the threo-3-hydroxy-4-acetoxy-1-alkyne (13), which is then deblocked with aqueous base to give the threo-3,4-diol (14). Diol (14) is converted to an acetal or ketal (15) (or silyl derivatives as in 8 or 9) and thence to the 1-iodo-trans-1-alkene (16) as described hereinabove.

For the preparation of the 16-alkoxyprostanoic acids of this invention, the erythro-4-hydroxy-3-tetrahydropyranyloxy-1-alkyne (3) is desilylated by methanol-potassium carbonate treatment and the resulting (17) is etherified to give the 4-alkoxy-3-tetrahydropyranyloxy-1-alkyne (18). A useful procedure for this last step involves treatment of (17) with an molar equivalent of sodium hydride to give the 4-alkoxide which is then alkylated with the appropriate alkylating agent, for example methyl iodide. The 4-alkoxy-1-alkyne (18) is then converted to the corresponding 1-iodo-trans-1-alkene (19) as described hereinabove for the preparation of (7). If desired the tetrahydropyranyl blcoking group in (19) can be hydrolyzed (weak acid) and the resulting free 3-ol corresponding to (19) converted to the 3-trimethylsilyloxy derivative (20), all in the usual manner.

For the threo series, the tetrahydropyranyl group in erythro-4-alkoxy-1-alkyne (18) is cleaved and the resulting 3-hydroxy-4-alkoxy-1-alkyne (21) is tosylated to give the erythro 3-tosyloxy-4-alkoxy-1-alkyne (22). $Sn_2$ displacement reaction with (22) with reagents such as tetrahydroammonium formate results in inversion to the threo derivative (23), saponification of which provides threo-3-hydroxy-4-alkoxy-1-alkyne (24). Trimethylsilylation followed by the vinyl iodide conversion procedure described hereinabove furnishes the threo-1-iodo-1-alkene (25).

The 15-alkyl and/or 16-alkyl derivatives of this invention can be prepared by substituting

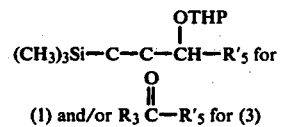

($R'_5=$ lower alkyl or 1 to 3 carbons) in Flowsheet A and carrying out the requisite subsequent transformations of Flowsheets A-D.

Conversion of the 1-iodo-trans-1-alkenes (7), (8), (9), (16), (19), (20), (25) or their equivalents of Flowsheet A (see 26 of Flowsheet B) to organometallo derivatives and their conjugate addition to appropriate cyclopentenones is illustrated in Flowsheet B, wherein M is a divalent radical of the group consisting of the following radicals in either the erythro or threo configuration:

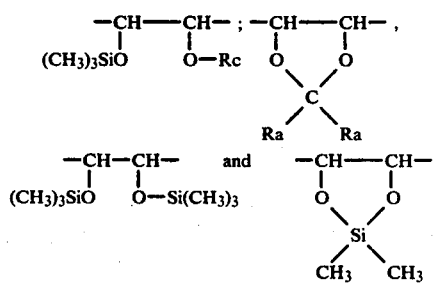

wherein Ra, and Rc are as hereinabove defined; M₁ is a divalent radical selected from the following divalent lower alkyl group of from 1 to 3 carbon atoms, inclusive.

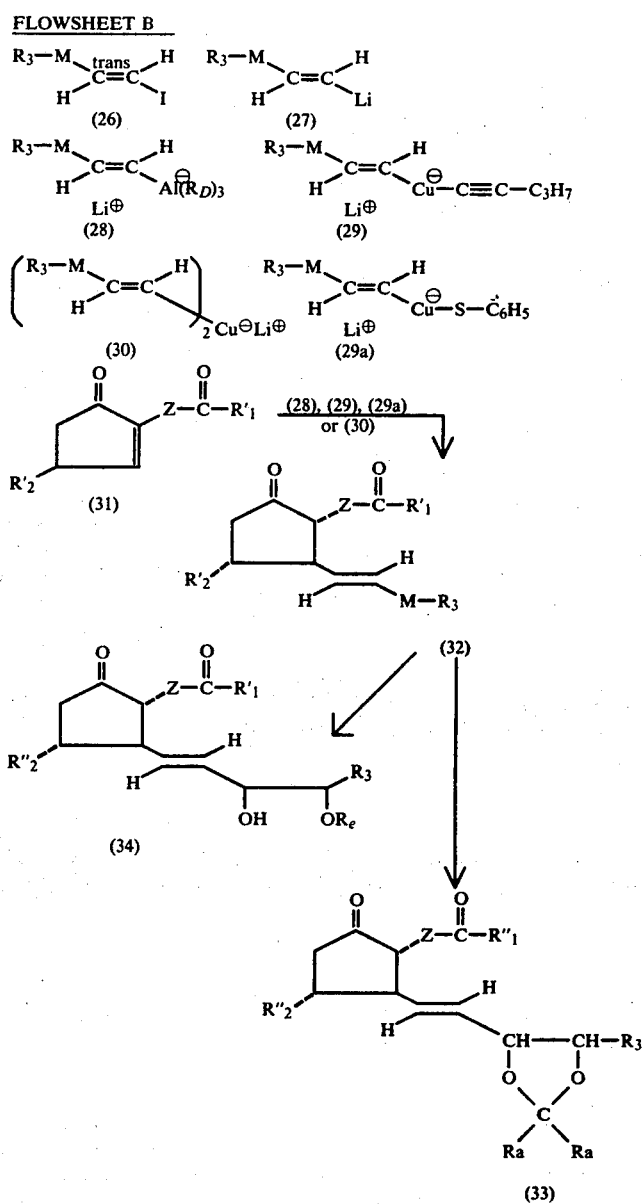

radicals in the erythro or threo configuration and wherein Ra, and Rc are as hereinabove defined:

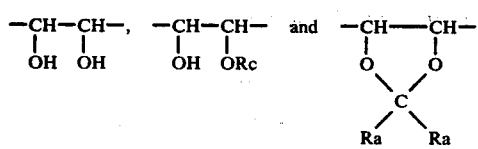

R'₁ has all possibilities of R₁ except for hydroxy, preferably it is lower alkoxy, tetrahydropyranyloxy or tri-lower alkylsilyloxy; R"₁ has all the possibilities of R₁ except for tetrahydropyranyloxy, or tri-loweralkyl-silyloxy; R'₂ is hydrogen or hydroxy; Ra is is an alkyl group of 1 to 5 carbon atoms, inclusive and it is not necessarily the same for each use; Re is hydrogen or a In accordance with the equations of Flowsheet B above, the 1-iodo-1-trans-1-alkene (26) is converted to the trans-vinyl lithium derivative (27) with clean retention of configuration by treatment at about −78° C. in hexane (isomeric mixture solution with either one equivalent of n-butyl lithium or two equivalents of t-butyl lithium. It is preferable for this treatment to proceed for about one hour at −78° C., then for about one hour at −40° C. and finally for about one hour at about 0° C. For the subsequent preparation of lithio alanate reagents (28) it is preferable to use n-butyl lithium, and for the lithio cuprate reagents (29), (29a) or (30) t-butyl lithium, is the agent of choice.

For the preparation of the alanate reagent (28) or the like, a molar equivalent of a tri-lower alkyl (1–5 carbon atoms) aluminum (e.g., trimethyl aluminum), dissolved in a solvent such as hexane, is added to the vinyl lithium derivative (27) at about 0° C. (It is preferable to avoid use of a tetrahydropyranyl blocking group in the alanate reagent). After about 15–45 minutes at this temperature the requisite blocked cyclopentenone (31) is added and the reaction mixture is stirred for about 18 hours at ambient temperatures. The mixture is quenched with aqueous dilute hydrochloric acid in the cold and the product is obtained by extraction. Trialkylsilyl blocking groups are removed on treatment with acetic acid:tetrahydrofuran:water (4:2:1) at room temperatures for about twenty minutes. Such treatment does not cleave the ketal/acetal or tetrahydropyranyloxy groups. Accordingly in order to obtain ketal/acetal structures such as 33, it is necessary that $R'_1$ be an ester or a trialkylsilyloxy group and that $R'_2$ be hydrogen or a trialkylsilyloxy group. The silyl, and or tetrahydropyranyl and acetal or ketal groups are removed by treatment with acetic acid:water:tetrahydrofuran (20:10:3) at about 40° C. for about 4 hours to give (34). Alkyl esters of the 11-oxy series are not disturbed by this treatment and cannot be saponified by chemical means in view of the instability of the 11-hydroxy-9-ketone to base treatment. However, the ester can be cleaved by treatment with Baker's Yeast, a procedure well-known in the art. However, the alkyl esters of the 11-deoxy series can be saponified in the usual manner. Base-treatment does not cleave the acetal or ketal groups.

For the preparation of the assymetric lithio cuprate (29) or the like, a solution of one molar equivalent of copper (I)-1-alkyne, preferably copper (I)-1-pentyne in anhydrous hexamethylphosphorous triamide, preferably three to five molar equivalents, and anhydrous ether is added to one molar equivalent of the aforementioned vinyl lithium (27) solution cooled to about $-78°$ C. After about one hour at this temperature, a molar equivalent of the requisiste cyclopentenone (31) is added. After several hours at about $-25°$ C. the reaction mixture is quenched with aqueous ammonium chloride solution and the blocked product (32) is isolated in the usual manner. The deblocking of this product is then carried out in the manner as described hereinabove. The phenylthio cuprate (29a) is prepared from lithio thiophenoxide (1 equiv.) and one equivalent of cuprous (I) iodide tri-n-butylphosphine complex, mixed in ether and added at $-78°$ C. to the alkenyl lithio derivative (27).

For the preparation of the symmetrical lithio cuprate (30) one molar equivalent of copper (I) iodide tributylphosphine complex dissolved in anhydrous ether is added at about $-78°$ C. to two molar equivalents of the aforementioned vinyl lithium (27) solution in hexanes, cooled to $-78°$ C. After about one hour at this temperature, the lithio cuprate (30) is treated with the requisite cyclopentenone (31) as described hereinabove for the conjugate addition with the 1-alkynyl lithio cuprate (29). For pertinent background information concerning various procedures for carrying out the conjugate addition reaction with lithio cuprate see C. J. Sih et al., Journ. Amer. Chem. Soc., 97, 857 865 (1975).

In order to ensure a trans-relationship in (32) (33) or (34), these products can be submitted to conditions known in the literature to equilibrate cis 8-iso-PGE$_1$ to a mixture containing about 90% of the trans-product [see E. G. Daniels et al., Journ. Amer. Chem. Soc., 90, 5894 (1968)]. These conditions involve treatment with potassium acetate in aqueous methanol for about 96 hours at room temperature. The cis and trans products are separable by chromatographic procedures.

Most of the cyclopentenones required for the purposes of this invention have been described in the literature or can be prepared by procedures quite analogous to those already described. Appropriate references are provided in the examples which follow. The synthesis of certain non-reference requisite cyclopentenones is also described therein.

As illustrated in Flowsheet C below, treatment of the 11-hydroxy derivatives represented by formula (34) in which $R''_2$ is hydroxy with dilute acid results in dehydration of the $\beta$-ketol system and the formation of the corresponding $\Delta^{10}$ derivatives (35) (prostaglandins of the A type). A preferred procedure involves treatment in tetrahydrofuran:water (2:1) solvent 0.5 N in hydrochloric acid for about twenty hours at ambient temperatures. More prolonged treatment with acid or preferably treatment with dilute base, e.g., sodium carbonate in aqueous methanol or an amine such as piperidine, effects the conversion of (34) or (35) or (33) to the $\Delta^{8(12)}$ derivatives (36) or (37) (prostaglandins of the B type).

FLOWSHEET C

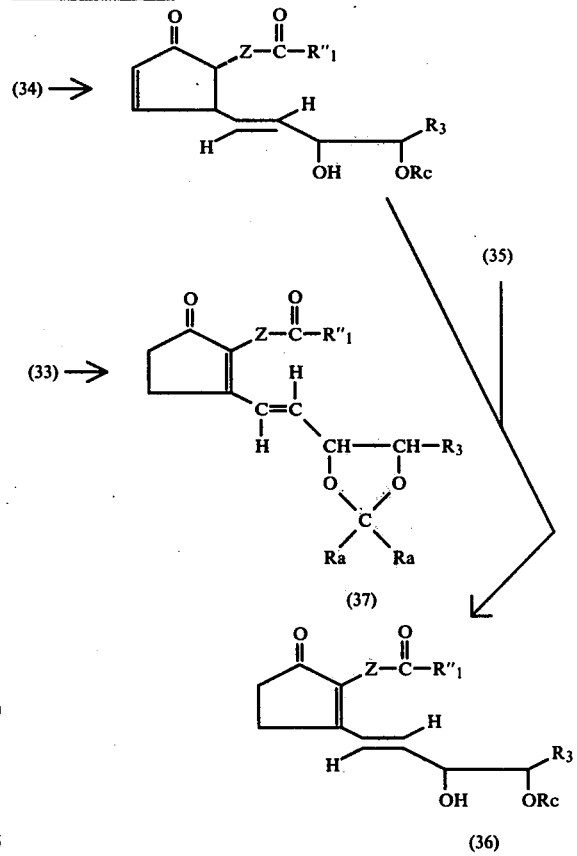

As illustrated in Flowsheet D below the 9-keto derivatives (38, see 33 and 34) of this invention can be converted to the corresponding 9-hydroxy derivatives. If this conversion is effected with sodium borohydride, the product is a mixture of 9$\alpha$- and 9$\beta$-hydroxy derivatives (prostaglandins of the F$\alpha$ and F$\beta$ series, respectively): (39) and (40), respectively. The 9$\alpha$ and 9$\beta$ derivatives are separable from each other by chromatographic procedures well-known in the art.

When the reduction is carried out with lithium perhydro-9b-boraphenylyl hydride [H. C. Brown and W. C. Dickason, Journ. Amer. Chem. Soc., 92, 709 (1970)] or with lithium tri(sec butyl)borohydride [H. C. Brown and S. Krishnamwrthy ibid. 94, 7159 (1972)], the product is at least predominantly the 9α-hydroxy derivative (39), wherein the 9-hydroxy group is cis to the sidechain attached to $C_8$ and to the 11-oxy function, if present. (In accordance with accepted convention, an α-substituent at the 8-, 9-, 11- or 12-positions is behind the place of the paper whereas a β-substituent at these positions is in front of the plane of the paper. This is usually represented by a —bond for an α-substituent, a —bond for a β-substituent, and a ⁓ bond where both possibilities are indicated.)

FLOWSHEET D

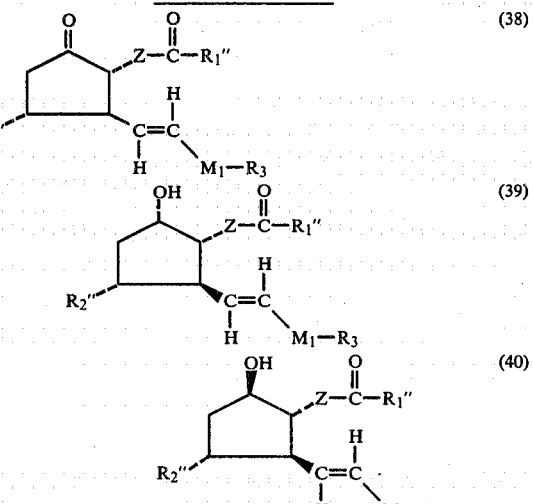

The 13-dihydro derivative ($C_{13}$–$C_{14}$ is ethylene) of this invention can be prepared by reduction of the $\Delta^{13}$ function in the corresponding 13-prostenoic acids or esters. This reduction can be accomplished by catalytic reduction, preferably at low pressure with a noble metal catalyst in an inert solvent at ambient temperatures.

The 13-dihydro derivatives can also be prepared by treating cycloalkenones of formula (31) with Grignard reagent (41) wherein $M_2$ is a divalent radical in the erythro or threo form selected from the group consisting of

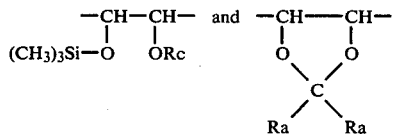

wherein Ra, and Rc are as hereinabove defined. This condensation is carried out in the usual manner in the presence of a catalyst such as the tributylphosphine cuprous iodide complex. The trimethylsilyl, ketal or acetal and other blocking groups are then removed in the usual manner as described hereinabove. [For an appropriate reference see R. E. Schaub, and M. J. Weiss, *Tetrahedron Letters*, 129 (1973)]. The use of (41) rather than catalytic reduction provides a cleaner procedure for the preparation of 13-dihydro derivatives embracing a double bond elsewhere in the molecule. For another procedure for the 13,14-dihydro derivatives see Flowsheet H, hereinbelow. Treatment of the 13-dihydro derivatives so obtained by the procedures of Flowsheets C and D, described hereinabove provide the 13,14-dihydro derivatives of the PGA, B, Fα and Fβ series.

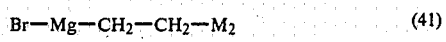

The Grignard procedure with tributylphosphine cuprous iodide complex as catalyst (preferably about 5 mole %) can also be used to prepare those compounds of this invention wherein $C_{13}$–$C_{14}$ is trans-vinylene. This procedure involves treating cyclopentenone (31) with Grignard reagent (42).

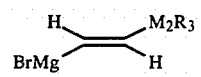

This reagent is prepared from the corresponding trans-vinyl bromide in the usual manner for the preparation of vinyl Grignard reagents in anhydrous tetrahydrofuran. The requisite 1-bromo-trans-1-alkenes (44) can be prepared by treatment of the corresponding trans-1-alkenyl lithio derivatives (43) (see 27, Flowsheet B hereinabove) with one molar equivalent of bromine.

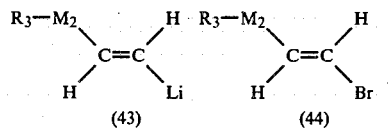

Conjugate addition of Grignard reagent (41) with cyclopentenones (31) gives (32, wherein M is limited to $M_2$. For pertinent literature examples see K. F. Bernady and M. J. Weiss, *Prostaglandins*, 3, 505 (1973).

The prostanoic and prostenoic carboxylic acids of this invention are convertible to the corresponding alkyl esters by treatment with the appropriate diazoalkane in the usual manner. The preparation of diazoalkanes by various procedures are well-described in the art, see for example C. D. Gutsche, *Organic Reactions*, VIII, 389 (1954). Certain of the esters of this invention can also be obtained by use of the appropriate cyclopentenone ester (31). The various esters can also be prepared by any of several procedures well-known in the art via an acid chloride (prior blocking of free alcohol groups with appropriate blocking groups such as trialkylsilyl, tetrahydropyranyl, ketals, acetals (see 33) and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydride is then treated with the appropriate alcohol to give the derivatized product.

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 5 minutes to one hour the product is worked-up in the usual manner. (For a pertinent literature analogy see U.S. Pat. No. 3,821,279, June 28, 1974).

The esterified alcohol derivatives ($R_2$ and/or R is alkanoyloxy and/or $R_4$ is alkanoyl) are also prepared in the usual manner by procedures well-known in the art from the appropriate alkanoic acid anhydride or acid chloride.

Certain of the novel 13,14-dihydro ($C_{13}$-$C_{14}$=ethylene) compounds of this invention can be prepared as described in Flowsheet H, which follows and in which $Z_1$ is a divalent radical selected from the group consisting of:

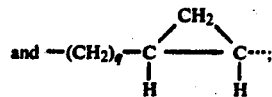

m, q, Ra, $R_3$, $R'_1$, $R''_2$, and $R''_2$ are as hereinabove defined.

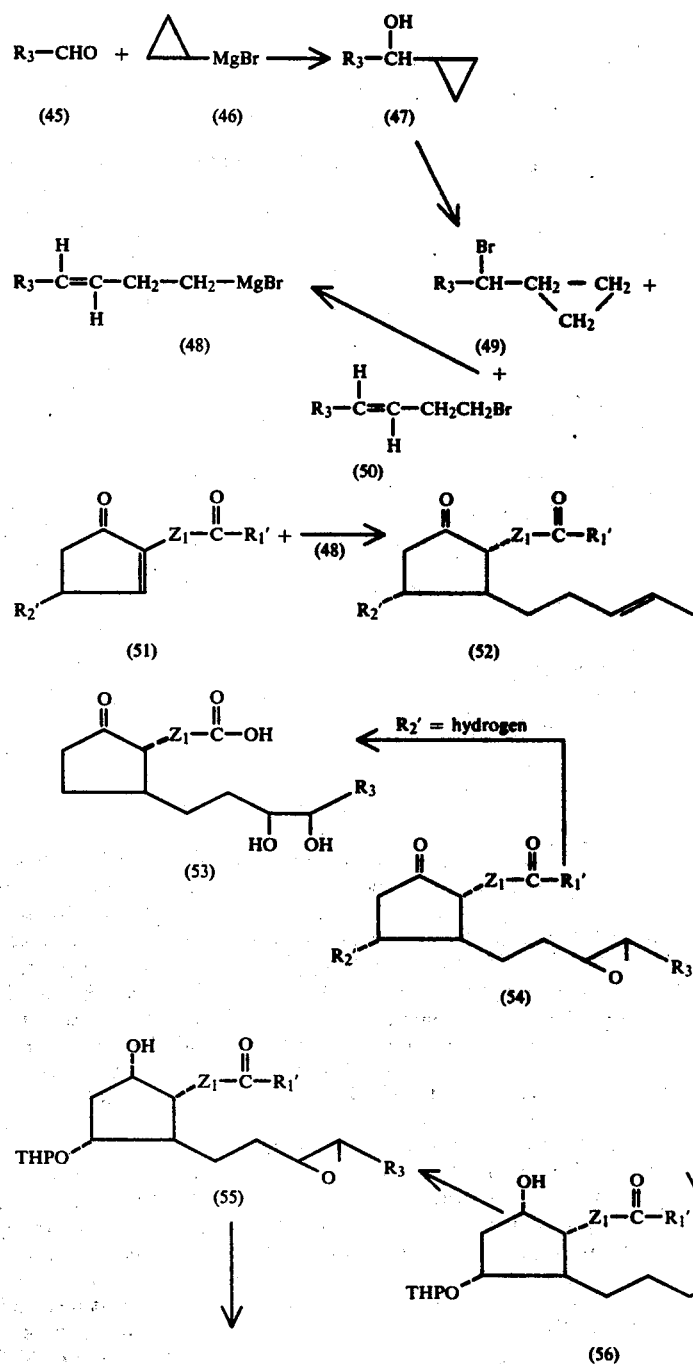

FLOWSHEET H

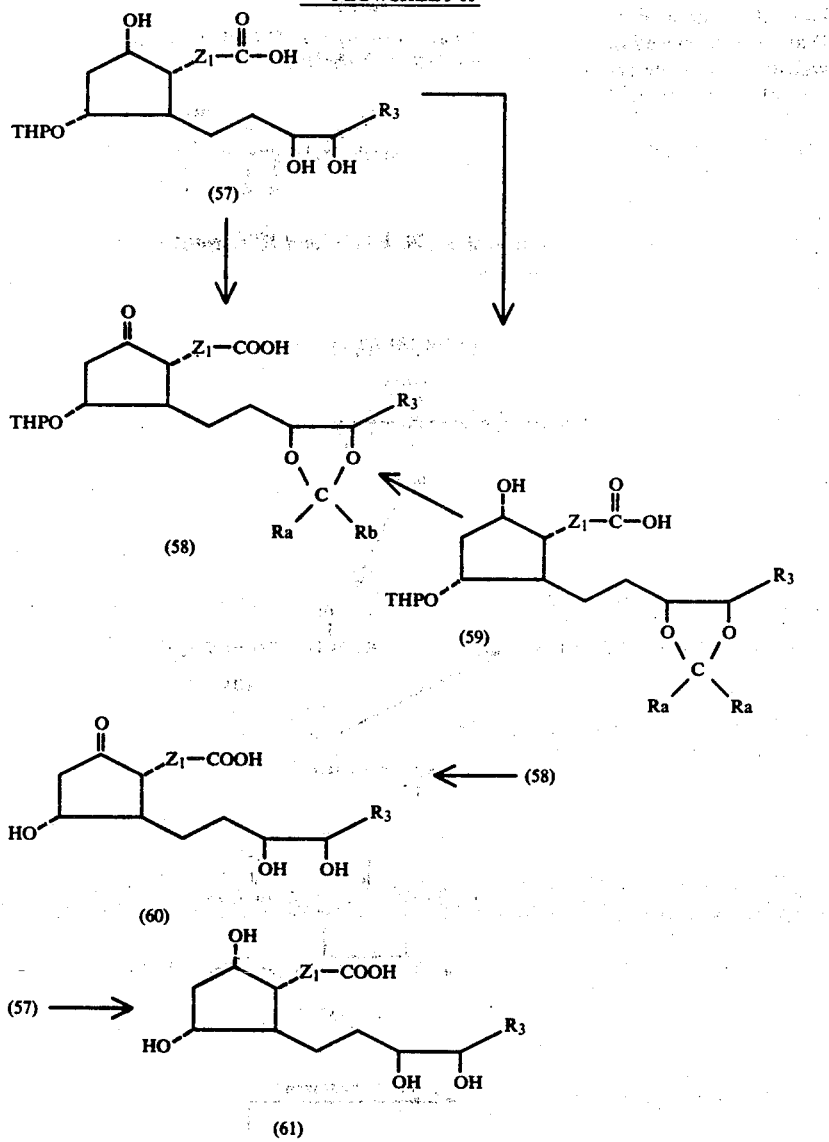

In accordance with the reaction sequences of Flowsheet H, hereinabove, aldehyde (45) is treated with cyclopropylmagnesium bromide (46) in the usual manner to give the cyclopropyl carbinol (47), treatment of which with 48% hydrobromic acid leads to a mixture of the bromides (49) and (50) [for a pertinent example, see M. Julia et al., *Bull. Soc. Chim. France*, 1961, 1849]. Treatment of the bromide mixture with magnesium in ether affords the linear 3-trans-octenylmagnesium bromide (48) exclusively [for a related reaction, see D. J. Patel et al., *J. Amer. Chem. Soc.*, 87, 5144 (1965)].

Reaction of this Grignard reagent with cyclopentenone (51) in the presence of tetrakis[iodo-(tri-n-butyl-phosphine)copper (I)] catalyst [G. B. Kaufman and L. A. Teter, *Inorg. Syn.* 7, 9 (1963)] affords the compound (52) containing the prostanoic acid skeleton. This conjugate addition reaction is carried out in an ether-type solvent at a temperature of $-20°$ C. to $25°$ C., preferably in diethyl ether at $0°$ C.

The trans-olefinic function in product (52) is converted to a trans-epoxide function using an organic peracid, preferably m-chloroperoxybenzoic acid, in an organic solvent such as chloroform or methylene chloride and optionally in the presence of a buffered aqueous phase, for example sodium bicarbonate. The trans-epoxide (54) is then isolated by conventional methods.

In the cases where $R'_2 = H$ and $R'_1 =$ lower alkyl, product (54) is directly submitted to treatment with alkali, for example with boiling aqueous sodium hydroxide, to effect saponification and opening of the epoxide ring in one operation. The 15,16-dihydroxy-prostanoic acid (53) contains the glycol moiety in the erythro configuration and is a mixture of two racemates.

In the cases where $R'_2$ is an oxy function, for example tetrahydropyranyloxy, and $R'_1$ is an acid-labile group, for example tetrahydropyranyloxy, product (52) is reduced with a hindered metal trialkylborohydride reagent in an ether solvent at low temperature to provide the 9α-hydroxy derivative (56). A satisfactory system for this reduction utilizes lithium (tri-sec-butyl)borohydride [H. C. Brown and S. Krishnamurthy, *Jour. Amer.*

Chem. Soc., 94, 7159 (1972)] in tetrahydrofuran at −78° C. Epoxidation of (56) as described above provides trans-epoxide (55). Removal of the ester group in (55) is effected at room temperature with dilute acetic acid for a few minutes; a suitable system for this conversion is 5:5:1 acetic acid-water-tetrahydrofuran. Alternatively, saponification and epoxide ring opening may be concurrently effected by hot alkali, for example boiling aqueous sodium hydroxide, to give 15,16-erythro-glycol acid (57).

The tetraol-11-monoether (57) is a useful intermediate for the preparation of prostanoic acids of both the E and Fα type. Conversion to the Fα derivatives requires only removal of the weak acid-labile ether function, for example with 4:2:1 acetic acid-tetrahydrofuran-water at 45° C. for several hours. The tetrahydroxyprostanoic acid (61) is then isolated and purified by standard methods.

For the preparation of the E derivatives (9-oxo function), the vicinal glycol function of (57) is protected by formation of a 1,3-dioxalane derivative (59). This conversion may be effected with an anhydrous solution of an enol ether, for example ethyl isopropenyl ether, in the presence of an acid catalyst. The remaining hydroxyl group at C-9 in (59) is oxidized by one of a variety of methods to give the 9-keto derivative (58). A preferred method for this oxidation involves treatment of (59) with chromic acid in acetone at −10° C. The protecting groups for the hydroxy groups at C-11, C-15, and C-16 are removed by treatment with acetic acid:water:tetrahydrofuran (20:10:3) at about 40° C. for about 4 hours to give (60).

Also embraced by the present invention are the intermediates expressed by the following generic formulae (62–67) which include both the threo and erythro configurations.

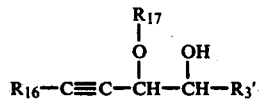
(62)

wherein $R_{16}$ is hydrogen or tri-lower alkylsilyl; $R_{17}$ is hydrogen or tetrahydropyranyl; and $R'_3$ is a straight or branched chain alkenyl group ($C_3$ to $C_6$);

(63)

wherein $R_3$ is hereinabove defined; J is selected from the group consisting of:

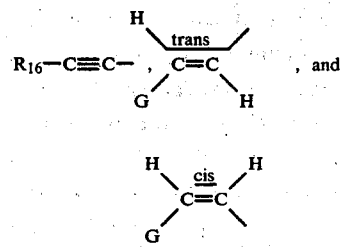

wherein $R_{16}$ is as hereinabove defined and G is a member of the group consisting of iodine, bromine, or lithium atoms and $W_4$ is a divalent radical selected from the group consisting of

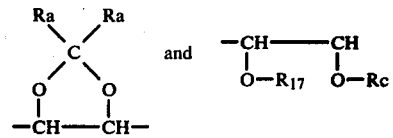

wherein Ra, and Rc are as hereinabove defined and $R_{17}$ is tetrahydropyranyl or trimethylsilyl;

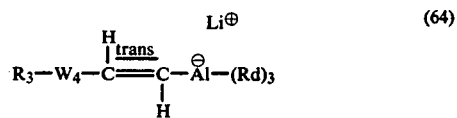
(64)

wherein $R_3$, $W_4$ and $R_d$ are as hereinabove defined;

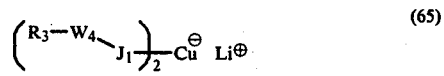
(65)

wherein $R_3$ and $W_4$ are as hereinabove defined and $J_1$, is cis- or trans-vinylene; and the complexes of (65) with trialkyl (3 to 7 carbon atoms, inclusive) phosphines and the like;

(66)

wherein $R_3$, $W_4$ and J are as hereinabove defined; $R_{18}$ is an alkyl group of from 2 to 5 carbon atoms, inclusive and the complexes of (66) with trialkyl (3 to 7 carbon atoms, inclusive phosphines or hexa-lower alkylphosphoramides and the like;

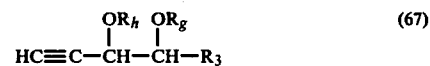
(67)

wherein $R_3$ is as hereinabove defined; Rg is lower alkyl of 1 to 3 carbon atoms, inclusive, lower alkenayl of from 2 to 4 carbon atoms, inclusive; and Rh is hydrogen, arylsulfonyl, lower alkyl sulfonyl, formyl or lower alkanoyl of from 2 to 4 carbon atoms, inclusive.

In Flowsheet B hereinabove, when the β-chain precursor (26) and the 4-oxycyclopentenone (31) are in the racemic form, then products (33) and (34) will be obtained as a mixture of two racemates. If either the 4-oxycyclopentenone (31, $R'_2$=oxy group) or the β-chain precursor (26) are in an optically active form two diastereomers result. With the 4-unsubstituted cyclopentenone (31, $R'_2$=hydrogen) either two racemates or two diastereomers are formed, depending upon whether the β-chain precursor (26) is optically active. Separation of racemic or diastereomeric (33) and (34) into the component 15-natural and 15-epi racemates or diastereomers in appropriate instances can be accomplished by careful application of the usual chromatographic procedures. In the more difficult instances it may be necessary to apply high pressure liquid chromatography including recycling techniques. [See G. Fallick, *American Laboratory*, 19–27 (August, 1973) as well as references cited therein. Additional information concerning high speed liquid chromatography and the instruments necessary for its application is available from Waters Associate, Inc., Maple St., Milford, Mass.]

The 4-hydroxycyclopentenone racemates may be resolved into their component enantiomers (73) and (74) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride (to give 75), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (73) and (74). A useful procedure for the resolution of a 4-hydroxycyclopentenone racemate via an oxime such as (75) is described in the art [R. Pappo, P. Collins and C. Jung, *Tetrahedron Letters*, 943 (1973)].

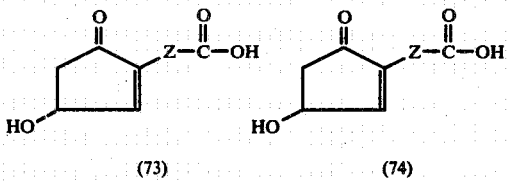

(73)            (74)

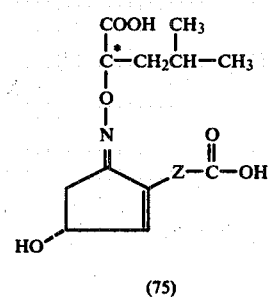

(75)

An alternative procedure for the preparation of the 4(R)-hydroxycyclopentenone enantiomers such as (73) involves as a key step the selective microbiological or chemical reduction of trione (76) to the 4(R)-hydroxycyclopentanedione (77). A wide variety of microorganisms are capable of accomplishing this asymmetric reduction, one of the most useful being *Dipodascus unincleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis(o-anisylcyclohexylmethylphosphine)rhodium (I) tetrafluoroborate in the presence of one equivalent of organic base, such as triethylamine.

Conversion of hydroxycyclopentanedione (77) to an enol ether or enol ester, (78, E=alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° to −15° C. Reduction of (78) with excess sodium bis(2-methoxyethoxy)aluminum hydride in a solvent such as tetrahydrofuran or toluene at low temperatures, such as −60° to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (79). The ester (79) after blocking the hydroxy function as described hereinabove, can be subjected to conjugate addition reactions also as described hereinabove. The conjugate addition product, after deblocking the 11- and 15-hydroxy groups, will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C. J. Sih et al., *Journ. Amer. Chem. Soc.*, 95 1676 (1973); 97, 865 (1975); J. B. Heather et al., *Tetrahedron Letters*, 2213 (1973); R. Pappo and P. W. Collins, *Tetrahedron Letters*, 2627 (1972) and R. Pappo, P. Collins and C. Jung, *Ann. N.Y. Acad. Sci.*, 180 64 (1971). For a descriptive of the baker's yeast procedure see C. J. Sih et al., *Journ. Amer. Chem. Soc.*, 94, 3643 (1972); 97, 857 (1975).

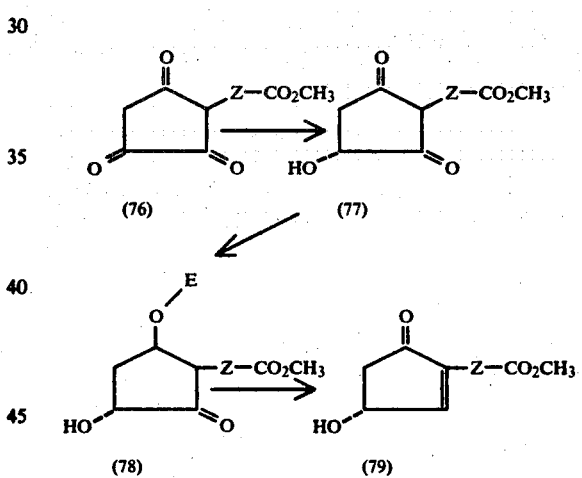

Procedures for the preparation of the requisite cyclopentanetriones (76) are well-established in the art and generally involve the treatment of an ω-1 oxo long chain ester (80) with methyl or ethyl oxalate and a base such as sodium methoxide in methanol, followed by treatment with dilute hydrochloric acid in aqueous methanol to effect the dealkoxalylation of the intermediate (81). See J. Kutsube and M. Matsui, *Agr. Biol. Chem.*, 33, 1078 (1969); P. Collins, C. J. Jung and R. Pappo, *Israel Journal of Chemistry*, 6, 839 (1968); R. Pappo, P. Collins and C. Jung, *Ann. N.Y. Acad. Sci.* 180, 64(1971); C. J. Sih et al., *Journ. Amer. Chem. Soc.*, 95, 1676 (1973) (see reference 7); 87, 865 (1975); and J. B. Heather et al., *Tetrahedron Letters*, 2313 (1973) for pertinent background literature.

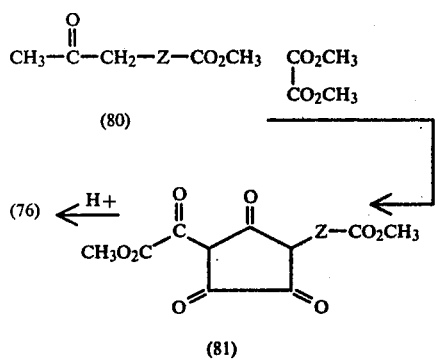

The intermediate keto esters (80) may be prepared by a variety of methods known to the art. One useful procedure is outlined below and invlves alkylation of ethyl acetoacetate sodium salt (82) in the usual manner with the appropriate side-chain precursor (83, X=Cl, Br, I, preferably Br or I) followed by decarbethoxylation and reesterification, all in the usual manner.

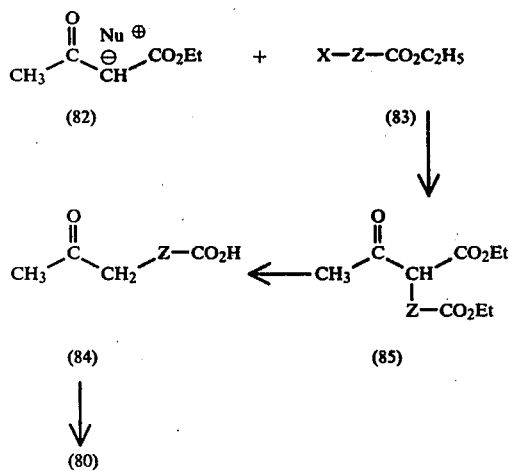

The side-chain precursors (83) are commercially available where Z is —(CH$_2$)$_m$—.

Those precursors wherein Z is —(CH$_2$)$_q$—O—CH$_2$— can be prepared by the transformation shown directly below starting with the mono-tetrahydropyranyl derivative (95), prepared from the corresponding diol. Thus, (95), is converted to the lithium alcoholate by treatment with butyl lithium, the alcoholate is then O-alkylated with ethyl bromoacetate to provide (96), which on de-O-tetrahydropyranylation, mesylation and reaction with lithium bromide gives the required (99). (These and all the above-described transformations can be effected in the usual manner, well-established in the art; pertinent examples for most of the reactions can be found in Belgian Pat. No. 786,215, granted and opened to inspection January 15, 1973.)

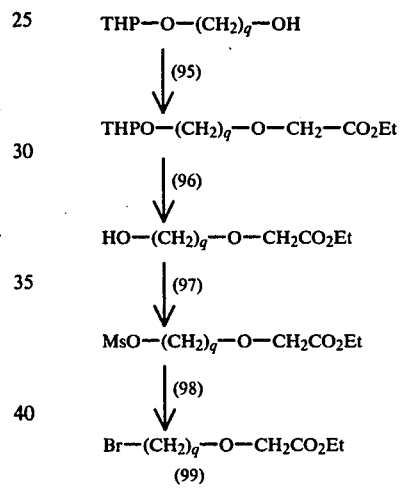

It is also possible to resolve the 4-hydroxycyclopentenone racemate (100) by microbiological means. Thus, treatment of the 4-O-alkanoyl or aroyl derivatives (101, R$_{18}$=aryl or alkyl) of racemate (100) preferably the 4-O-acetyl and 4-O-propionyl derivatives) with an appropriate microorganism, preferably a Saccharomyces species e.g., 1375-143, affords preferential de-O-acylation of the 4(R)-enantiomer to give (102), which is then separated from the unreacted 4(S)-O-acyl anantiomer (103) by chromatographic procedures. After separation, mild hydrolysis of the 4(S) derivatives (103) provides the 4(S)-hydroxycyclopentenone (104). [See N. J. Marscheck and M. Miyano, *Biochimica et Biophysica Acta*, 316, 363 (1973) for related examples.]

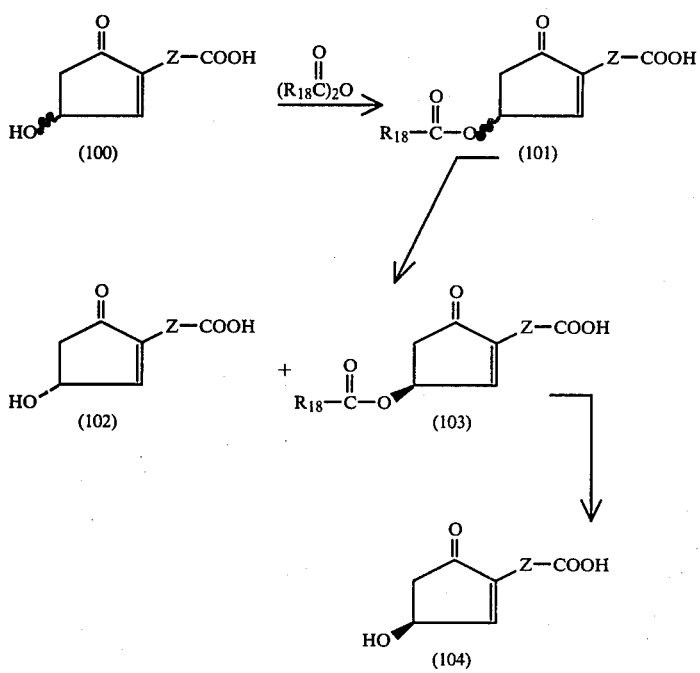

It is also possible to prepare the individual 4-hydroxycyclopentenones (73) and (74) directly by selective microbial hydroxylations of the corresponding 4-unsubstituted cyclopentenone (105). For example, with *Aspergillus niger* ATCC 9142; a selective 4(R)-hydroxylation of (105, $Z=(CH_2)_6$) has been reported; see S. Kurozumi, T. Tora and S. Ishimoto, *Tetrahedron Letters*, 4959 (1973). Other microorganisms can also accomplish this hydroxylation.

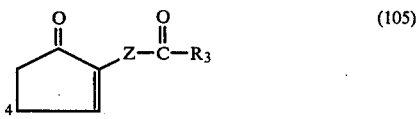

An alternate resolution procedure involves derivatization of the alcohol function of the racemic hydroxycyclopentenone to give ester-acid derivatives such as (106) wherein $R''_1$ is hydroxy or an alkoxy group, $n'$ is zero or two and Z is as hereinabove defined.

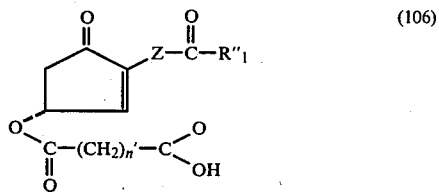

Such derivatives may be obtained from the corresponding free hydroxycyclopentenone by treatment in the usual manner with oxalyl chloride, succinyl chloride, succinic anhydride and the like. Treatment of the resulting acid or diacid (106, $R''_1$=hydroxy) with optically active amines e.g., 1-(−)-α-methylbenzylamine, d-(+)-α-methylbenzylamine, brucine, dehydroabietylamine, strychnine, quinine, cinchonine, qunidine, ephedrine, (+)-α-amino-1-butanol and the like, and fractional recrystallization of the resulting diastereomeric mixtures, followed by cleavage of the 4-oxy ester function in each of the individually isolated diastereomers provides the individual 4(R)- and 4(S)-hydroxycyclopentenone enantiomers (73) and (74) or their respective esters. Cleavage of the oxalate acid ester (106, $n'=0$) can be accomplished by treatment with lead tetraacetate in pyridine solution. For an example of a similar use of oxalate acid-esters see J. G. Molotkovsky and L. D. Bergelson, *Tetrahedron Letters*, 4791 (No. 50, 1971); for an example of the use of a succinate acid-ester see B. Goffinet, Ger. Offen. 2,263,880; *Chem. Abstracts*, 79, 78215z (1973).

Appropriate and useful intermediates for the resolution of the racemic β-chain precursors are illustrated in Flowsheet A hereinabove, for example the 1-trimethylsilyl-3-hydroxy-4-acyloxy-1-alkynes (11) and (13) and particularly the corresponding desilylated derivatives prepared via (17), the 3-hydroxy-4-alkoxy-1-alkynes (21) and (24), and the 1-iodo-3-hydroxy-4-alkoxy-trans-1-alkenes obtained on desylilation of (20) and (25). These compounds are all essentially either in the erythro or threo configurations.

The racemic β-chain precursors can be resolved at either the acetylenic alcohol stage or the trans-vinyl iodide state by a variety of methods well-known in the art. These methods will be illustrated below with the acetylenic alcohol (107) wherein $R_3$ is as hereinabove defined and B is a lower alkanoyloxy or lower alkoxy group, but they apply equally well to the trans-vinyl iodide (108). Furthermore, the resolved acetylenic alcohols corresponding to (107) can be converted to the trans-vinyl iodides corresponding to (108) or its derivatives as described hereinabove without rzation [see for an example, A. F. Kluge, K. G. Untch and J. H. Fried, *Journ. Amer. Chem. Soc.*, 94, 7827 (1972)].

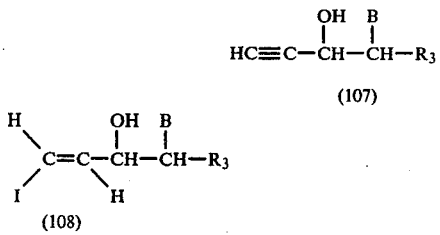

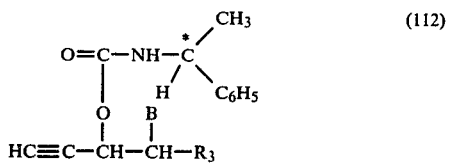

Racemates (107) and (108) can be resolved by reverse phase and absorption chromatography on an optically active support system or by selective transformation of one isomer by microbiological or enzymatic procedures.

A more generally applicable procedure involves conversion of the racemic alcohol to a mixture of diastereomers by derivatization of the hydroxy function with an optically active reagent, followed by separation of the diastereomers by fractional crystallization or chroamtographic procedures, as discussed hereinabove. Regeneration of the alcohol function from the individual diastereomer then provides the individual enantiomeric alcohols (109) and (110), shown in the erythro form, but the same applies to the threo derivatives.

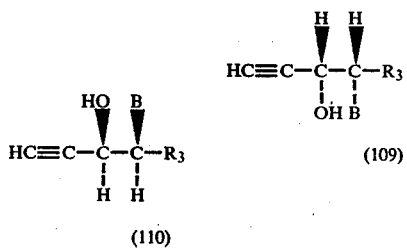

Useful derivatives for resolution purposes include the salts of the phthalate half acid ester (111) with an optically active amine (e.g., 1-(−)-α-methylbenzylamine, d-(+)-α-methylbenzylamine, brudine, dehydroabietylamine, strychnine, quinine, cinchonine, cinchonidine, quinidine, ephedrine, deoxyephedrine, amphetamine, (+)-2-amino-1-butanol, (−)-2-amino-1-butanol and the like).

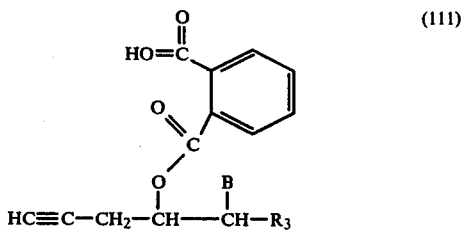

For the resolution in the art of the related 3-hydroxy-1-octyne by this procedure see J. Fried et al., *Annals of the N.Y. Acad. of Sci.*, 180, 38 (1971), and of the related 1-iodo-trans-1-octen-3-ol see A. F. Kluge, K. G. Untch and J. H. Fried, *Journ. Amer. Chem. Soc.*, 94, 7827 (1972).

Other useful derivatives are the diastereomeric carbamates (112) obtained by treatment of racemate (107) with an optically active isocyanate (e.g., (+)-1-phenylethylisocyanate and (−)-1-phenylethylisocyanate).

Various esters of racemate (107) with optically active acids are also useful for resolution purposes. Among the optically active acids which can be used in this connection are ω-camphoric acid, menthoxyacetic acid, 3α-acetoxy-Δ$^5$-etianic acid, 3α-acetoxy-5,16-etiadienoic acid, (−)-α-methoxy-α-trifluoromethylphenylacetic acid (see 113), (+)-α-methoxy-α-trifluoromethylphenylacetic acid, and the like.

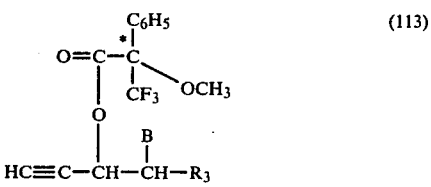

The resolution of the related 1-octyne-3-ol with 3β-acetoxy-Δ$^5$-etianic acid and 3β-acetoxy-5,16-etiadienoic acid has been described in the art [see R. Pappo, P. Collins, and C. Jung, *Annals of the N.Y. Acad. of Sci.*, 180, 64 (1971)].

The conjugate addition products such as (33) and (34) either in the erythro or threo configuration, after chromatographic separation into individual racemates can be resolved into individual component enantiomers by procedures well-known in the art, certain of which are illustrated below.

Resolution of a 9-hydroxy erythro racemate (the component enantiomers are illustrated by (114) and (115) below may be accomplished by conversion of the racemate wherein the $C_{11}$ (if present), $C_{15}$, and if present, $C_{16}$ hydroxy functions have been preferentially blocked by tetrahydropyranyl, trialkylsilyl or 15,16-acetal or ketal groups, for example, by first derivatizing the one, two or three hydroxy functions in the corresponding 9-oxo derivative and then reducing the 9-carbonyl as described hereinabove, conversion to the corresponding phthalate half acid-ester, deblocking the $C_{11}$ (if present) and $C_{15}$ and $C_{16}$ (if present) hydroxy functions and conversion of the diacids (e.g., 116) to a mixture of diastereomeric bis salts (e.g., 117) with an optically active amine (e.g., 1-(−)-α-methylbenzylamine, D-(+)-α-methylbenzylamine, brucine, dehydroabietylamine, strychnine, quinine, cinchonine, quinidine, ephedrine, deoxyepedrine, amphetamine, (+)-2-amino-1-butanol, (−)-2-amino-1-butanol and the like). The resulting diastereomers are separated by fractional crystallization and the individual components are then converted by acidification and saponification to the individual optically active parent 9α-hydroxy enantiomers (114) and (115), oxidation of which, after preferential biocking of the $C_{11}$, $C_{15}$ and if present $C_{16}$ hydroxy functions with tetrahydropyranyl or trialkylsilyl groups, provides after deblocking, the corresponding individual 9-oxo enantiomers (118) and (119). If necessary, the 11- and 15-hydroxy groups can be converted to tetrahydropyranyloxy groups or a 15,16-acetal or ketal can be formed prior to saponification of the phthalate ester. (For an appropriate literature procedure see E. W. Yankee, C. H. Lin and J. Fried, *Journ. Chem. Soc.*, 1972, 1120).

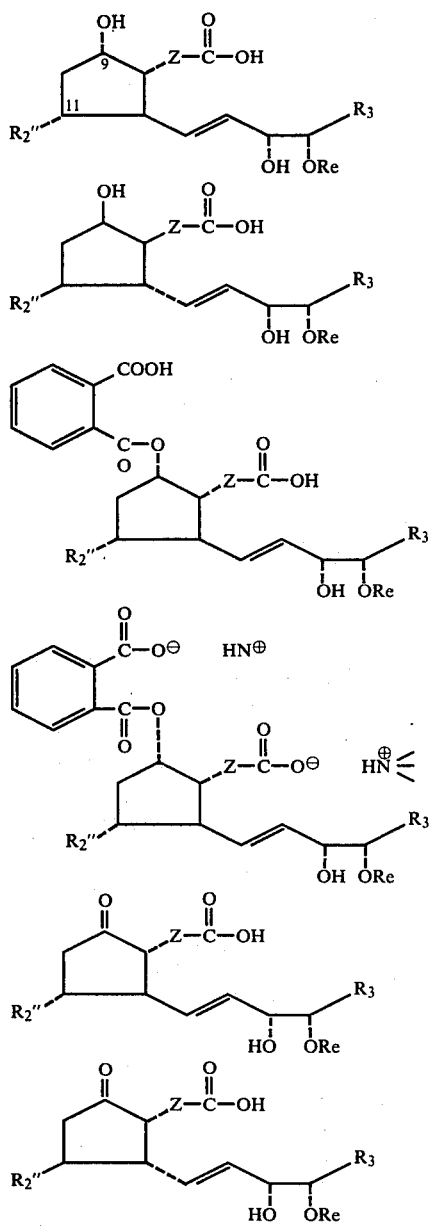

Another procedure involves conversion of the 9α-hydroxy racemate (as the prostenoic acid ester and with the $C_{11}$ and $C_{15}$ and $C_{16}$ alcohol functions preferentially blocked as tetrahydropyranyl or trialkylsilyl ethers or 15,16-acetals or ketals) to the diastereomeric carbamates with an optically active isocyanate, e.g., (+)-1-phenylethylisocyanate or (−)-1-phenylethylisocyanate, followed by deblocking. Separation of the resulting diastereomers, for example (121) and (120), can be accomplished by fractional crystallization or by the usual chromatographic procedures, or if necessary by high speed liquid chromatography involving, if necessary, recycling techniques. Base-treatment of the individual diastereomeric carbamates affords the individual diastereomeric alcohls, for example (114) and (115).

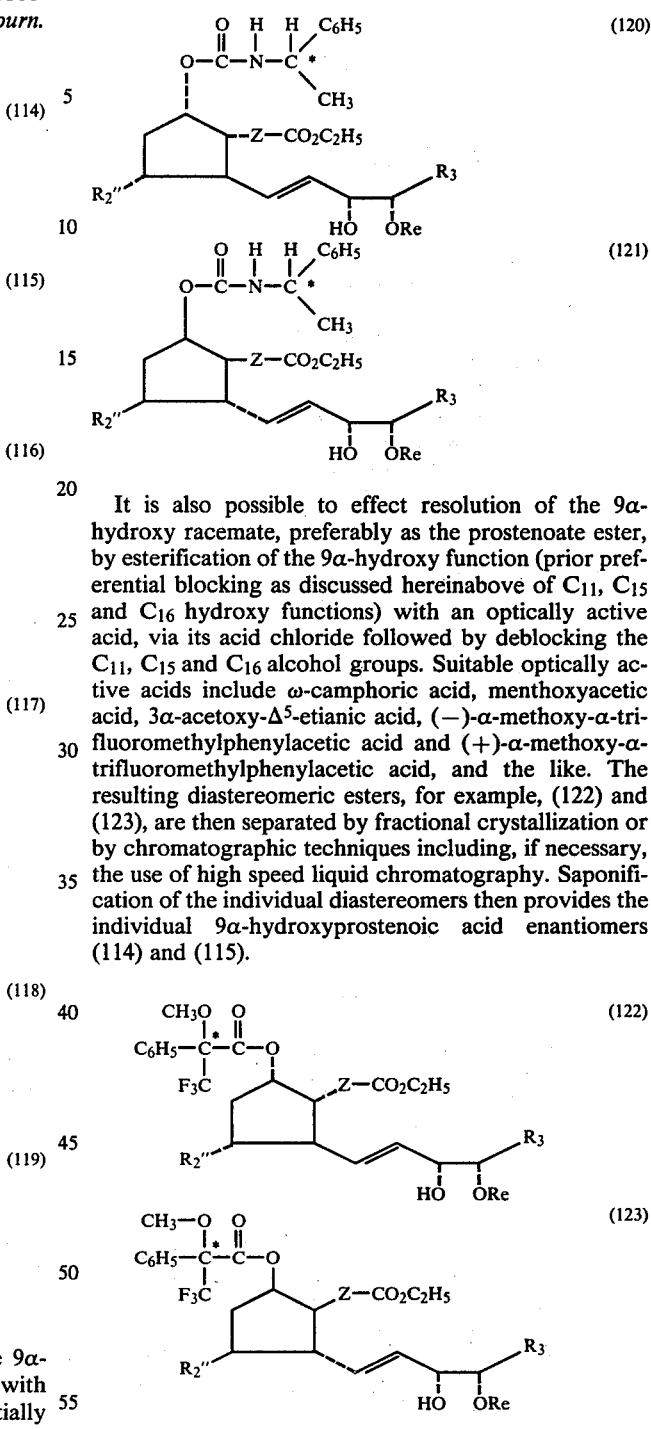

It is also possible to effect resolution of the 9α-hydroxy racemate, preferably as the prostenoate ester, by esterification of the 9α-hydroxy function (prior preferential blocking as discussed hereinabove of $C_{11}$, $C_{15}$ and $C_{16}$ hydroxy functions) with an optically active acid, via its acid chloride followed by deblocking the $C_{11}$, $C_{15}$ and $C_{16}$ alcohol groups. Suitable optically active acids include ω-camphoric acid, menthoxyacetic acid, 3α-acetoxy-Δ⁵-etianic acid, (−)-α-methoxy-α-trifluoromethylphenylacetic acid and (+)-α-methoxy-α-trifluoromethylphenylacetic acid, and the like. The resulting diastereomeric esters, for example, (122) and (123), are then separated by fractional crystallization or by chromatographic techniques including, if necessary, the use of high speed liquid chromatography. Saponification of the individual diastereomers then provides the individual 9α-hydroxyprostenoic acid enantiomers (114) and (115).

Another resolution procedure, less useful than the methods described above which are based on the 9α-hydroxy derivative, but which is particularly applicable to the 11-deoxy compounds of this invention, involves derivatization of the keto function of the 9-oxoprostenoic acid or ester racemate with the usual type of ketone derivatizing agents bearing an optically active center. The resulting mixture of diastereomeric derivatives can then be separated by fractional crystallization or by chromatography or, if necessary, by high speed liquid chromatography. The ndividual diastereomeric keto derivatives, for example (124) and (125), are then convertible to the individual 9-oxo enantiomers for example (126) and (127), by any of the usual cleavage techniques, provided that they are sufficiently mild so as not to disturb the sensitive 11-hydroxy-9-keto-system if it is present. (This latter point is of course not a problem with 11-unsubstituted derivatives.) Ketone reduction of the 9-oxo-enantiomer as described hereinabove then provides the corresponding 9α-hydroxy or 9β-hydroxy enantiomer. Among the optically active reagents useful for ketone derivatization are 1-α-aminoxy-γ-methylpentanoic acid hydrochloride [E. Testa et al., Helv. Chimica Acta, 47 (3), 766 (1973)], menthylhydrazine, and 4α methylbenzylsemicarbazide. A useful procedure for the cleavage of oximes such as (124) and (125) involves treatment of the oxime at about 60° C. for about 4 hours in 1:2 aqueous-tetrahydrofuran buffered with ammonium acetate and containing titanium trichloride.

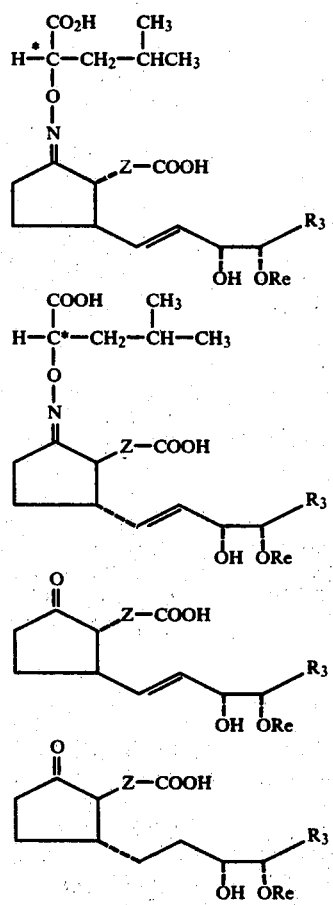

Other useful ketone derivatizing agents are optically active 1,2-glycols, e.g., D(−)-2,3-butanediol, or 1,2-dithiols, e.g., L(+)-2,3-butanedithiol. These are used to convert the 9-oxo racemate to 9,9-alkylenedioxa or 9,9-alkylenedithia diastereomers. Separation of diastereomers by chromatographic procedures, followed by regeneration of the individual 9-oxo enantiomer by ketal cleavage can be accomplished by procedures well-known in the art. Both ketalization and deketalization would have to be accomplished by procedures which would not disrupt the 11-oxo-9-keto system, which of course, is not a problem in the 11-unsubstituted series.

The ring system of certain of the novel compounds of this invention allow them to be characterized as follows:

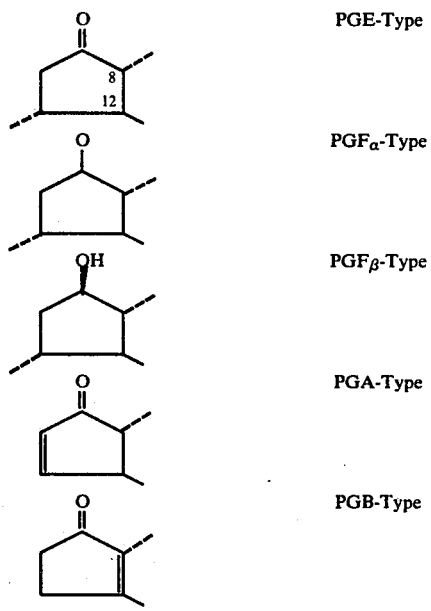

The novel compounds of this invention possess the pharmacological activity described below as associated with the appropriate above-described prostaglandin type.

The known PGE, PGF$_\alpha$, PGF$_\beta$, PGA, and PGB compounds are all potent in causing multiple biological responses even at low doses. For example, PGE$_1$ and PGE$_2$ are extremely potent in causing vasodepression and smooth muscle stimulation, and also are potent as antilipolytic agents. Moreover, for many applications, these known prostaglandinds have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandins analogs is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

The 11-deoxy-PGE, PGFα and PGFβ compounds are additionally selective in that they are at most relatively very weak stimulants of smooth muscle. The 11-deoxy PGE compounds have a further advantage in that they are as much more stable and have a longer "shelf-life" than the corresponding 11-hydroxy derivatives as described more fully hereinbelow.

Another advantage of the novel compounds of this invention, compared with the known prostaglandins, is that these novel compounds are administered effectively, orally, sublingually, intravaginally, bucally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body wit fewer, shorter, or smaller doses, and make possible self-administration by the patient.

$PGE_1$, $PGE_2$, $PGE_3$, and dihydro-$PGE_1$, and the corresponding $PGF_\alpha$, $PGE_\beta$, PGE, and PGB compounds, and their esters and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood pressure lowering in the case of the PGE, and $PGF\beta$ and PGA compounds as measured, for example, in anesthetized (penobarbital sodium) pentoliniumtreated rats with indwelling aortic and right heart cannulas; pressor activity, similarly measured, for the $PGF\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrineinduced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the cetral nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of disease and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 µg. to about 10 mg. per ml. of a pharmacologically suitable liquid vehicle or as an aerosol spray, both for topical application.

The PGE and PGA compounds are useful in mammals, including man and certain useful antimals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 µg. to about 500 µg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The $PGE_1$ compounds are useful whenever it is desired to inhibit platelet aggregation, to reduce the adhesive character of platelets, and to remove or prevent the formation of thrombi in mammals, including man, rabbits, and rats. For example, these compounds are useful in treatment and prevention of myocardial infarcts, to treat and prevent post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg. per kg. of body weight per day are used, the exact dose depending on the age, weight, and condition of the patient or animal, and on the frequency and route of administration.

11α-Hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_2$, for example, is useful in place of or in combination with less than usual amounts of these known smooth muscle stimulators, for example, to relieve the symptoms of paralytic ileus, or to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 µg. per kg. of body weight per minute until the desired effect is obtained. Subsequent doses are given by intravenous, subcutaneous, or intramuscular injection or infusion during puerperium in the range of 0.01 to 2 mg. per kg. of body weight per day, the exact dose depending on the age, weight, and condition of the patient or animal.

The PGE, $PGF\beta$ and PGA compounds are useful as hypotensive agents to reduce blood pressure in mammals including man. For this purpose, the compounds are administered by intravenous infusion at the rate about 0.01 to about 50 µg. per kg. of body weight per minute, or in a single or multiple doses of about 25 to 2500 µg. per kg. of body weight total per day.

The PGE, $PGF\alpha$, and $PGF\beta$ compounds are useful in place of oxytoxin to induce labor in pregnant female animals, including man, cows, sheep, pigs, at or near term or in pregnant animals with intrauterine death of the fetus from about 20 weeks to term. For this purpose, the compound is infused intravenously at a dose 0.01 to 50 µg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started.

The PGE, $PGF\alpha$, and $PGF\beta$ compounds are useful for controlling the reproductive cycle in ovulating female mammals, including humans and other animals. For that purpose, $PGF_2\alpha$, for example, is administered systematically at a dose level in the range of 0.01 mg. to about 20 mg. per kg. of body weight, advantageously during a span of time starting approximately at the time of ovulation and ending approximately at the time of menses or just prior to menses. Additionally, expulsion of an embryo or fetus is accomplished by similar administration of the compound during the first third or the second third of the normal mammalian gestation period. Accordingly they are useful as abortifacients. They are also useful for induction of menses during apprimately the first two weeks of a missed mestrual period and accordingly are useful as contraceptive anti-fertility agents.

The PGA compounds and derivatives and salts thereof increase the flow of blood in the mammalian kidney, thereby increasing volume and electrolyte content of the urine. For that reason, PGA compounds are useful in managin cases of renal disfunction, especially in cases of several impaired renal blood flow, for example, the hepatorena syndrome and early kidney transplant rejection. In case of excessive or inappropriate ADH (antidiuretic hormone vasopressin) secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate a wet dressing for topical application to second and/or third degree burns of skin area 5 to 25 square centimeters would advantageously involve use of an isotonic aqueous solution containing 1 to 500 μg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

The novel compounds of this invention induce the biological responses described hereinabove as associated with its particular prostaglandins type. These novel compounds are accordingly useful for the above-described corresponding purposes in the same manner as described above.

The novel PGE, PGFβ and PGA compounds of this invention are also useful as bronchodilators for the treatment of asthma and chronic bronchitis; as such they may be conveniently administered by inhalation of aerosol sprays prepared in a dose range of about 10 μg. to about 10 mg. per ml. of a pharmacologically suitable liquid vehicle.

In addition certain of the novel compounds of this invention are useful for the preparation of other novel compounds of this invention.

The compounds of this invention are useful as bronchodilators for the treatment of asthma and chronic bronchitis. Bronchodilator activity is determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, *Arzneimittel-Forschung*, 18, 955 (1968).]

In Table A which follows bronchodilator activity for representative compounds of this invention against one or more of three spasmogenic agents is expressed in an $ED_{50}$ determined from the results obtained with three logarithmic cummulative intravenous doses.

TABLE A

| | Bronchodilator Activity (Konzett Assays) $ED_{50}$, mg./kg. Spasmogenic Agent | | |
|---|---|---|---|
| Compound | 5-Hydroxy tryptamine | Histamine | Acetylcholine |
| dl-erythro-9-oxo-11α,15,16-trihydroxy-5-cis,13-trans-prostadienoic acid | 0.024 | 0.0098 | 0.013 |
| dl-erythro-11α,15-epi,16-trihydroxy-5-cis-13-trans-prostadienoic acid | 1.28 | | 2.43 |
| all racemic erythro-9-oxo-15,16-dihydroxy-13-trans-prostenoic acid | .537 | .01 | |
| dl-erythro-9-oxo-15-hydroxy-16-methoxy-13-trans-prostenoic acid | | >3.20 | >0.32 |
| dl-erythro-9-oxo-15-epi-hydroxy-16-methoxy-13-trans-prostenoic acid | 7.99 | >3.20 | >3.20 |

These compounds have an additional importance in that they produce a sustained bronchodilation, when compared to that produced by $PGE_1$ or $PGE_2$ or the standard isoprotproterenol.

The compounds of this invention are also useful as inhibitors of gastric acid secretion and peptic ulcer formation and may be used for the treatment of gastric hyperacidity, gastric erosion, and peptic ulcer. Inhibition of basal gastric acid secretion can be determined by the following procedure.

Female Sprague-Dawley rats weighing 140-160 grams are fasted in individual cages for 18-24 hours. The rats are then lightly anesthetized with ether and their front teeth extracted to avoid destruction of the plastic cannula. A midline incision is then made and the stomach and duodenum exposed. A flanged polyvinyl tube is inserted into the fundic portion of the stomach and secured with a purse string suture line using 4-O Mersilene. The rat is then dosed by injection of the compound into the duodenum (1.0 ml. per 100 gram body weight). After dosing, the abdominal wall and skin are closed using metal wound clips. The rat is replaced in a cage containing a longitudinal slit to allow the polyvinyl tube to hang freely. An 8 ml. plastic collecting tube is attached to the flanged cannula and hangs freely below the cage. The first 30 minute sample is discarded designating this time as zero. The collecting tube is attached again and samples removed at the end of 60 and 120 minutes. The hourly samples are then transferred to a 15 ml. centrifuge and centrifuged for 5-10 minutes. Total and sediment volume are then recorded with the supernatant volume being used as volume of secretion. A 1 ml. or less aliquot is then removed and placed in a 50 ml. beaker containing 10 ml. of distilled water. This sample is then titrated using 0.01 N NaOH to pH 7.0 using a Beckman zeromatic pH meter. Volume, titratable acidity (meq/L) and total acid output (ueg/hour) are recorded. Percent inhibition is determined by comparison with the appropriate control. Groups of three rats were used for preliminary testing, and groups of six rats were used for dose-response evaluations. All compounds are administered in a vehicle consisting of 0.5% methocel, 0.4% tween 80, and saline at a constant volume of 1 ml./100 gram rat. Samples are dispersed by sonification. Percent inhibition is calculated on basis of concurrent vehicle control.

In Table B which follows is given the effect on total acid output after 60 minutes (response A) and 120 minutes (response B) for various doses of representative compounds of this invention.

TABLE B

INHIBITION OF GASTRIC ACID SECRETION IN THE ACUTE GASTRIC FISTULA RAT

| Compound | Dose, mg./kg. | % Inhibition of Total Acid Output After 60 min. | % Inhibition of Total Acid Output After 120 min. |
|---|---|---|---|
| dl-erythro-9-oxo-11α,15,16-trihydroxy-5-cis, 13-trans-prostadienoic acid | 10$^a$<br>5$^b$ | 98<br>86 | 55<br>89 |
| dl-erythro-9-oxo-11α,15-epi,16-trihydroxy-5-cis,13-trans-prostadienoic acid | 10$^a$<br>10$^b$ | 100<br>66 | 82<br>65 |
| dl-erythro-9-oxo-15,16-dihydroxy-13-trans-prostenoic acid | 2.5$^a$ | 77 | 76 |
| dl-erythro-9-oxo-15-epi-16-dihydroxy-13-trans-prostenoic acid | 10$^a$ | 0 | 42 |
| all racemic erythro ethyl 9-oxo-15-hydroxy-16-methoxy-13-trans-prostenoate | 10$^a$ | 43 | 0 |
| all racemic erythro-9-oxo-11-tetrahydropyranyloxy-15,16-isopropylidenodioxy-5-cis,13-trans-prostadienoic acid | 10$^a$ | 55 | 29 |
| all racemic erythro-9-oxo-15,16-dihydroxy-prostanoic acid | 10$^a$ | 56 | 46 |

$^a$intraduodenal route of administration
$^b$oral route of administration

The compounds of the present invention exhibit hypotensive activity when tested in the following procedure:

The animals used are Royalhart, Wistar strain, male, normotensive rats weighing 250-300 g. The rats are anesthetized using a 100 mg./ml. saline solution of urethane at a rate of 900 mg./kg. intraperitoneally.

The instrumentation used in a Brush model 260 recorder, Statham mode P23Db pressure transducer and Harvard model 940 infusion pump with a 6 cc syringe at speed 4.

The left carotid artery is cannulated with polyethylene tubing for arterial blood pressure. The left external juglar vein is cannulated with polyethylene tubing for bration period the test compound is infused over a one minute period in a volume of 0.5 ml., at a concentration of 2.5 mg./kg. in one of three diluents (ethanol, 1 M NaHCO$_3$ or saline) and then flushed with 0.4 ml. of saline.

Mean arterial blood pressure is then measured in two test animals per compound against a control value. In Table C below is recorded the hypotensive effect of representative compounds of this invention, as determined by this assay.

TABLE C

| Compound | Dose, mg./kg. | % Decrease Mean Arterial Blood Pressure |
|---|---|---|
| dl-erythro-9-oxo-15,16-dihydroxy-13-trans-prostenoic acid | 2.1 | 23 |
| dl-erythro-ethyl-9-oxo-15-epi,16-dihydroxy-13-trans-prostenoate | 2.4 | 33 |
| dl-erythro-9-oxo-15,16-isopropylidenedioxy-13-trans-prostenoic acid (epimeric mixture) | 2.5<br>1.3 | 21<br>63 |
| dl-erythro-9-oxo-11α,15,16-trihydroxy-5-cis,13-trans-prostadienoic acid | 0.1 | 6 |
| dl-erythro-9-oxo-11α,15-epi,16-trihydroxy-5-cis,13-trans-prostadienoic acid | 2.0 | 57 |
| dl-erythro-ethyl-9-oxo-15-epi-hydroxy-16-methoxy-13-trans-prostenoate | 2.3 | 9 |
| di-erythro-9-oxo-15-hydroxy-16-methoxy-13-trans-prostenoic acid | 2.1 | 29 |
| dl-erythro-9-oxo-15-epi-15-hydroxy-16-methoxy-13-trans-prostenoic acid | 2.4 | 18 |

TABLE C-continued

| Compound | Dose, mg./kg. | % Decrease Mean Arterial Blood Pressure |
|---|---|---|
| dl-erythro-9-oxo-11α,15-dihydroxy-16-methoxy-5-cis,13-trans-prostadienoic acid | 1.8 | 44 |
| dl-erythro-9-oxo-11α,15-epi-15-hydroxy-16-methoxy-5-cis,13-trans-prostadienoic acid | 1.9 | 19 |
| dl-erythro-9α,11α,15-epi,16-tetrahydroxy-5-cis,13-trans-prostadienoic acid | 2.2 | 20 |
| dl-erythro-9-oxo-15-epi,16-dihydroxy-5-cis,10,13-trans-prostatrienoic acid | 2.1 | 54 |
| dl-erythro-9-oxo-15-hydroxy-16-methoxy-5-cis,10,13-trans-prostatrienoic acid | 1.9 | 26 |

This invention will be described in greater detail in conjunction with the following specific examples.

EXAMPLE 1

Preparation of 3-tetrahydropyranyloxy-1-propyne

To a stirred solution of 112 g. (2.0 mol.) of 3-hydroxy-1-propyne and 260 g. (3.0 mol.), of dihydropyran in 1.20 l. of methylene chloride cooled to 0° C. in an ice bath, is added a solution of 20 mg. of para-toluenesulfonic acid in 100 ml. of methylene chloride, dropwise. The reaction mixture is stirred at 0° C. for one-half hour, and at ambient temperature for one hour. It is then poured into 200 ml. of a 5% solution of sodium bicarbonate, the organic phase is separated, the aqueous phase extracted with 100 ml. of methylene chloride, the combined organic phases washed with 100 ml. of a solution of brine, dried over sodium sulfate, and evaporated under vacuum (12 mm.) at 45° C., to give 300 g. of crude product, which is purified by fractional distillation, b,p, 71°-73° C. (14 mm.) to yield 250 g. (89%) of a liquid.

EXAMPLE 2

Preparation of 3-tetrahydropyranyloxy-1-trimethylsilyl-1-propyne

To a stirred −20° C. solution of 125 g. (0.89 mol.) of 3-tetrahydropyranyloxy-1-propyne (Example 1) in 450 ml. of ether, under a nitrogen atmosphere, is added dropwise, over one hour, a solution of 45 ml. (0.89 mol.) of 2.0 N n-butyl-lithium in hexane. After 150 ml. of dry ether is added and the mixture stirred at −20° C. for 30 minutes, a solution of 98 g. (0.89 mol.) of trimethylchlorosilane in 73 ml. of ether is added dropwise, stirring is continued for 30 minutes at −20° C., and at ambient temperature for 18 hours. The reaction mixture is again cooled to −20° C., and a solution of 90 ml. of acetic acid in 300 ml. of ether is added dropwise, followed by 90 ml. of water. It is then diluted with 500 ml. of water, and extracted 3 times with 300 ml. of a 5% sodium bicarbonate solution. The organic phase is separated, washed with 500 ml. of a saturated brine solution, dried over sodium sulfate, and evaporated at 40° C. under vacuum (12 mm.). The crude product is fractionally distilled, b.p. 120°-125° C. (18 mm.), to yield 120 g. of an oil.

EXAMPLE 3

Preparation of d,l-erythro-3-tetrahydropyranyloxy-4-hydroxy-1-trimethylsilyl-1-octyne To a stirred −78° C. solution of 62 ml. (124 mmol.) of a 2.0 M solution of n-butyllithium in hexane and 50 ml. of dry tetrahydrofuran, under a nitrogen atmosphere is added dropwise a solution of 24 g. (113 mmol.) of 3-tetrahydropyranyloxy-1-trimethylsilyl-1-propyne (Example 2) in 35 ml. of tetrahydrofuran. This red solution is stirred one hour at −78° C. then a freshly prepared solution of zinc iodide (135 mmol.) in 125 ml. of tetrahydrofuran [F. Mercier, R. Epsztein, and S. Holand, Bull. Soc. Chim. France, 2, 690, (1972)] is added dropwise at −78° C. until the mixture turns yellow. After stirring an additional hour at −78° C., a solution of 21 g. (250 mmol.) of n-valeraldehyde in 35 ml. of tetrahydrofuran is added dropwise and the reaction mixture stirred for one hour at −78° C. and 18 hours at ambient temperature. It is then cooled to 0° C. and a solution of 12 ml. of acetic acid in 65 ml. of ether is added dropwise, followed by 75 ml. of ice-water. The phases are separated and the aqueous phase is extracted twice with ether. The combined organic phases are washed 3 times with saturated sodium bicarbonate solution, until the last wash is basic, then with a saturated brine solution, dried over sodium sulfate, and evaporated to give 40 g. of a yellow oil. The crude product may be purified on a 4″×40″ dry column of alumina, and eluted with chloroform. I.R.: neat; 3550 (OH), 2200 (C≡C), 840, 750 [(CH$_3$)$_3$Si], cm$^{-1}$.

EXAMPLE 4

Preparation of d,l-erythro-3,4-dihydroxy-1-trimethylsilyl-1-octyne

A solution of 19.6 g. (0.066 mol.) of d,l-erythro-3-tetrahydropyranyloxy-4-hydroxy-1-trimethylsilyl-1-octyne (Example 3) in 55.5 ml. of ethanol, 22.2 ml. of acetic acid, and 22.2 ml. of water is heated at reflux for 3 hours. The cooled mixture is taken to dryness and evaporated twice with benzene. The residue is taken up in hexane, washed 3 times with saturated potassium bicarbonate solution, dryed with magnesium sulfate, and evaporated to give 17.0 g. of crude product.

IR: neat, 3500–3400, broad (two OH)

EXAMPLE 5

Preparation of d,l-erythro-3,4-isopropylidenedioxy-1-trimethylsilyl-1-octyne

To a stirred solution of 17.0 g. (79.5 mmol.) of crude d,l-erythro-15,16-dihydroxy-1-trimethylsilyl-1-octyne (Example 4) in 33.6 ml. of 2,2-dimethoxy propane at 0° C., is added 0.05 ml. of 60% perchloric acid. After 30 minutes at ambient temperature, the mixture is shaken with 50 ml. of hexane and 25 ml. of saturated sodium bicarbonate solution. The hexane phase is separated, dryed with magnesium sulfate, and evaporated to give 19.0 g. of crude product.

EXAMPLE 6

Preparation of
d,l-erythro-3,4-isopropylidenedioxy-1-octyne

A mixture of 19.0 g. (75.0 mmol.) of crude d,l-erythro-3,4-isopropylidenedioxy-1-trimethylsilyl-1-octyne (Example 5) with 95 ml. of methanol and 3.0 g. of potassium carbonate is refluxed for one hour. The mixture is cooled and evaporated at 50° C. (13 mm.), taken up in 250 ml. of benzene, and washed with 100 ml. of water. The water is saturated with salt, the organic phase separated, dried with mangesium sulfate, and evaporated to give 12 g. of crude product. Fractional distillation yields 7.0 g. of the subject compound as a colorless oil, b.p. 103°–106° C. (13 mm.).

IR: neat; 3300 sharp (H—C≡C), 2100, (C≡C), 780 (erythro configuration) cm$^{-1}$ nmr: $\delta_{TMS}^{CDCl_3}$; 4.75 (dd., 1, C≡C—C$\underline{H}$—CH, J=2 Hz, J=5 Hz), 4.10 (m, 1, C≡C—CH—C$\underline{H}$—CH$_2$, 2.5 (d, 1, $\underline{H}$—C≡C—CH), 1.9–1.2 (m, 14, alkyl), 0.90 (m, 3H, CH$_2$C$\underline{H}_3$).

EXAMPLE 7

Preparation of
d,l-erythro-1-iodo-3,4-isopropylidenedioxy-trans-1-octene

To a stirred 0° C. slurry of 0.852 g. (0.023 mol.) of sodium borohydride and 4.21 g. (0.060 mol.) of 2-methyl-2-butene in 40 ml. of dry tetrahydrofuran, under an argon atmosphere, is added dropwise 4.26 g. (0.030 mol.) of boron trifluoride etherate complex. A solution of 2.73 g. (0.015 mol.) of d,l-erythro-3,4-isopropylidenedioxy-1-octyne (Example 6) in 5 ml. of tetrahydrofuran in added dropwise, the ice bath removed, and the mixture allowed to stir at ambient temperature for two hours. It is then cooled again to 0° C., and 2.88 g. (0.105 mol.) of dry trimethylamine oxide is added in portions over 30 minutes. After stirring 3 hours at room temperature, this mixture is poured simultaneously with a 0° C. solution of 21.3 g. of iodine in 53 ml. of tetrahydrofuran into 766 ml. of a 0° C. 15% solution of sodium hydroxide in water and the whole stirred vigorously at 0° C. for 45 minutes. The organic phase is separated, the aqueous phase is extracted twice with ether, the combined organic phases are washed with a 5% solution of sodium thiosulfate, dried with magnesium sulfate, and evaporated. The crude product is chromatographed on a 2″×40″ dry column of silica gel, by eluting with chloroform, to yield 1.2 g. (25%) of a yellow oil. IR: neat; 1599 sharp, 945

cm$^{-1}$.

EXAMPLE 8

Preparation of
d,l-erythro-3-tetrahydropyranyloxy-4-acetyloxy-1-trimethylsilyl-1-octyne A solution of 3.0 g. (13.2 mmol.) of d,l-erythro-3-tetrahydropyranyloxy-4-hydroxy-1-trimethylsilyl-1-octyne is heated at 100° C. for 15 hours with 3 ml. of acetic anhydride and 10 ml. of pyridine. The mixture is evaporated to dryness, dissolved in ether, washed with sodium bicarbonate solution and water. The organic phase is dried over magnesium sulfate and evaporated to give 2.5 g. of the subject compound as an oil.

IR: neat; 2200 (C≡C), 1730 (C=O), 830, 760 [(CH$_3$)$_3$Si], cm$^{-1}$.

EXAMPLE 9

Preparation of
d,l-erythro-3-hydroxy-4-acetyloxy-1-trimethylsilyl-1-octyne

In the manner of Example 4, 2.5 g. (7.4 mmol.) of d,l-erythro-3-tetrahydropyranyloxy-4-acetyloxy-1-trimethylsilyl-1-octyne (Example 8) in a solution of ethanol, acetic acid, and water is heated at 100° C. for 3 hours. After workup, the crude product is chromatographed on a ⅞″×22″ dry column of silica gel, and eluted with chloroform to give 1.0 g. of a yellow oil.

IR: neat; 3500 (OH), 1730 (C=O), cm$^{-1}$.

EXAMPLE 10

Preparation of
d,l-erythro-3-paratoluenesulfonyloxy-4-acetyloxy-1-trimethylsilyl-1-octyne To a solution of 7.5 g. (41.0 mmol.) of d,l-erythro-3-hydroxy-4-acetyloxy-1-trimethylsilyl-1-octyne (Example 9) in 41 ml. of dry pyridine is added 11.0 g. (58 mmol.) of paratoluenesulfonyl chloride and the resulting solution is stirred at 25° C. for 15 hours. The mixture is then warmed at 40° C. for one hour, and after cooling, partitioned between 500 ml. of diethyl ether and 100 ml. of 1.0 N hydrochloric acid. The organic phase is washed three times with 100 ml. of 1.0 N hydrochloric acid, once with dilute sodium bicarbonate solution, dried over magnesium sulfate, and evaporated under reduced pressure to give an oil. The crude product is purified on a 2″×24″ dry column of silica gel, and eluted with chloroform to yield a yellow oil.

IR: neat; 1730 (C=O), 1595 (aromatic) cm$^{-1}$.

EXAMPLE 11

Preparation of
d,l-threo-3-hydroxy-4-acetyloxy-1-trimethylsilyl-1-octyne

A mixture of 15.5 g. (39.0 mmol.) of d,l-erythro-3-para-toluenesulfonyloxy-4-acetyloxy-1-trimethylsilyl-1-octyne (Example 10), 5.0 g. of calcium carbonate, 25 ml. of water and 250 ml. of tetrahydrofuran is refluxed with stirring for 4 days. The mixture is cooled, 100 ml. of water added and the organic phase separated. The aqueous phase is extracted with ether, the combined organic phases dried with magnesium sulfate, and evaporated. The crude product is chromatographed on a 3″×30″ dry column of silica gel, and eluted with chloroform to give 7.0 g. of an oil.

IR: neat; 3500, (OH), cm$^{-1}$.

EXAMPLE 12

Preparation of d,l-threo-3,4-dihydroxy-1-octyne

A solution of 7.0 g. (28 mmol.) of d,l-threo-3-hydroxy-4-acetyloxy-1-trimethylsilyl-1-octyne (Example 11) in 50 ml. of methanol is stirred at room temperature for 24 hours with a solution of 6.3 g. (112 mmol.) of potassium hydroxide in 50 ml. of water. The mixture is extracted twice with hexane, washed with 0.5 M hydrochloric acid, brine, and dried with magnesium sulfate. After evaporation, the subject compound is obtained as a yellow oil.

IR: neat, 2500 broad (2-OH), cm$^{-1}$.

EXAMPLE 13

Preparation of
d,l-threo-3,4-isopropylidenedioxy-1-octyne

In the manner of Example 6, treatment of a solution of d,l-threo-3,4-dihydroxy-1-octyne (Example 12) in dimethoxypropane with 60% perchloric acid, and fractional distillation (12 mm.) is productive of the subject compound as a colorless oil, containing 15% of d,l-erythro-3,4-isopropylidenedioxy-1-octyne (Example 6), as an impurity.

IR: neat; 810 (threo configuration).

nmr: $\delta_{TMS}^{CDCl_3}$ 4.2 (dd, 1, —C≡C—CH—, J's—2 H$_z$, 6 H$_z$), 4.1–3.9 (m, 1, —C≡C—C$\underline{H}$—CH—CH$_2$—), 2.5 (d, 1, H—C C—, J=2H$_z$), 1.9–1.2 (m, 14, alkyl), 0.90 (m, 3H, CH$_2$-C$\underline{H}_3$).

EXAMPLE 14

Preparation of
d,l-threo-1-iodo-3,4-isopropylidenedioxy-trans-1-octene

In the manner of Example 7, d,l-threo-3,4-isopropylidenedioxy-trans-1-octyne (Example 13) is treated successively with disiamylborane, trimethylamine oxide, iodine, and sodium hydroxide to give the subject compound.

EXAMPLE 15

Preparation of
d,l-erythro-3-tetrahydropyranyloxy-4-hydroxy-1-octyne

Alkaline hydrolysis of d,l-erythro-3-tetrahydropyranyloxy-4-hydroxy-1-trimethylsilyl-1-octyne (Example 3), by the procedure of Example 6 is productive of the subject compound.

EXAMPLE 16

Preparation of
d,l-erythro-3-tetrahydropyranyloxy-4-methoxy-1-octyne

To a stirred slurry of 6.0 g. (150 mmol.) of a 60% oil dispersion of sodium hydride i- 96 g. of iodomethane, under an argon atmosphere, is added 700 ml. of dry tetrahydrofuran. The stirred mixture is cooled to −20° C. and a solution of 30 g. (133 mmol.) of d,l-erythro-3-tetrahydropyranyloxy-4-hydroxy-1-octyne (Example 15), is added dropwise, followed by 0.1 ml. of methanol. The mixture is stirred at ambient temperature for 24 hours, 10 ml. of methanol is added, and evaporated. The residue is taken up in ether, washed 3 times with water, dried over magnesium sulfate, and evaporated. The crude product is purified by fractional distillation to yield 16.3 g. of a colorless oil, b.p. 137°–140° C. (12 mm.).

EXAMPLE 17

Preparation of
d,l-erythro-3-tetrahydropyranyloxy-4-methoxy-1-iodo-trans-1-octene In the manner of Example 7, 1.20 g. (5.0 mmol.) of d,l-erythro-3-tetrahydropyranyloxy-4-methoxy-1-octyne (Example 16) is treated successively with disiamylborane, trimethylamine oxide, iodine, and sodium hydroxide. Chromatography on a 2"×36" dry column of silica gel and elution with chloroform is productive of 0.80 g. (40%) of the subject compound as an oil.

nmr: $\delta_{TMS}^{CDCl_3}$; 7.9–6.1 (m, 2, HC=CH), 4.9–4.6 (2 m, 2, C=C—CH, O—CH—O), 4.3–4.0 (m, 1, c=c—CH—C$\underline{H}$—CH$_2$), 3.9–3.0 (m, 6, CH$_2$—O—C$\underline{H}$, OCH$_3$), 1.8–1.2 (m, 12H, alkyl), 0.9 (m, 3, —CH$_3$).

EXAMPLE 18

Preparation of
d,l-erythro-3-hydroxy-4-methoxy-1-iodo-trans-1-octene

A solution of 3.10 g. (8.24 mmol.) of d,l-erythro-3-tetrahydropyranyloxy-4-methoxy-1-iodo-trans-1-octene (Example 17) in 60 ml. of acetic acid, 30 ml. of tetrahydrofuran, and 15 ml. of water is stirred at ambient temperature for 18 hours. It is then evaporated at 70° C. under high vacuum (1.0 mm.), and three times with 40 ml. of toluene to give the crude product as an oil.

EXAMPLE 19

Preparation of
d,l-erythro-3-trimethylsilyloxy-4-methoxy-1-iodo-trans-1-octene

To a stirred solution of 3.0 g. (10.2 mmol.) of d,l-erythro-3-hydroxy-4-methoxy-1-iodo-trans-1-octene (Example 18) in 11.0 ml. of dry dimethylformamide and 1.90 g. (28.0 mmol.) of imidazole cooled to 0° C. is added, dropwise, 1.35 g. (12.5 mmol.) of trimethylsilyl chloride. The reaction mixture is stirred a further 4 hours at room temperature. It is then poured into a mixture of 100 ml. of hexane and 25 ml. of water, the organic phase is separated, washed twice with water, once with a solution of saturated sodium chloride, dried over magnesium sulfate, and evaporated. The crude product is purified by fractional distillation to yield 2.0 g. of a colorless oil, b.p. 82°–83° C. (0.3 mm.).

IR: neat; 1602 sharp

840, 750 broad [(CH$_3$)$_3$Si-], cm$^{-1}$.

EXAMPLE 20

Preparation of
d,l-erythro-ethyl-9-oxo-15,16-isopropylidenedioxy-13-trans-prostenoate To 0.31 g. (1.0 mmol.) of d,l-erythro-1-iodo-3,4-isopropylidenedioxy-trans-1-octene (Example 7) cooled to −78° C. under an argon atmosphere is added 3.0 ml. (2.24 mmol.) of a 0.75 N solution of t-butyllithium in pentane. The mixture is stirred for one hour at −78° C. A solution of 0.13 g. (1.0 mmol.) of cuprous pentyne [C. E. Castro, E. J. Gaughan, and D. C. Owsley, *Jour. Org. Chem.*, 12, 4071 (1966)] in 0.4 ml. (3.6 mmol.) of hexamethylphosphorustriamide, together in 5 ml. of dry ether, is added to the above vinyl lithium solution and stirring continued at −78° C. for one hour. To the resulting mixture, 0.24 g. (1.0 mmol.) of 2-(6-carbethoxyhexyl)cyclopent-2-en-1-one in 3 ml. of ether is added at −78° C. The reaction mixture is stirred for one hour at −78° C., one hour at −20° C., and one hour at 0° C. It is then quenched, by pouring into a mixture of a 50 ml. solution of saturated ammonium chloride, and 50 ml. of hexane, and stirred vigorously for one-half hour. The organic phase is separated, the aqueous phase extracted with ether, the combined organic phases washed 3 times with a solution of 0.5% sulfuric acid and then with brine; it is dried over magnesium sulfate and evaporated. The oil containing the subject product is chromatographed on a 1½"×40" dry column of silica gel, and eluted with a mixture of one part of ethyl acetate to nine parts of benzene, to give 190 mg. (40%) of a light yellow oil.

IR: neat; 1730 (C=O),

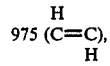

cm$^{-1}$.

nmr: $\delta_{TMS}^{CDCl_3}$; 5.7 (m, 2, CH=CH), 4.6–4.0 (m, 4, OCH-CHO, OC$\underline{H}_2$CH$_3$), 2.4–1.1 (m, 35, alkyl), 0.9 (m, 3H, CH$_2$CH$_3$).

EXAMPLE 21

Alternate preparation of d,l-erythro ethyl 9-oxo-15,16-isopropylidenedioxy-13-trans-prostenoate To 1.57 g. (5.0 mmol.) of d,l-erythro-1-iodo-3,4-isopropylidenedioxy-trans-1-octene (Example 7), cooled to −78° C. under an argon atmosphere, is added 2.5 ml. (5.0 mmol) of a 2.0 M solution of n-butyllithium in hexane. This solution is stirred one hour at −78° C. To the resulting vinyllithium solution is added 1.02 g. (2.58 mmol.) of tributylphosphine cuprous iodide complex in 8.0 ml. of ether and the mixture stirred at −78° C. for one hour. A solution of 0.804 g. (2.5 mmol.) of 2-(6-carbethoxyhexyl)-cyclopent-2-en-1-one [K. F. Bernady and M. J. Weiss, *Tetrahedron Letters,* 4083 (1972)] in 6.0 ml. of ether is next added to the above mixture and the whole stirred at −15° C. for one hour and 0° C. for one hour. The reaction mixture is quenched, worked up, and chromatographed in the same manner as Example 19 to give 0.820 g. (77%) of product identical to that prepared using cuprous pentyne.

EXAMPLE 22

Preparation of d,l-erythro ethyl 9-oxo-15,16-dihydroxy-13-trans-prostenoate and d,l-erythro ethyl 9-oxo-15-epi-16-dihydroxy-13-trans-prostenoate A solution of 0.650 g. (1.54 mmol.) of d,l-erythro ethyl 9-oxo-15,16-isopropylidenedioxy-13-trans-prostenoate (Example 20 or 21) in 12 ml. of acetic acid, 6 ml. of tetrahydrofuran and 3 ml. of water is heated at 45° C. for 4 hours. The solution is taken to dryness and evaporated 3 times with benzene under high vacuum at 50° C. The oil containing the subject product is chromatographed on a 1"×30" dry column of silica gel and eluted with a mixture of 20% ethyl acetate and 80% benzene to give 160 mg. each of the two epimeric subject products as yellow oils.

IR: neat; 3500 broad, (2-OH), cm$^{-1}$.

nmr: $\delta_{TMS}^{CDCl_3}$; 5.7 (m, 2, CH=CH), 4.1 (m, 3, OC$\underline{H}_2$CH$_3$, C=C—C$\underline{H}$OH), 3.7 (m, 1, HOC$\underline{H}$CH$_2$), 2.5–1.2 (m, 29, alkyl, and 2—O$\underline{H}$), 0.9 (m, 3, CH$_2$C$\underline{H}_3$).

EXAMPLE 23

Preparation of d,l-erythro-9-oxo-15,16-dihydroxy-13-trans-prostenoic acid

To a solution of 100 mg. (0.26 mmol.) of d,l-erythro ethyl 9-oxo-15,16-dihydroxy-13-trans-prostenoate (Example 22) in 1.0 ml. of methanol, is added 0.3 ml. of a 2.5 N solution of sodium hydroxide and the resulting solution is stirred for 3 hours at ambient temperature. The reaction mixture is then diluted with 5 ml. of water, acidified with 6.0 N hydrochloric acid, saturated with sodium chloride, and extracted three times with ether. The combined organic phases are dried with sodium sulfate, and evaporated to give the product as an oil. This is dissolved in 1.0 ml. of ethyl acetate, 5.0 ml. of heptane is added, and the solution cooled to yield 50 mg. of colorless crystals, m.p. 81°–83° C.

nmr: $\delta_{TMS}^{CDCl_3}$; 6.4–6.1 (bs., 3, 2-OH, COOH), 5.85 (m, 2, HC=CH), 4.2–3.8 (m, 2, HOC$\underline{H}$—HOC$\underline{H}$), 2.4–1.2 (m, 24, alkyl), 0.9 (m, 3, CH$_2$CH$_3$).

EXAMPLE 24

Preparation of d,l-erythro-9-oxo-15-epi,16-dihydroxy-13-trans-prostenoic acid

In the manner of Example 23, d,l-erythro ethyl 9-oxo-15-epi,16-dihydroxy-13-trans-prostenoate (Example 22) is treated with a solution of sodium hydroxide in methanol to give the subject compound as an oil.

EXAMPLE 25

Preparation of d,l-erythro-9-oxo-15,16-isopropylidenedioxy-13-trans-prostenoic acids and d,l-erythro-9-oxo-15-epi,16-isopropylidenedioxy-13-trans-prostenoic acid In the manner of Example 21, saponification of d,l-erythro ethyl 9-oxo-15,16-isopropylidenedioxy-13-trans-prostenoate (Examples 20 or 21) and chromatography on a dry column of silica gel with elution by a mixture of 20% ethyl acetate-in-benzene and 1% of acetic acid, is productive of the subject compounds.

nmr: $\delta_{TMS}^{CDCl_3}$; 10.3–10.1 (bs., 1, COOH), 5.8–5.6 (m, 2, CH=CH), 4.5 (m, 1, C=C—C$\underline{H}$—CH), 4.2 (m, 1, C=C—CH—C$\underline{H}$—CH$_2$), 2.7–1.2 (m's, 29, alkyl), 0.9 (m, 3, CH$_2$C$\underline{H}_3$).

EXAMPLE 26

Preparation of d,l-erythro-9-oxo-11α-tetrahydropyranyloxy-15,16-isopropylidenedioxy-5-cis,13-trans-prostadienoic acid In the manner of Example 20, conjugate addition of 4.96 g. (16.0 mmol.) of d,l-erythro-1-iodo-3,4-isopropylidenedioxy-trans-1-octene to 5.35 g. (16.0 mmol) of 2-(6-carbotetrahydropyranyloxy-2-cis-hexenyl)-4-tetrahydropyranyloxy-cyclopent-2-en-1-one (U.S. Pat. No. 3,873,607; Mar. 25, 1975) is followed by the same workup procedure as in Example 18. The mixture obtained is then stirred at 25° C. for one hour in 500 ml. of a solution of 100 ml. of acetic acid to 100 ml. of tetrahydrofuran and 40 ml. of water. An equal volume of water is then added and the mixture is extracted 3 times with ether, washed with a solution of brine, and dried over magnesium sulfate to give a yellow oil containing the product. This is chromatographed on a 3"×40" dry column of silica gel, and eluted with a solution of 0.5% acetic acid in ether to yield 1.10 g. (14 percent) of chromatographically pure product, which is a 15-epimeric mixture.

IR: neat, 3550 (COOH), 1740, 1700 (C=O),

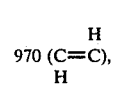

cm$^{-1}$.

EXAMPLE 27

Preparation of
d,l-erythro-9-oxo-11α-hydroxy-15,16-isopropylidene-dioxy-5-cis,13-trans-prostadienoic acid and
d,l-erythro-9-oxo-11α-hydroxy-15-epi,16-isopropylidenedioxy-5-cis,13-trans-prostadienoic acid A solution of 492 mg. (1 mmol.) of d,l-erythro-9-oxo-11α-tetrahydropyranyloxy-15,16-isopropylidenedioxy-5-cis,13-trans-prostadienoic acid (Example 26) in 20 ml. of acetic acid, 10 ml. of tetrahydrofuran and 5 ml. of water is stirred and heated at 45° C. for 2.5 hours. Using high vacuum at 45° C. the solution is taken to dryness and evaporated twice with benzene to give an oil containing the subject product and other products of the deblocking, as in Example 26. The subject epimeric products are obtained by chromatography on a 2"×40" dry column of silica gel and eluted with a solution of 0.5% acetic acid in ether.

EXAMPLE 28

Preparation of
d,l-erythro-9-oxo-11α,15,16-trihydroxy-5-cis,13-trans-prostadienoic acid and
d,l-erythro-9-oxo-11α,15-epi,16-trihydroxy-5-cis,13-trans-prostadienoic acid In the manner of Example 27, treatment of d,l-erythro-9-oxo-11α-tetrahydropyranyloxy-15,16-isopropylidenedioxy-5-cis,13-trans-prostadienoic acid (Example 26) with acetic acid, tetrahydrofuran, and water at 55° C. for 8 hours, and subsequent dry column chromatography is productive of the subject compounds.
nmr: $\delta TMS^{CDCl_3}$; 6.5–5.2

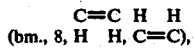
(bm., 8, H H, C=C),

4 OH, 4.5–3.5 (bm., 3, OCH), 2.8–1.1 (bm, 18, alkyl), 0.9 (m, 3, CH$_2$CH$_3$).

EXAMPLE 29

Preparation of
d,l-erythro-ethyl-9-oxo-15-tetrahydropyranyloxy-16-methoxy-13-trans-prostenoate and its 15-epimer The conjugate addition of 377 mg. (1.0 mmol.) of d,l-erythro-3-tetrahydropyranyloxy-4-methoxy-1-iodo-trans-1-octene (Example 17) to 238 mg. (1.0 mmol.) of 2-(6-carbethoxyhexyl)cyclopent-2-en-1-one, by the methods of Example 20, with subsequent dry column chromatography is productive of the subject compounds as a pale yellow oil, as an 15-epimeric mixture.
IR: neat;

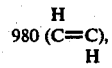

cm$^{-1}$.

EXAMPLE 30

Preparation of d,l-erythro ethyl
9-oxo-15-hydroxy-16-methoxy-13-trans-prostenoate and d,l-erythro ethyl
9-oxo-15-epi-hydroxy-16-methoxy-13-trans-prostenoate Acid hydrolysis of 15-epimeric d,l-erythro ethyl 9-oxo-15-tetrahydropyranyloxy-16-methoxy-13-trans-prostenoate (Example 29), and purification by dry column chromatography following the manner of Example 27 is productive of the two epimeric subject products.
IR: neat; 3550 (OH), cm$^{-1}$.

EXAMPLE 31

Preparation of
2-(6-carbotrimethylsilyloxy-2-cis-hexenyl)-4-trimethylsilyloxy-cyclopent-2-en-1-one To a stirred solution of 25.28 g. (0.114 mol.) of 2-(6-carboxy-2-cis-hexenyl)-4α-hydroxy-cyclopent-2-en-1-one [(M. B. Floyd, Synthetic Communications, 4, 37 (1974)] and 42.06 g. (0.392 mol.) of trimethylchlorosilane in 50 ml. of dry dimethylformamide, under a nitrogen atmosphere, cooled in an ice bath, is added dropwise 25.28 g. (0.250 mol.) of triethylamine. The mixture is next stirred and heated at 65° C. for four hours and at room temperature for 15 hours. It is then cooled, filtered, and the solvent removed under high vacuum (1.0 mm.) at 40° C. The residue is dissolved in one liter of hexane, activated charcoal added, and filtered through a pad of florisil and celite. In the same manner, the solution is again clarified, evaporated under vacuum and dried under high vacuum at room temperature for 15 hours to give 25.13 g. of an oil.

EXAMPLE 32

Preparation of
d,l-erythro-1-iodo-3,4-dihydroxy-trans-1-octene

A solution of 1.40 g. (4.50 mmol.) of d,l-erythro-1-iodo-3,4-isopropylidenedioxy-trans-1-octene (Example 7) in 30 ml. of acetic acid, 10 ml. of tetrahydrofuran and 10 ml. of water is stirred and heated at 50° C. for five hours. It is then evaporated at 40° C. under high vacuum (1.0 mm.), and twice more with 50 ml. of benzene. Crystallization from 10 ml. of chloroform at 0° C. is productive of 700 mg. of the white crystalline subject product.

EXAMPLE 33

Preparation of
d,l-erythro-1-iodo-3,4-bis-trimethylsilyloxy-trans-1-octene

To a stirred solution of 700 mg. (2.40 mmol.) of d,l-erythro-1-iodo-3,4-dihydroxy-trans-1-octene (Example 32) and 800 mg. (12.0 mmol.) of imidazole, in 10 ml. of dry dimethylformamide at 0° C. is added dropwise 1.20 g. (11.0 mmol.) of trimethylchlorosilane. The ice bath is removed, and the mixture is stirred and heated at 50° C. for five hours. It is then cooled, shaken with 50 ml. of hexane and 50 ml. of water, the organic layer separated and washed with 15 ml. of 0.5 M hydrochloric acid, 15 ml. of a saturated solution of sodium bicarbonate, dried with magnesium sulfate, and evaporated. This crude product is fractionally distilled, b.p. 90°–92° C. (0.40 mm.) to yield 250 mg. of a colorless oil.

EXAMPLE 34

Alternate preparation of
d,l-erythro-9-oxo-11α,15,16-trihydroxy-5-cis,13-trans-prostadienoic acid and its 15-epimer To a stirred solution of 473 mg. (1.14 mmol.) of d,l-erythro-1-iodo-3,4-bis-trimethylsilyloxy-trans-1-octene (Example 33) in 6.0 ml. of dry ether at −78° C. under argon, is added 2.90 ml. of a 0.80 M solution of t-butyl lithium (2.40 mmol.) and stirring at −78° C. is continued for two hours. A solution of 123 mg. (1.14 mmol.) of thiophenol in 3.0 ml. of ether, under an argon atmosphere, is then treated with 0.50 ml. (1.14 mmol.) of a 2.30 M solution of n-butyllithium in pentane, by dropwise addition at 0° C., and the mixture is stirred for 15 minutes. Then a solution of 450 mg. (1.14 mmol.) of tri-n-butylphosphine copper (I)-iodide complex in 6.0 ml. of ether is added dropwise to the lithium thiophenoxide solution at −78° C. The resulting mixture is stirred a further 15 minutes, added slowly to the vinyllithium solution, and the whole is stirred for 45 minutes at −78° C. A solution of 420 mg. (1.14 mmol.) of 2-(6-carbotrimethylsilyloxy-2-cis-hexenyl)-4-trimethylsilyloxy-cyclopent-2-en-1-one (Example 31) in 5.0 ml. of ether is next added and stirring continued at −40° C. for two hours. The reaction is quenched at −40° C. with 135 mg. (2.28 mmol.) of acetic acid in 2.0 ml. of ether, poured into 30 ml. of a saturated ammonium chloride solution, extracted three times with 50 ml. of ether, the combined organic phases washed with 30 ml. of ammonium chloride solution, dried with magnesium sulfate, and evaporated under vacuum. The residue is stirred with a mixture of 15 ml. of acetic acid, 5 ml. of tetrahydrofuran, and 5 ml. of water for one hour at ambient temperature, taken to dryness and evaporated three times with 50 ml. of toluene at 50° C. (1.0 mm.) to remove thiophenol. The purified epimeric subject products are obtained by chromatography of the resulting oil following the method of Example 27.

EXAMPLE 35

Alternate preparation of d,l-erythro ethyl 9-oxo-15-hydroxy-16-methoxy-13-trans-prostenoate and its 15-epimer Conjugate addition of 1.07 g. (3.0 mmol.) of d,l-erythro-3-trimethylsilyloxy-4-methoxy-1-iodo-trans-1-octene (Example 19) to 715 mg. (3.0 mmol.) of 2-(6-carbethoxyhexyl)cyclopent-2-en-1-one by the procedure of Example 20, followed by acid hydrolysis using the conditions of Example 34, and chromatography after the method of Example 30 is productive of the epimeric subject products.

EXAMPLE 36

Preparation of d,l-erythro-3-trimethylsilyloxy-4-ethoxy-1-iodo-trans-1-octene

Following the procedure of Example 16, ethylation using iodoethane of d,l-erythro-3-tetrahydropyranyloxy-4-hydroxy-1-octyne for a period of 22 hours is productive of the corresponding d,l-erythro-3-tetrahydropyranyloxy-4-ethoxy-1-octyne. This intermediate is converted to d,l-erythro-3-tetrahydropyranyloxy-4-ethoxy-1-iodo-trans-1-octene when treated successively with disiamylborane, trimethylamine oxide, iodine, and sodium hydroxide solution after the procedure of Example 17. Acid hydrolysis by the method of Example 18 to d,l-erythro-3-hydroxy-4-ethoxy-1-iodo-trans-1-octene, followed by treatment with chlortrimethylsilane and imidazole in dimethylformamide using the procedure of Example 19, and subsequent distillation, is productive of the subject compound.

EXAMPLES 37-41

By the method of Example 3 reaction of 1-trimethylsilyl-3-tetrahydropyranyloxy-1-propyne with n-butyllithium and subsequent treatment with the aldehydes listed in Table I, below, provides the d,l-erythro-1-trimethylsilyl-3-tetrahydropyranyloxy-4-hydroxy-1-alkynes of the table.

Table 1

| Example | Starting Aldehyde | Product d,1-erythro-3-tetrahydropyranyloxy-4-hydroxy-1-trimethylsilyl-1-alkyne |
|---|---|---|
| 37 | n-butanal | d,1-erythro-1-trimethylsilyl-3-tetrahydropyranyloxy-4-hydroxy-1-heptyne |
| 38 | n-hexanal | d,1-erythro-1-trimethylsilyl-3-tetrahydropyranyloxy-4-hydroxy-1-nonyne |
| 39 | n-heptanal | d,1-erythro-1-trimethylsilyl-3-tetrahydropyranyloxy-4-hydroxy-1-decyne |
| 40 | 4-methyl-n-pentanal | d,1-erythro-1-trimethylsilyl-3-tetrahydropyranyloxy-4-hydroxy-7-methyl-1-octyne |
| 41 | 2-trans-n-pentenal | d,1-erythro-1-trimethylsilyl-3-tetrahydropyranyloxy-4-hydroxy-5-trans-en-1-octyne |

EXAMPLES 42-46

Hydrolysis of the 3-tetrahydropyranyloxy group of the d,l-erythro-1-trimethylsilyl-3-tetrahydropyranyloxy-4-hydroxy-1-alkynes listed in Table II below by the method described in Example 4, followed by conversion of the resulting d,l-erythro-1-trimethylsilyl-3,4-dihydroxy-1-alkyne to the corresponding d,l-erythro-1-trimethylsilyl-3,4-isopropylidenedioxy-1-alkyne by treatment with dimethoxypropane in the presence of perchloric acid by the method described in Example 5, followed by desilylation to the corresponding d,l-erythro-3,4-isiopropylidenedioxy-1-alkyne by the procedure of Example 6, followed by treatment with disiamylborane, trimethylamine oxide, iodine, and sodium hydroxide solution by the method described in Example 7, provides the product d,l-erythro-1-iodo-3,4-isopropylidenedioxy-trans-1-alkenes of Table II, below.

Table 2

| Example | Starting d,1-erythro-1-trimethylsilyl-3-tetrahydropyranyloxy-4-hydroxy-1-alkyne of Example | Product d,1-erythro-1-iodo-3,4-isopropylidenedioxy-trans-1-alkene |
|---|---|---|
| 42 | 37 | d,1-erythro-1-iodo-3,4-isopropylidenedioxy-trans-1-heptene |

Table 2-continued

| Example | Starting d,1-erythro-1-trimethyl-silyl-3-tetrahydropyranyloxy-4-hydroxy-1-alkyne of Example | Product d,1-erythro-1-iodo-3,4-isopropyl-lidenedioxy-trans-1-alkene |
|---|---|---|
| 43 | 38 | d,1-erythro-1-iodo-3,4-isopropylidenedioxy-trans-1-nonene |
| 44 | 39 | d,1-erythro-1-iodo-3,4-isopropylidenedioxy-trans-1 decene |
| 45 | 40 | d,1-erythro-1-iodo-3,4-isopropylidenedioxy-trans-1-7-methyl-1-octene |
| 46 | 41 | d,1-erythro-1-iodo-3,4-isopropylidenedioxy-trans-1-5-trans-1-octadiene |

EXAMPLES 47–82

Treatment of the cyclopentenones listed in Table III below with the pentynyl lithio cuprate prepared from the 1-iodo-trans-1-alkenyl derivative listed in Table III, by the procedure of Example 20, provides the corresponding alkyl-9-oxo-15,16-isopropylidenedioxy-13-trans-prostenoate which upon acid treatment following the method of Example 22 provides the corresponding 15,16-dihydroxy ester, which is then saponified by the procedure of Example 23 to give the product 9-oxo-15,16-dihydroxy-13-trans-prostenoic acid of Table III below. The 15-epimeric racemates can be separated from each other at the 15,16-isopropylidenedioxy stage, or preferably at the 15,16-dihydroxy ester stage as described in Example 22, or at the 15,16-dihydroxy-prostenoic acid stage. Subsequent saponification of the esters after Example 23 then provides the individual epimeric 15,16-dihydroxy prostenoic acids of the table.

Table III

| Example | Starting cyclopentenone | Starting 1-iodo-3,4-isopropylidenedioxy-trans-1-alkene of Example | Product 9-oxo-15,16-dihydroxy-13-trans-prostenoic acid and its 15-epimer |
|---|---|---|---|
| 47 | 2-(6-carbethoxyhexyl)-cyclopent-2-en-1-one | 14 | d,1-threo-9-oxo-15,16-dihydroxy-13-trans-prostenoic acid |
| 48 | 2-(6-carbethoxyhexyl)-cyclopent-2-en-1-one | 42 | d,1-erythro-9-oxo-15,16-dihydroxy-13-trans-20-nor-prostenoic acid |
| 49 | 2-(6-carbethoxyhexyl)-cyclopent-2-en-1-one | 43 | d,1-erythro-9-oxo-15,16-dihydroxy-13-trans-20-methyl-prostenoic acid |
| 50 | 2-(6-carbethoxyhexyl)-cyclopent-2-en-1-one | 44 | d,1-erythro-9-oxo-15,16-dihydroxy-13-trans-20-ethyl-prostenoic acid |
| 51 | 2-(6-carbethoxyhexyl)-cyclopent-2-en-1-one | 45 | d,1-erythro-9-oxo-15,16-dihydroxy-13-trans-19-methyl-prostenoic acid |
| 52 | 2-(6-carbethoxyhexyl)-cyclopent-2-en-1-one | 46 | d,1-erythro-9-oxo-15,16-dihydroxy-13-trans,17-trans-prostadienoic acid |
| 53 | 2-(6-carbethoxy-5-thiahexyl)-cyclopent-2-en-1-one[a] | 7 | d,1-erythro-9-oxo-15,16-dihydroxy-3-thia-13-trans-prostenoic acid |
| 54 | 2-(6-carbethoxy-5-thiahexyl)-cyclopent-2-en-1-one[a] | 14 | d,1-threo-9-oxo-15,16-dihydroxy-3-thia-13-trans-prostenoic acid |
| 55 | 2-(6-carbethoxy-5-thiahexyl)-cyclopent-2-en-1-one[a] | 42 | d,1-erythro-9-oxo-15,16-dihydroxy-3-thia-13-trans-20-nor-prostenoic acid |
| 56 | 2-(6-carbethoxy-5-thiahexyl)-cyclopent-2-en-1-one[a] | 45 | d,1-erythro-9-oxo-15,16-dihydroxy-3-thia-13-trans-19-methyl-prostenoic acid |
| 57 | 2-(6-carbethoxy-5-thiahexyl)-cyclopent-2-en-1-one[a] | 46 | d,1-erythro-9-oxo-15,16-dihydroxy-3-thia-13-trans,17-trans-prostadienoic acid |
| 58 | 2-(6-carbethoxy-5-oxahexyl)-cyclopent-2-en-1-one[a] | 7 | d,1-erythro-9-oxo-15,16-dihydroxy-3-oxa-13-trans-prostenoic acid |
| 59 | 2-(6-carbethoxy-5-oxahexyl)-cyclopent-2-en-1-one[a] | 14 | d,1-threo-9-oxo-15,16-dihydroxy-3-oxa-13-trans-prostenoic acid |
| 60 | 2-(6-carbethoxy-5-oxahexyl)-cyclopent-2-en-1-one[a] | 44 | d,1-erythro-9-oxa-15,16-dihydroxy-3-oxa-13-trans-20-ethyl-prostenoic acid |
| 61 | 2-(6-carbethoxy-5-oxahexyl)-cyclopent-2-en-1-one[a] | 46 | d,1-erythro-9-oxo-15,16-dihydroxy-3-oxa-13-trans,17-trans-prostadienoic acid |
| 62 | 2-(7-carbethoxy-6-thiaheptyl)-cyclopent-2-en-1-one (Ex. 414–416) | 7 | d,1-erythro-9-oxo-15,16-dihydroxy-3-thia-13-trans-7-homo-prostenoic acid |
| 63 | 2-(7-carbethoxy-6-thiaheptyl)-cyclopent-2-en-1-one (Ex. 414–416) | 14 | d,1-threo-9-oxo-15,16-dihydroxy-3-thia-13-trans-7-homo-prostenoic acid |
| 64 | 2-(7-carbethoxy-6-thiaheptyl)-cyclopent-2-en-1-one (Ex. 414–416) | 43 | d,1-erythro-9-oxo-15,16-dihydroxy-3-thia-13-trans-7-homo-20-methyl-prostenoic acid |
| 65 | 2-(7-carbethoxy-6-thiaheptyl)-cyclopent-2-en-1-one (Ex. 414–416) | 46 | d,1-erythro-9-oxo-15,16-dihydroxy-3-thia-13-trans,17-trans-prostadienoic acid |
| 66 | 2-(6-carbethoxy-2-cis-hexenyl)-cyclopent-2-en-1-one[b,c] | 7 | d,1-erythro-9-oxo-15,16-dihydroxy-5-cis,13-trans-prostadienoic acid |
| 67 | 2-(6-carbethoxy-2-cis-hexenyl)-cyclopent-2-en-1-one[b,c] | 14 | d,1-threo-9-oxo-15,16-dihydroxy-5-cis,13-trans-prostadienoic acid |
| 68 | 2-(6-carbethoxy-2-cis-hexenyl)-cyclopent-2-en-1-one[b,c] | 42 | d,1-erythro-9-oxo-15,16-dihydroxy-5-cis,13-trans-20-nor-prostadienoic acid |
| 69 | 2-(6-carbethoxy-2-cis-hexenyl)-cyclopent-2-en-1-one[b,c] | 43 | d,1-erythro-9-oxo-15,16-dihydroxy-5-cis,13-trans-20-methyl-prostadienoic acid |
| 70 | 2-(6-carbethoxy-2-cis-hexenyl)-cyclopent-2-en-1-one[b,c] | 44 | d,1-erythro-9-oxo-15,16-dihydroxy-5-cis,13-trans-20-ethyl-prostadienoic acid |
| 71 | 2-(6-carbethoxy-2-cis-hexenyl)-cyclopent-2-en-1-one[b,c] | 45 | d,1-erythro-9-oxo-15,16-dihydroxy-5-cis,13-trans-19-methyl-prostadienoic acid |

Table III-continued

| Example | Starting cyclopentenone | Starting 1-iodo-3,4-isopropylidenedioxy-trans-1-alkene of Example | Product 9-oxo-15,16-dihydroxy-13-trans-prostenoic acid and its 15-epimer |
|---|---|---|---|
| 72 | 2-(6-carbethoxy-2-cis-hexenyl)-cyclopent-2-en-1-one[b,c] | 46 | d,l-erythro-9-oxo-15,16-dihydroxy-5-cis,13-trans,17-trans-prostatrienoic acid |
| 73 | 2-(6-carbethoxy-5,6-methano-hexyl)-cyclopent-2-en-1-one (Ex. 417) | 7 | d,l-erythro-9-oxo-15,16-dihydroxy-2,3-methano-13-trans-prostenoic acid |
| 74 | 2-(6-carbethoxy-5,6-methano-hexyl)-cyclopent-2-en-1-one (Ex. 417) | 14 | d,l-threo-9-oxo-15,16-dihydroxy-2,3-methano-13-trans-prostenoic acid |
| 75 | 2-(6-carbethoxy-5,6-methano-hexyl)-cyclopent-2-en-1-one (Ex. 417) | 44 | d,l-erythro-9-oxo-15,16-dihydroxy-2,3-methano-13-trans-20-ethyl-prostenoic acid |
| 76 | 2-(6-carbethoxy-5,6-methano-hexyl)cyclopent-2-en-1-one (Ex. 417) | 46 | d,l-erythro-9-oxo-15,16-dihydroxy-2,3-methano-13-trans,17-trans-prostadienoic acid |
| 77 | 2-(7-carbethoxyheptyl)-cyclopent-2-en-1-one[a] | 7 | d,l-erythro-9-oxo-15,16-dihydroxy-13-trans-7-homo-prostenoic acid |
| 78 | 2-(7-carbethoxyheptyl)-cyclopent-2-en-1-one[a] | 14 | d,l-threo-9-oxo-15,16-dihydroxy-13-trans-7-homo-prostenoic acid |
| 79 | 2-(7-carbethoxyheptyl)-cyclopent-2-en-1-one[a] | 46 | d,l-erythro-9-oxo-15,16-dihydroxy-13-trans,17-trans-7-homo-prostadienoc acid |
| 80 | 2-(8-carbethoxyoctyl)-cyclopent-2-en-1-one[a] | 7 | d,l-erythro-9-oxo-15,16-dihydroxy-13-trans-7a,7b-bishomo-prostenoic acid |
| 81 | 2-(8-carbethoxyoctyl)-cyclopent-2-en-1-one[a] | 14 | d,l-threo-9-oxo-15,16-dihydroxy-13-trans,7a,7b-bishomo-prostenoic acid |
| 82 | 2-(8-carbethoxyoctyl)-cyclopent-2-en-1-one[a] | 46 | d,l-erythro-9-oxo-15,16-dihydroxy-13-trans,17-trans-7a,7b-bishomo-prostadienoic acid |

[a] K. F. Bernady, J. F. Poletto, M. J. Weiss, U.S. Pat. No. 3,836,581
[b] Netherlands Patent Spec. (7310-276) Derwent Central Patents Index, Farmdoc B-10735 V/06.
[c] P. A. Grieco and J. J. Reap, J. Org. Chem., 19, 3413 (1973).

EXAMPLES 83-119

Conjugate addition of the 4-tetrahydropyranyloxy-cyclopentenones listed in Table IV below with the lithium thiophenoxide cuprate prepared from the 1-iodo-trans-1-alkenyl derivatives listed in Table III, by the method of Example 34, provides the corresponding tetrahydropyranyl 9-oxo-11α-tetrahydropyranyloxy-15,16-isopropylidenedioxy-13-trans-prostenoates. The tetrahydropyranyl esters when treated by the acid hydrolysis conditions of Example 26 gives the 9-oxo-11α-tetrahydropyranyloxy-15,16-isopropylidenedioxy-13-trans-prostenoic acids of the table. The 15-epimeric racemates corresponding to the products listed in Table IV below may then be separated by careful chromatography as described in Example 27.

TABLE IV

| Example | Starting 4-tetrahydropyranyloxy cyclopentenone | Starting 1-iodo-3,4-isopropylidenedioxy-trans-1-alkene of Example | Product 9-oxo-11α-tetrahydropyranyloxy-15,16-isopropylidenedioxy-13-trans-prostenoic acid or ester and its 15-epimer |
|---|---|---|---|
| 83 | 2-(6-carbotetrahydropyranyloxy-hexyl)-4-tetrhydropyranyloxy-cyclopent-2-en-1-one | 7 | d,l-erythro-9-oxo-11α-tetrahydropyranyloxy-15,16-isopropylidenedioxy-13-trans-prostenoic acid |
| 84 | 2-(6-carbotetrahydropyranyloxy-hexyl)-4-tetrahydropyranyloxy-cyclopent-2-en-1-one | 14 | d,l-threo-9-oxo-11α-etrahydropyranyloxy-15,16-isopropylidenedioxy-13-trans-prostenoic acid |
| 85 | 2-(6-carbotetrahydropyranyloxy-hexyl)-4-tetrahydropyranyloxy-cyclopent-2-en-1-one | 42 | d,l-erythro-9-oxo-11α-tetrahydropyranyloxy-15,16-isopropylidenedioxy-13-trans-20-nor-prostenoic acid |
| 86 | 2-(6-carbotetrahydropyranyloxy-hexyl)-4-tetrahydropyranyloxy-cyclopent-2-en-1-one | 43 | d,l-erythro-9-oxo-11α-tetrahydropyranyloxy-15,16-isopropylidenedioxy-13-trans-20-methyl-prostenoic acid |
| 87 | 2-(6-carbotetrahydropyranyloxy-hexyl)-4-tetrahydropyranyloxy-cyclopent-2-en-1-one | 44 | d,l-erythro-9-oxo-11α-tetrahydropyranyloxy-15,16-isopropylidenedioxy-13-trans-20-ethyl-prostenoic acid |
| 88 | 2-(6-carbotetrahydropyranyloxy-hexyl)-4-tetrahydropyranyloxy-cyclopent-2-en-1-one | 45 | d,l-erythro-9-oxo-11α-tetrahydropyranyloxy-15,16-isopropylidenedioxy-13-trans-19-methyl-prostenoic acid |
| 89 | 2-(6-carbotetrahydropyranyloxy-hexyl)-4-tetrahydropyranyloxy-cyclopent-2-en-1-one | 46 | d,l-erythro-9-oxo-11α-tetrahydropyranyloxy-15,16-isopropylidenedioxy-13-trans,17-trans-prostadienoic acid |
| 90 | 2-(6-carbomethoxyhexyl)-(4R)-tetrahydropyranyloxy-cyclopent-2-en-1-one | 7 | l-erythro-methyl-9-oxo-11α-tetrahydropyranyloxy-15,16-isopropylidenedioxy-13-trans-prostenoate |
| 91 | 2-(6-carbomethoxyhexyl)-(4R)-tetrahydropyranyloxy-cyclopent-2-en-1-one | 14 | l-threo-methyl-9-oxo-11α-tetrahydropyranyloxy-15,16-isopropylidenedioxy-13-trans-prostenoate |
| 92 | 2-(6-carbomethoxyhexyl)-(4R)-tetrahydropyranyloxy-cyclopent-2-en-1-one | 46 | l-erythro-methyl-9-oxo-11α-tetrahydropyranyloxy-15,16-isopropylidenedioxy-13-trans,17-trans-prostadienoate |
| 93 | 2-(6-carbomethoxyhexyl)-(4S)-tetrahydropyranyloxy-cyclo- | 7 | d-erythro-methyl-9-oxo-11α-tetrahydropyranyloxy-15,16-isopropylidenedioxy-13-trans-prostenoate |

TABLE IV-continued

| Example | Starting 4-tetrahydropyranyloxy cyclopentenone | Starting 1-iodo-3,4-iso-propylidenedioxy-trans-1-alkene of Example | Product 9-oxo-11α-tetrahydropyranyloxy-15,16-isopropylidenedioxy-13-trans-prostenoic acid or ester and its 15-epimer |
|---|---|---|---|
| 94 | 2-(6-carbomethoxyhexyl)-(4S)-tetrahydropyranyloxy-cyclopent-2-en-1-one | 14 | d-threo-methyl-9-oxo-11α-tetrahydropyranyloxy-15,16-isopropylidenedioxy-13-trans-prostenoate |
| 94 | 2-(6-carbomethoxyhexyl)-(4S)-tetrahydropyranyloxy-cyclopent-2-en-1-one | 14 | d-threo-methyl-9-oxo-11α-tetrahydropyranyloxy-15,16-isopropylidenedioxy-13-trans-prostenoate |
| 95 | 2-(6-carbomethoxyhexyl)-(4S)-tetrahydropyranyloxy-cyclopent-2-en-1-one | 46 | d-erythro-methyl-9-oxo-11α-tetrahydropyranyloxy-15,16-isopropylidenedioxy-13-trans,17-trans-prostadienoate |
| 96 | 2-(6-carbotetrahydropyranyloxy-2-cis-hexenyl)-4-tetrahydropyranyloxy-cyclopent-2-en-1-one | 14 | d,l-threo-9-oxo-11α-tetrahydropyranyloxy-15,16-isopropylidenedioxy-5-cis,13-trans-prostadienoic acid |
| 97 | 2-(6-carbotetrahydropyranyloxy-2-cis-hexenyl)-4-tetrahydropyranyloxy-cyclopent-2-en-1-one | 42 | d,l-erythro-9-oxo-11α-tetrahydropyranyloxy-15,16-isopropylidenedioxy-5-cis,13-trans-20-nor-prostadienoic acid |
| 98 | 2-(6-carbotetrahydropyranyloxy-2-cis-hexenyl)-4-tetrahydropyranyloxy-cyclopent-2-en-1-one | 43 | d,l-erythro-9-oxo-11α-tetrahydropyranyloxy-15,16-isopropylidenedioxy-5-cis,13-trans-20-methyl-prostadienoic acid |
| 99 | 2-(6-carbotetrahydropyranyloxy-2-cis-hexenyl)-4-tetrahydropyranyloxy-cyclopent-2-en-1-one | 44 | d,l-erythro-9-oxo-11α-tetrahydropyranyloxy-15,16-isopropylidenedioxy-5-cis,13-trans-20-ethyl-acid |
| 100 | 2-(6-carbotetrahydropyranyloxy-2-cis-hexenyl)-4-tetrahydropyranyloxy-cyclopent-2-en-1-one | 45 | d,l-erythro-9-oxo-11α-tetrahydropyranyloxy-15,16-isopropylidenedioxy-5-cis,13-trans-19-methyl-prostadienoic acid |
| 101 | 2-(6-carbotetrahydropyranyloxy-2-cis-hexenyl)-4-tetrahydropyranyloxy-cyclopent-2-en-1-one | 46 | d,l-erythro-4-propyl-9-oxo-11α-tetrahydropyranyloxy-15,16-isopropylidenedioxy-5-cis,13-trans,17-trans-prostatrienoic acid |
| 102 | 2-(6-carbomethoxy-2-cis-hexenyl)-(4R)-tetrahydropyranyloxy-cyclopent-2-en-1-one | 7 | 1-erythro-methyl-9-oxo-11αd,1-threo-4-propyl-9-oxo-11α oxy-15,16-isopropylidenedioxy-5-cis,13-trans-prostadienoate |
| 103 | 2-(6-carbomethoxy-2-cis-hexenyl)-4(R)-tetrahydropyranyloxy-cyclopent-2-en-1-one | 14 | 1-threo-methyl-9-oxo-11α=2-(6-carbotetrahydrpyranyloxy-4-15,16-isopropylidenedioxy-cis,13-trans-prostadienoate |
| 104 | 2-(6-carbomethoxy-2-cis-hexenyl)-(4R)-tetrahydropyranyloxy-cyclopent-2-en-1-one | 46 | 1-erythro-methyl-9-oxo-11α-tetrahydropyranyloxy-15,16-isopropylidenedioxy-5-cis,13-trans,17-trans-prostatrienoate |
| 105 | 2-(6-carbotetrahydropyranyloxy-(4R)-methyl-2-cis-hexenyl)-4-tetrahydropyranyloxy-cyclopent-2-en-1-one | 7 | d,l-erythro-(4R)-methyl-9-oxo-11α-tetrahydropyranyloxy-15,16-isopropylidenedioxy-5-cis,13-d,l-erythro-4-ethyl-9-oxo-11αacid |
| 106 | 2-(6-carbotetrahydropyranyloxy-(4R)-methyl-2-cis-hexenyl)-4-tetrahydropyranyloxy-cyclopent-2-en-1-one | 14 | d,1-threo-(4R)-methyl-9-oxo-11α-tetrahydropyranyloxy-15,16-isopropylidenedioxy-5-cis,13-trans-prostadienoic acid |
| 107 | 2-(6-carbotetrahydropyranyloxy-(4R)-methyl-2-cis-hexenyl)-4-tetrahydropyranyloxy-cyclopent-2-en-1-one | 45 | d,l-erythro-(4R)-methyl-9-oxo-11α-tetrahydropyranyloxy-15,16-isopropylidenedioxy-5-cis,13-trans-19-methyl-prostadienoic acid |
| 108 | 2-(6-carbotetrahydropyranyloxy-(4R)-methyl-2-cis-hexenyl)-4-tetrahydropyranyloxy-cyclopent-2-en-1-one | 46 | d,l-erythro-(4R)-methyl-9-oxo-11α-tetrahydropyranyloxy-15,16-isopropylidenedioxy-5-cis,13-trans-, 17-trans-prostatrienoic acid |
| 109 | 2-(6-carbotetrahydropyranyloxy-4-propyl-2-cis-hexenyl)-4-tetrahydropyranyloxy-cyclopent-2-en-1-one | 7 | d,l-erythro-4-propyl-9-oxo-11α-tetrahydropyranyloxy-15,16-isopropylidenedioxy-5-cis,13-trans-prostadienoic acid |
| 110 | 2-(6-carbotetrahydropyranyloxy-4-propyl-2-cis-hexenyl)-4-tetrahydropyranyloxy-cyclopent-2-en-1-one | 14 | d,l-threo-4-propyl-9-oxo-11α-tetrahydropyranyloxy-15,16-isopropylidenedioxy-5-cis,13-trans-prostadienoic acid |
| 111 | 2-(6-cabotetrahydropyranyloxy-4-propyl-2-cis-hexenyl)-4-tetrahydropyranyloxy-cyclopent-2-en-1-one | 44 | d,l-erythro-4-propyl-9-oxo-11α-tetrahydropyranyloxy-15,16-isopropylidenedioxy-5-cis,13-trans-20-ethyl-prostadienoic acid |
| 112 | 2-(6-carbotetrahydropyranyloxy-4-propyl-2-cis-hexenyl)-4-tetrahydropyranyloxy-cyclopent-2-en-1-one | 46 | d,l-erythro-4-propyl-9-oxo-11α-tetrahydropyranyloxy-15,16-isopropylidenedioxy-5-cis,13-trans,17-trans-prostatrienoic acid |
| 113 | 2-(6-carbotetrahydropyranyloxy-4-ethyl-2-cis-hexenyl)-4-tetrahydropyranyloxy-cyclopent-2-en-1-one | 7 | d,l-erythro-4-ethyl-9-oxo-11α-tetrahydropyranyloxy-15,16-isopropylidenedioxy-5-cis,13-trans-prostadienoic acid |
| 114 | 2-(6-carbotetrahydropyranyloxy-4-ethyl-2-cis-hexenyl)-4-tetrahydropyranyloxy-cyclopent-2-en-1-one | 14 | d,l-threo-4-ethyl-9-oxo-11α-tetrahydropyranyloxy-15,16-isopropylidenedioxy-5-cis,13-trans-prostadienoic acid |
| 115 | 2-(6-carbotetrahydropyranyloxy-4-ethyl-2-cis-hexenyl)-4-tetra- | 43 | d,l-erythro-4-ethyl-9-oxo-11α-tetrahydropyranyloxy-15,16-isopropylidenedioxy-5-cis,13-trans-20- |

TABLE IV-continued

| Example | Starting 4-tetrahydropyranyloxy cyclopentenone | Starting 1-iodo-3,4-isopropylidenedioxy-trans-1-alkene of Example | Product 9-oxo-11α-tetrahydropyranyloxy-15,16-isopropylidenedioxy-13-trans-prostenoic acid or ester and its 15-epimer |
|---|---|---|---|
|  | hydropyranyloxy-cyclopent-2-en-1-one |  | methyl-prostadienoic acid |
| 116 | 2-(6-carbotetrahydropyranyloxy-4-ethyl-2-cis-hexenyl)-4-tetrahydropyranyloxy-cyclopent-2-en-1-one | 46 | d,l-erythro-4-ethyl-9-oxo-11α-tetrahydropyranyloxy-15,16-isopropylidenedioxy-5-cis,13-trans,17-trans-prostatrienoic acid |
| 117 | 2-(8-carbotetrahydropyranyloxy-octyl)-4-tetrahydropyranyloxy-cyclopent-2-en-1-one | 7 | d,l-erythro-4-ethyl-9-oxo-11α-tetrahydropyranyloxy-oxy-15,16-isopropylidenedioxy-13-trans-7a,7b-bishomo-prostenoic acid |
| 118 | 2-(8-carbotetrahydropyranyloxy-octyl)-4-tetrahydropyranyloxy-cyclopent-2-en-1-one | 14 | d,l-threo-9-oxo-11α-tetrahydropyranyloxy-15,16-isopropylidenedioxy-13-trans-7a,7b-bishomo-prostenoic acid |
| 119 | 2-(8-carbotetrahydropyranyloxy-octyl)-4-tetrahydropyranyloxy cyclopent-2-en-1-one | 46 | d,l-erythro-9-oxo-11α-tetrahydropyranyloxy-15,16-isopropylidenedioxy-13-trans,17-trans-7a,7b-bishomo-prostadienoic acid |

EXAMPLES 120–156

Acid hydrolysis of the individual 9-oxo-11α-tetrahydropyranyloxy-15,16-isopropylidenedioxy-prostenoic acids or esters and their 15-epimeric racemates, of Table IV using the procedure of Example 27, affords the corresponding 11α-hydroxy-15,16-isopropylidenedioxy-prostenoic acids, which may then be isolated at this stage. If hydrolysis is continued as in Example 28, the fully deblocked 9-oxo-11α,15,16-trihydroxy-prostenoic acid or ester and its 15-epimer of Table V below, is obtained.

Table V

| Example | Starting 9-oxo-11-tetrahydropyranyloxy-15,16-isopropylidenedioxy-13-trans-prostenoic acid or ester and its 15-epimer of Example | Product 9-oxo-11α-15,16-trihydroxy-13-trans-prostenoic acid or ester and its 15-epimeric racemate |
|---|---|---|
| 120 | 83 | d,l-erthro-9-oxo-11α,15,16-trihydroxy-13-trans-prostenoic acid |
| 121 | 84 | d,l-threo-9-oxo-11α,15,16-trihydroxy-13-trans-prostenoic acid |
| 122 | 85 | d,l-erythro-9-oxo-11α,15,16-trihydroxy-13-trans-20-nor-prostenoic acid |
| 123 | 86 | d,l-erythro-9-oxo-11α,15,16-trihydroxy-13-trans-20-methyl-prostenoic acid |
| 124 | 87 | d,l-erythro-9-oxo-11α,15,16-trihydroxy-13-trans-20-methyl-prostenoic acid |
| 125 | 88 | d,l-erythro-9-oxo-11α,15,16-trihydroxy-13-trans-19-methyl-prostenoic acid |
| 126 | 89 | d,l-erythro-9-oxo-11α,15,16-trihydroxy-13-trans,17-trans-prostenoic acid |
| 127 | 90 | l-erythro-methyl-9-oxo-11α,15,16-trihydroxy-13-trans-prostenoate |
| 128 | 91 | l-threo-methyl-9-oxo-11α,15,15-trihydroxy-13-trans-prostenoate |
| 129 | 92 | l-erythro-methyl-9-oxo-11α,15,16-trihydroxy-13-trans,17-trans-prostadienoate |
| 130 | 93 | d-erythro-methyl-9-oxo-11α,15,16-trihydroxy-13-trans-prostenoate |
| 131 | 94 | d-threo-methyl-9-oxo-11α,15,16-trihydroxy-13-trans-prostenoate |
| 132 | 95 | d-erythro-methyl-9-oxo-11α,15,16-trihydroxy-13-trans,17-trans-prostadienoate |
| 133 | 96 | d,l-threo-9-oxo-11α,15,16-trihydroxy-5-cis,13-trans-prostadienoic acid |
| 134 | 97 | d,l-erythro-9-oxo-11α,15,16-trihydroxy-5-cis,13-trans-20-nor-prostadienoic acid |
| 135 | 98 | d,l-erythro-9-oxo-11α,15,16-trihydroxy-5-cis,13-trans-20-methyl-prostadienoic acid |
| 136 | 99 | d,l-erythro-9-oxo-11α,15,16-trihydroxy-5-cis,13-trans-20-ethyl-prostadienoic acid |
| 137 | 100 | d,l-erythro-9-oxo-11α,15,16-trihydroxy-5-cis,13-trans-19-methyl-prostadienoic acid |
| 138 | 101 | d,l-erythro-9-oxo-11α60,15,16-trihydroxy-5-cis,13-trans,17-trans-prostatrienoic acid |
| 139 | 102 | l-erythro-methyl-9-oxo-11α,15,16-trihydroxy-5-cis,13-trans-prostadienoate |
| 140 | 103 | l-threo-methyl-9-oxo-11α,15,16-trihydroxy-5-cis,13-trans-prostadienoate |
| 141 | 104 | l-erythro-methyl-9-oxo-11α,15,16-trihydroxy-5-cis,13-trans,17-trans-prostatrienoate |
| 142 | 105 | d,l-erythro-(4R)-methyl-9-oxo-11α,15,16-trihydroxy-5-cis,13-trans-prostadienoic acid |
| 143 | 106 | d,l-threo-(4R)-methyl-9-oxo-11αd,l-threo-(4R)-methyl-9-oxo-11α trans-prostadienoic acid |
| 144 | 107 | d,l-erythro-(4R)-methyl-9-oxo-11α,15,16-trihydroxy-5-cis,13-trans-19-methyl-prostadienoic acid |
| 145 | 108 | d,l-erythro-(4R)-methyl-9-oxo-11α,15,16-trihydroxy-5-cis,13-trans,17-trans-prostatrienoic acid |

Table V-continued

| Example | Starting 9-oxo-11-tetrahydropyranyloxy-15,16-isopropylidenedioxy-13-trans-prostenoic acid or ester and its 15-epimer of Example | Product 9-oxo-11α-15,16-trihydroxy-13-trans-prostenoic acid or ester and its 15-epimeric racemate |
|---|---|---|
| 146 | 109 | d,1-erythro-4-propyl-9-oxo-11α,15,16-trihydroxy-5-cis,13-trans-prostadienoic acid |
| 147 | 110 | d,1-threo-4-propyl-9-oxo-11α,15,16-trihydroxy-5-cis,13-trans-prostadienoic acid |
| 148 | 111 | d,1-erythro-4-propyl-9-oxo-11α,15,16-trihydroxy-5-cis,13-trans,20-ethyl-prostadienoic acid |
| 149 | 112 | d,1-erythro-4-propyl-9-oxo-11α,15,16-trihydroxy-5-cis,13-trans,17-trasn-prostatrienoic acid |
| 150 | 113 | d,1-erythro-4-ethyl-9-oxo-11α,15,16-trihydroxy-5-cis,13-trans-prostadienoic acid |
| 151 | 114 | d,1-threo-4-ethyl-9-oxo-11α,15,16-trihydroxy-5-cis,13-trans-prostadienoic acid |
| 152 | 115 | d,1-erythro-4-ethyl-9-oxo-11α,15,16-trihydroxy-5-cis,13-trans-20-methyl-prostadienoic acid |
| 153 | 116 | d,1-erythro-4-ethyl-9-oxo-11α,15,16-trihydroxy-5-cis,13-trans,17-trans-prostatrienoic acid |
| 154 | 117 | d,1-erythro-9-oxo-11α,15,16-trihydroxy-13-trans-7a,7b-bishomo-prostenoic acid |
| 155 | 118 | d,1-threo-9-oxo-11α,15,16-trihydroxy-13-trans-7a,7b-bishomo-prostenoic acid |
| 156 | 119 | d,1-erhtyro-9-oxo-11α,15,16-trihydroxy-13-trans,17-trans-7a,7b-bishomo-prostadienoic acid |

EXAMPLES 157–167

Treatment of the 2-(carbethoxyalkyl)cyclopentenones listed in Table VI below with the pentynyl lithio cuprate prepared from the d,l-erythro-3-trimethylsilyloxy-4-methoxy or ethoxy-1-iodo-trans-1-octenes of Examples 19 and 36 respectively by the procedure of Example 35, provides the corresponding ethyl 9-oxo-15-hydroxy-16-methoxy or ethoxy-13-trans-prostenoate and its 15-epimeric racemate. These can be separated at this stage or after saponification, following the procedure of Example 23, to the 9-oxo-15-hydroxy-16-methoxy or ethoxy-13-trans-prostenoic acids listed in Table VI below.

lithio cuprate prepared from the 3-trimethylsilyloxy-4-alkoxy-1-iodo-trans-1-octenes of Examples 19 and 36 by the procedure of Examples 35 gives the corresponding tetrahydropyranyloxy-9-oxo-11α-tetrahydropyranyloxy-15-trimethylsilyloxy-16-alkoxy-13-trans-prostenoate. These when subjected to the hydrolytic conditions of Example 34, provide the partially deblocked 9-oxo-11α-tetrahydropyranyloxy-15-hydroxy-16-alkoxy-13-trans-prostenoic acids or ester and their 15-epimeric racemates, which may then be chromatographically separated after the method of Example 27. The 11α-tetrahydropyranyloxy-prostenoic acids or esters when treated further with acid following the procedure of Example 27, and with subsequent Table VI

| Example | Starting 2-(Carbethoxyalkyl)cyclopentenone of Example | Starting 3-trimethylsilyloxy-4-alkoxy-1-iodo-trans-1-octene of Example | Product 9-oxo-15-hydroxy-16-alkoxy-13-trans-prostenoic acid and its 15-epimer |
|---|---|---|---|
| 157 | 47 | 19 | d,1-erythro-9-oxo-15-hydroxy-16-methoxy-13-trans-prostenoic acid |
| 158 | 47 | 36 | d,1-erythro-9-oxo-15-hydroxy-16-ethoxy-13-trans-prostenoic acid |
| 159 | 53 | 19 | d,1-erythro-9-oxo-15-hydroxy-16-methoxy-3-thia-13-trans-prostenoic acid |
| 160 | 53 | 36 | d,1-erythro-9-oxo-15-hydroxy-16-ethoxy-3-thia-13-trans-prostenoic acid |
| 161 | 58 | 19 | d,1-erythro-9-oxo-15-hydroxy-16-methoxy-3-oxa-13-trans-prostenoic acid |
| 162 | 62 | 19 | d,1-erythro-9-oxo-15-hydroxy-16-methoxy-3-thia-13-trans-7-homo-prostenoic acid |
| 163 | 66 | 19 | d,1-erythro-9-oxo-15-hydroxy-16-methoxy-5-cis,13-trans-prostadienoic acid |
| 164 | 66 | 36 | d,1-erythro-9-oxo-15-hydroxy-16-ethoxy-5-cis,13-trans-prostadienoic acid |
| 165 | 73 | 19 | d,1-erythro-9-oxo-15-hydroxy-16-methoxy-2,3-methano-13-trans-prostenoic acid |
| 166 | 77 | 19 | d,1-erythro-9-oxo-15-hydroxy-16-methoxy-13-trans-7-homo-prostenoic acid |
| 167 | 80 | 19 | d,1-erythro-9-oxo-15-hydroxy-16-methoxy-13-trans-7a,7b-bishomo-prostenoic acid |

EXAMPLES 168–178

Conjugate addition of the 4-tetrahydropyranyloxycyclopentenones of Table VII below with the pentynyl chromatography to separate the 15-epimeric racemates give the 9-oxo-11α,15-dihydroxy-16-alkoxy-13-trans-prostenoic acids or esters and their 15-epimeric racemates of Table VII below.

TABLE VII

| Example | Starting 4-tetrahydro pyranyloxy cyclopentenone of Example | Starting 3-trimethyl-silyloxy-4-alkoxy-1-iodo-trans-1-octene of Example | Product 9-oxo-11α,15-dihydroxy-16-alkoxy-13-trans-prostenoic acid or ester and its 15-epimer |
|---|---|---|---|
| 168 | 83 | 19 | d,l-erythro-9-oxo-11α,15-dihydroxy-16-methoxy-13-trans-prostenoic acid |
| 169 | 83 | 36 | d,l-erythro-9-oxo-11α,15-dihydroxy-16-ethoxy-13-trans-prostenoic acid |
| 170 | 90 | 19 | l-erythro-methyl-9-oxo-11α,15-dihydroxy-16-methoxy-13-trans-prostenoate |
| 171 | 93 | 19 | d-erythro-methyl-9-oxo-11α,15-dihydroxy-16-methoxy-13-trans-prostenoate |
| 172 | 96 | 19 | d,l-erythro-9-oxo-11α,15-dihydroxy-16-methoxy-5-cis,13-trans-prostadienoic acid |
| 173 | 96 | 36 | d,l-erythro-9-oxo-11α,15-dihydroxy-16-ethoxy-5-cis,13-trans-prostadienoic acid |
| 174 | 102 | 19 | l-erythro-methyl-9-oxo-11α,15-dihydroxy-16-methoxy-5-cis,13-trans-prostadienoate |
| 75 | 105 | 19 | d,l-erythro-(4R)-methyl-9-oxo-11α,15-dihydroxy-16-methoxy-5-cis,13-trans-prostadienoic acid |
| 176 | 109 | 19 | d,l-erythro-4-propyl-9-oxo-11α,15-dihydroxy-16-methoxy-5-cis,13-trans-prostadienoic acid |
| 177 | 113 | 19 | d,l-erythro-4-ethyl-9-oxo-11α,15-dihydroxy-16-methoxy-5-cis,13-trans-prostadienoic acid |
| 178 | 117 | 19 | d,l-erythro-9-oxo-11α,15-dihydroxy-16-methoxy-13-trans-7a,7b-bishomo-prostenoic acid |

EXAMPLE 179

Preparation of
dl-erythro-9-oxo-15,16-dihydroxy-5-cis,10,13-trans-prostatrienoic acid and dl-erythro-9-oxo-15-epi, 16-dihydroxy-5-cis,10,13-trans-prostatrienoic acid A solution of 50 mg. (0.142 mmol.) of dl-erythro-9-oxo-11α,15,16-trihydroxy-5-cis,13-trans-prostatrienoic acid (Example 34) in 1.0 ml. of 1.5 N hydrochloric acid and 2.0 ml. of tetrahydrofuran under an argon atmosphere is stirred at ambient temperature for 70 hours. The solution is then diluted with 5.0 ml. of saturated sodium chloride solution, extracted with three 5.0 ml. portions of ether, the combined organic phases dried with magnesium sulfate, and evaporated under vacuum, to give the crude 15-normal product. This is purified on a silica gel glass plate by thin layer chromatography, and eluted with a solution of ethyl acetate containing 1.0% ethanol and 1.0% of acetic acid, to give 40 mg. of the 15-normal subject product as a yellow oil. Treatment of 50 mg. of dl-erythro-9-oxo-11α,15-epi,16-trihydroxy-5-cis,13-trans-prostatrienoic acid (Example 34) in the same manner as above, is productive of the 15-epi racemic subject product.

EXAMPLES 180–223

Following the procedure of Example 179, treatment of the 9-oxo-11α,15,16-trihydroxy-or 11α,15-dihydroxy-16-alkoxy-13-trans-prostenoic acids or esters of Table IX below with 1.5 N hydrochloric acid in tetrahydrofuran for 70 hours is productive of the corresponding product 9-oxo-15,16-dihydroxy or 15-hydroxy-16-alkoxy-10,13-trans-prostenoic acids or ester of the table.

TABLE VIII

| Example | Starting 9-oxo-11α,15,16-trihydroxy or 11α,15-dihydroxy-16-alkoxy-13-trans-prostenoic acids or esters of Example | Product 9-oxo-15,16-dihydroxy- or 15-hydroxy-16-alkoxy-10,13-trans-prostenoic acid or ester |
|---|---|---|
| 180 | 120 | dl-erythro-9-oxo-15,16-dihydroxy-10,13-trans-prostadienoic acid |
| 181 | 121 | dl-threo-9-oxo-15,16-dihydroxy-10,13-trans-prostadienoic acid |
| 182 | 122 | dl-erythro-9-oxo-15,16-dihydroxy-10,13-trans-20-nor-prostadienoic acid |
| 183 | 123 | dl-erythro-15,16-dihydroxy-10,13-trans-20-methyl-prostadienoic acid |
| 184 | 124 | dl-erythro-9-oxo-15,16-dihydroxy-10,13-trans-20-ethyl-prostadienoic acid |
| 185 | 125 | dl-erythro-9-oxo-15,16-dihydroxy-10,13-trans-19-methyl-prostadienoic acid |
| 186 | 126 | dl-erythro-9-oxo-15,16-dihydroxy-10,13-trans,17-trans-prostatrienoic acid |
| 187 | 127 | l-erythro-methyl-9-oxo-15,16-dihydroxy-10,13-trans-prostadienoate |
| 188 | 128 | l-threo-methyl-9-oxo-15,16-dihydroxy-10,13-trans-prostadienoate |
| 189 | 129 | l-erythro-methyl-9-oxo-15,16-dihydroxy-10,13-trans,17-trans-prostatrienoate |
| 190 | 133 | dl-threo-9-oxo-15,16-dihydroxy-5-cis,10,13-trans-prostatrienoic acid |
| 191 | 134 | dl-erythro-9-oxo-15,16-dihydroxy-5-cis,10,13-trans-20-nor-prostatrienoic acid |
| 192 | 135 | dl-erythro-9-oxo-15,16-dihydroxy-5-cis,10,13-trans-20-methyl-prostatrienoic acid |

TABLE VIII-continued

| Example | Starting 9-oxo-11α,15,16-trihydroxy or 11α,15-dihydroxy-16-alkoxy-13-trans-prostenoic acids or esters of Example | Product 9-oxo-15,16-dihydroxy- or 15-hydroxy-16-alkoxy-10,13-trans-prostenoic acid or ester |
|---|---|---|
| 193 | 136 | el-erythro-9-oxo-15,16-dihydroxy-5-cis,10,13-trans-20-ethyl-prostatrienoic acid |
| 194 | 137 | dl-erythro-9-oxo-15,16-dihydroxy-5-cis,10,13-trans-19-methyl-prostatrienoic acid |
| 195 | 138 | dl-erythro-9-oxo-15,16-dihydroxy-5-cis,10,13-trans,10,13-trans,17-trans-prostatetraenoic acid |
| 196 | 139 | l-erythro-methyl-9-oxo-15,16-dihydroxy-5-cis,10,13-trans-prostatrienoate |
| 197 | 140 | l-threo-methyl-9-oxo-15,16-dihydroxy-5-cis,10,13-trans-prostatrienoate |
| 198 | 141 | l-erythro-methyl-9-oxo-15,16-dihydroxy-5-cis,10,13-trans,17-trans-prostatetraenoate |
| 199 | 142 | dl-erythro-(4R)-methyl-9-oxo-15,16-dihydroxy-5-cis,10,13-trans-prostatrienoic acid |
| 200 | 143 | dl-threo-(4R)-methyl-9-oxo-15,16-dihydroxy-5-cis,10,13-trans-prostatrienoic acid |
| 201 | 144 | dl-erythro-(4R)-methyl-9-oxo-15,16-dihydroxy-5-cis,10,13-trans-19-methyl-prostatrienoic acid |
| 202 | 145 | dl-erythro-(4R)-methyl-9-oxo-15,16-dihydroxy-5-cis,10,13-trans,17-trans-prostatetraenoic acid |
| 203 | 146 | dl-erythro-4-propyl-9-oxo-15,16-dihydroxy-5-cis,10,13-trans-prostatrienoic acid |
| 204 | 147 | dl-threo-4-propyl-9-oxo-15,16-dihydroxy-5-cis,10,13-trans-prostatrienoic acid |
| 205 | 148 | dl-erythro-4-propyl-9-oxo-15,16-dihydroxy-5-cis,10,13-trans-20-ethyl-prostatrienoic acid |
| 206 | 149 | dl-erythro-propyl-9-oxo-15,16-dihydroxy-5-cis,10,13-trans,17-trans-prostatetraenoic acid |
| 207 | 150 | dl-erythro-4-ethyl-9-oxo-15,16-dihydroxy-5-cis,10,13-trans-prostatrienoic acid |
| 208 | 151 | dl-threo-4-ethyl-9-oxo-15,16-dihydroxy-5-cis,10,13-trans-prostatrienoic acid |
| 209 | 152 | dl-erythro-4-ethyl-9-oxo-15,16-dihydroxy-5-cis,10,13-trans-20-methyl-prostatrienoic acid |
| 210 | 153 | dl-erythro-4-ethyl-9-oxo-15,16-dihydroxy-5-cis,10,13-trans,17-trans-prostatetraenoic acid |
| 211 | 154 | dl-erythro-9-oxo-15,16-dihydroxy-10,13-trans-7a,7b-bishomo-prostadienoic acid |
| 212 | 155 | dl-threo-9-oxo-15,16-dihydroxy-10,13-trans-7a,7b-bishomo-prostadienoic acid |
| 213 | 156 | dl-erythro-9-oxo-15,16-dihydroxy-10,13-trans,17-trans-7a,7b-bishomo-prostatrienoic acid |
| 214 | 168 | dl-erythro-9-oxo-15-hydroxy-16-methoxy-10,13-trans-prostadienoic acid |
| 215 | 169 | dl-erythro-9-oxo-15-hydroxy-16-ethoxy-10,13-trans-prostadienoic acid |
| 216 | 170 | l-erythro-methyl-9-oxo-15-hydroxy-16-methoxy-10,13-trans-prostadienoate |
| 217 | 172 | dl-erythro-9-oxo-15-hydroxy-16-methoxy-5-cis,10,13-trans-prostatrienoic acid |
| 218 | 173 | dl-erythro-9-oxo-15-hydroxy-16-ethoxy-5-cis,10,13-trans-prostatrienoic acid |
| 219 | 174 | l-erythro-methyl-9-oxo-15-hydroxy-16-methoxy-5-cis,10,13-trans-prostatrienoate |
| 220 | 175 | dl-erythro-(4R)-methyl-9-oxo-15-hydroxy-16-methoxy-5-cis,10,13-trans-prostatrienoic acid |
| 221 | 176 | dl-erythro-4-propyl-9-oxo-15-hydroxy-16-methoxy-5-cis,10,13-trans-prostatrienoic acid |
| 222 | 177 | dl-erythro-4-ethyl-9-oxo-15-hydroxy-16-methoxy-5-cis,10,13-trans-prostatrienoic acid |
| 223 | 178 | dl-erythro-9-oxo-15-hydroxy-16-methyl-10,13-trans-7a,7b-bishomo-prostadienoic acid |

EXAMPLE 224

Preparation of dl-erythro-9-oxo-15,16-dihydroxy-5-cis,8,13-trans-prostatrienoic acid and its 15-epimeric racemate A solution of 11.0 mg. (0.0299 mmol.) of dl-erythro-9-oxo-11α,15,16-trihydroxy-5-cis,13-trans-prostadienoic acid (Example 34) in 4.0 ml. of 95% ethanol and 4.0 ml. of 1.0 N sodium hydroxide solution is stirred at 40° C., under an argon atmosphere, for two hours. It is then cooled, concentrated under vacuum to remove ethanol, acidified with 5.0 ml. of 1.0 N hydrochloric acid, extracted twice with 20 ml. of ethyl ether, washed with 10 ml. of brine solution, dried with magnesium sulfate, filtered, and evaporated, to give the subject product as a yellow oil. Treatment of dl-erythro-9-oxo-11α,15-epi-16-trihydroxy-5-cis,13-trans-prostadienoic acid by the same procedure procedure is productive of the 15-epimeric subject product racemate. Both compounds may be purified on a 3.0 g. dry column of silica gel and eluted with a solution of 1.0% acetic acid in ethyl acetate.

EXAMPLES 225-238

By the procedure described in Example 224, treatment of the various 9-oxo-11α,15,16-trihydroxy or 11α,15-dihydroxy-16-alkoxy-13-trans-prostenoic acids or esters and their 15-epimers with sodium hydroxide in ethanol, is productive of the 9-oxo-15,16-dihydroxy or 15-hydroxy-16-alkoxy-8,13-trans-prostenoic acids or esters and their 15-epimeric racemates of Table IX, below.

give the 9α and 9β-hydroxy subject racemates. These are separated on a 1.0 in. ×36 in. dry column of silica gel and eluted with a solution of 1% ethanol and 1% acetic acid in ethyl acetate affording the separated racemates as viscous colorless oils. In the same manner, reduction of dl-erythro-9-oxo-11α,15-epi, 16-trihydroxy-5-cis,13-trans-prostadienoic acid (Example 34) with sodium borohydride in ethanol is productive of both dl-erythro-9α and 9β,11,15-epi,16-tetrahydroxy-5-cis,13-trans-prostadienoic acid subject tacemates which are also

TABLE IX

| Example | 9-oxo-11α,15,16-trihydroxy- or 11α,15-dihydroxy-16-alkoxy-13-trans-prostenoic acid or ester and its 15-epimer of Example | Product 9-oxo-15,16-dihydroxy or 15-hydroxy-16-alkoxy-8,13-trans-prostenoic acid or ester and its 15-epimeric racemate |
|---|---|---|
| 225 | 120 | dl-erythro-9-oxo-15,16-dihydroxy-9,13-trans-prostadienoic acid |
| 226 | 121 | dl-threo-9-oxo-15,16-dihydroxy-8,13-trans,17-trans-prosta- acid |
| 227 | 126 | dl-erythro-9-oxo-15,16-dihydroxy-8,13-trans,17-trans-prostatrienoic acid |
| 228 | 133 | dl-threo-9-oxo-15,16-dihydroxy-5-cis,8,13-trans-prostatrienoic acid |
| 229 | 138 | dl-erythro-9-oxo-15,16-dihydroxy-5-cis,8,13-trans,17-trans-prostatetraenoic acid |
| 230 | 142 | dl-erythro-4(R)-methyl-9-oxo-15,16-dihydroxy-5-cis,8,13-trans-prostatrienoic acid |
| 231 | 154 | dl-erythro-9-oxo-15,16-dihydroxy-8,13-trans-7a,7b-bishomo-prostadienoic acid |
| 232 | 155 | dl-threo-9-oxo-15,16-dihydroxy-8,13-trans-7a,7b-bishomo-prostadienoi acid |
| 233 | 156 | dl-erythro-9-oxo-15,16-dihydroxy-8,13-trans,17-trans-7a,7b-bishomo-prostatrienoic acid |
| 234 | 168 | dl-erythro-9-oxo-15-hydroxy-16-methoxy-8,13-trans-prostadienoic acid |
| 235 | 169 | dl-erythro-9-oxo-15-hydroxy-16-ethoxy-8,13-trans-prostadienoic acid |
| 236 | 172 | dl-erythro-9-oxo-15-hydroxy-16-methoxy-5-cis,8,13-trans-prostatrienoic acid |
| 237 | 175 | dl-erythro-4(R)-methyl-9-oxo-15-hydroxy-16-methoxy-5-cis,8,13-trans-prostatrienoic acid |
| 238 | 178 | dl-erythro-9-oxo-15-hydroxy-16-methoxy-8,13-trans-7a,7b-bishomo-prostadienoic acid |

EXAMPLE 239

Preparation of dl-erythro-9α,11α,15,16-tetrahydroxy-5-cis,13-trans-prostadienoic acid and dl-erythro-9β,11β,15,16-tetrahydroxy-5-cis,13-trans-prostadienoic acid and their 15-epimeric racemates To a solution of 500 mg. (1.35 mmol.) of dl-erythro-9-oxo-11α,15,16-trihydroxy-5-cis,13-trans-prostadienoic acid (Example 34) in 10.0 ml. of 95% ethanol is added portionwise with stirring 400 mg. (10.6 mmol.) of sodium borohydride. The mixture is stirred for one hour, poured into 10 ml. of water acidified with hydrochloric acid, extracted twice with 20 ml. each of ethyl ether, the combined organic layers washed with 5 ml. of a saturated solution of sodium chloride, dryed with magnesium sulfate, filtered, and evaporated under vacuum to separated according to the above procedure.

EXAMPLES 240-335

In Table X below, treatment of the listed 9-oxo-15,16-dihydroxy-13-trans-prostenoic acids, or 9-oxo-11α,15,16-trihydroxy-13-trans-prostenoic acids and esters, or 9-oxo-15-hydroxy-16-alkoxy-13-trans-prostenoic acids, or 9-oxo-11α,15-dihydroxy-16-alkoxy-13-trans-prostenoic acids and esters with sodium borohydride in ethanol, using the procedure of Example 239, with subsequent separation of the 9α and 9β racemates, is productive of the corresponding 9α or 9β-hydroxy-prostenoic acids or esters of the table. Only the 9α-hydroxy racemate example is listed in Table X. Similar treatment of the corresponding 15-epimeric starting 9-ones of the table gives the corresponding 15-epimeric 9α-ol and 9β-ols.

TABLE X

| Example | Starting 9-oxo-prostenoic acids or esters of Example | Product 9α-hydroxy substituted prostenoic acids or esters and the corresponding 9β-ol |
|---|---|---|
| 240 | 23 | dl-erythro-9α,15,16-trihydroxy-13-trans-prostenoic acid |
| 241 | 47 | dl-threo-9α,15,16-trihydroxy-13-trans-prostenoic acid |
| 242 | 48 | dl-erythro-9α,15,16-trihydroxy-13-trans-20-nor-prostenoic acid |
| 243 | 49 | dl-erythro-9α,15,16-trihydroxy-13-trans-20-methyl-prostenoic acid |
| 244 | 50 | dl-erythro-9α,15,16-trihydroxy-13-trans-20-ethyl-prostenoic acid |
| 245 | 51 | dl-erythro-9α,15,16-trihydroxy-13-trans-19-methyl-prostenoic acid |
| 246 | 52 | dl-erythro-9α,15,16-trihydroxy-13-trans,17-trans-prostadienoic |

TABLE X-continued

| Example | Starting 9-oxo-prostenoic acids or esters of Example | Product 9α-hydroxy substituted prostenoic acids or esters and the corresponding 9β-ol |
|---|---|---|
| | | acid |
| 247 | 53 | dl-erythro-9α,15,16-trihydroxy-13-thia-13-trans-prostenoic acid |
| 248 | 54 | dl-threo-9α,15,16-trihydroxy-3-thia-13-trans-prostenoic acid |
| 249 | 55 | dl-erythro-9α,15,16-trihydroxy-3-thia-13-trans-20-nor-prostenoic acid |
| 250 | 56 | dl-erythro-9α,15,16-trihydroxy-3-thia-13-trans-19-methyl-prostenoic acid |
| 251 | 57 | dl-erythro-9α,15,16-trihydroxy-3-thia-13-trans,17-trans-prostadienoic acid |
| 252 | 58 | dl-erythro-9α,15,16-trihydroxy-3-oxa-13-trans-prostenoic acid |
| 253 | 59 | dl-threo-9α,15,16-trihydroxy-3-oxa-13-trans-prostenoic acid |
| 254 | 60 | dl-erythro-9α,15,16-trihydroxy-3-oxa-13-trans-20-ethyl-prostenoic acid |
| 255 | 61 | dl-erythro-9α,15,16-trihydroxy-3-oxa-13-trans,17-trans-prostadienoic acid |
| 256 | 62 | dl-erythro-9α,15,16-trihydroxy-3-thia-13-trans-7-homo-prostenoic acid |
| 257 | 63 | dl-threo-9α,15,16-trihydroxy-3-thia-13-trans-7-homo-prostenoic acid |
| 258 | 64 | dl-erythro-9α,15,16-trihydroxy-3-thia-13-trans-7-homo-20-methyl-prostenoic acid |
| 259 | 65 | dl-erythro-9α,15,16-trihydroxy-3-thia-13-trans,17-trans-prostadienoic acid |
| 260 | 66 | dl-erythro-9α,15,16-trihydroxy-5-cis,13-trans-prostadienoic acid |
| 261 | 67 | dl-threo-9α,15,16-trihydroxy-5-cis,13-trans-prostadienoic acid |
| 262 | 68 | dl-erythro-9α,15,16-trihydroxy-5-cis,13-trans-20-nor-prostadienoic acid |
| 263 | 69 | dl-erythro-9α,15,16-trihydroxy-5-cis,13-trans-20-methyl-prostadienoic acid |
| 264 | 70 | dl-erythro-9α,15,16-trihydroxy-5-cis,13-trans-20-ethyl-prostadienoic acid |
| 265 | 71 | dl-erythro-9α,15,16-trihydroxy-5-cis,13-trans-19-methyl-prostadienoic acid |
| 266 | 72 | dl-erythro-9α,15,16-trihydroxy-5-cis,13-trans,17-trans-prostatrienoic acid |
| 267 | 73 | dl-erythro-9α,15,16-trihydroxy-2,3-methano-13-trans-prostenoic acid |
| 268 | 74 | dl-threo-9α,15,16-trihydroxy-2,3-methano-13-trans-prostenoic acid |
| 269 | 75 | dl-erythro-9α,15,16-trihydroxy-2,3-methano-13-trans-20-ethyl-prostenoic acid |
| 270 | 76 | dl-erythro-9α,15,16-trihydroxy-2,3-methano-13-trans,17-trans-prostadienoic acid |
| 271 | 77 | dl-erythro-9α,15,16-trihydroxy-13-trans-7-homo-prostenoic acid |
| 272 | 78 | dl-threo-9α,15,16-trihydroxy-13-trans-7-homo-prostenoic acid |
| 273 | 79 | dl-erythro-9α,15,16-trihydroxy-13-trans,17-trans-7-homo-prostadienoic acid |
| 274 | 80 | dl-erythro-9α,15,16-trihydroxy-13-trans-7a,7b-bishomo-prostenoic acid |
| 275 | 81 | dl-threo-9α,15,16-trihydroxy-13-trans-7a,7b-bishomo-prostenoic acid |
| 276 | 82 | dl-erythro-9α,15,16-trihydroxy-13-trans,17-trans-7a,7b-bishomo-prostadienoic acid |
| 277 | 120 | dl-erythro-9α,11α,15,16-tetrahydroxy-13-trans-prostenoic acid |
| 278 | 121 | dl-threo-9α,11α,15,16-tetrahydroxy-13-trans-prostenoic acid |
| 279 | 122 | dl-erythro-9α,11α,15,16-tetrahydroxy-13-trans-20-nor-prostenoic acid |
| 280 | 123 | dl-erythro-9α,11α,15,16-tetrahydroxy-20-methyl-prostenoic acid |
| 281 | 124 | dl-erythro-9α,11α,15,16-tetrahydroxy-20-ethyl-prostenoic acid |
| 282 | 125 | dl-erythro-9α,11α,15,16-tetrahydroxy-13-trans-19-methyl-prostenoic acid |
| 283 | 126 | dl-erythro-9α,11α,15,16-tetrahydroxy-13-trans,17-trans-prostadienoic acid |
| 284 | 127 | l-erythro-methyl-9α,11α,15,16-tetrahydroxy-13-trans-prostenoate |
| 285 | 128 | l-threo-methyl-9α,11α,15,16-tetrahydroxy-13-trans-prostenoate |
| 286 | 129 | l-erythro-methyl-9α,11α,15,16-tetrahydroxy-13-trans,17-trans-prostadienoate |
| 287 | 130 | d-erythro-methyl-9α,11α,15,16-tetrahydroxy-13-trans-prostenoate |
| 288 | 131 | d-threo-methyl-9α,11α,15,16-tetrahydroxy-13-trans-prostenoate |
| 289 | 132 | d-erythro-methyl-9α,11α,15,16-tetrahydroxy-13,17-trans-prostadienoate |
| 290 | 133 | dl-threo-9α,11α,15,16-tetrahydroxy-5-cis,13-trans-prostadienoic acid |
| 291 | 134 | dl-erythro-9α,11α,15,16-tetrahydroxy-5-cis,13-trans-20-nor-prostadienoic acid |
| 292 | 135 | dl-erythro-9α,11α,15,16-tetrahydroxy-5-cis,13-trans-20-methyl-prostadienoic acid |
| 293 | 136 | dl-erythro-9α,11α,15,16-tetrahydroxy-5-cis,13-trans-20-ethyl-prostadienoic acid |

TABLE X-continued

| Example | Starting 9-oxo-prostenoic acids or esters of Example | Product 9α-hydroxy substituted prostenoic acids or esters and the corresponding 9β-ol |
|---|---|---|
| 294 | 137 | dl-erythro-9,11α,15,16-tetrahydroxy-5-cis,13-trans-19-methyl-prostadienoic acid |
| 295 | 138 | dl-erythro-9,11,15,16-tetrahydroxy-5-cis,13-trans,17-trans-prostatrienoic acid |
| 296 | 139 | l-erythro-methyl-9α,11α,15,16-tetrahydroxy-5-cis,13-trans-prostadienoate |
| 297 | 140 | l-threo-methyl-9α,11α,15,16-tetrahydroxy-5-cis,13-trans-prostadienoate |
| 298 | 141 | l-erythro-methyl-9α,11α,15,16-tetrahydroxy-5-cis,13-trans,17-trans-prostatrienoate |
| 299 | 142 | dl-erythro-4(S)-methyl-9α,11α,15,16-tetrahydroxy-5-cis,13-trans-prostadienoic acid |
| 300 | 143 | dl-threo-(4R)-methyl-9α,11α,15,16-tetrahydroxy-5-cis,13-trans-prostadienoic acid |
| 301 | 144 | dl-erythro-(4R)-methyl-9α,11α,15,16-tetrahydroxy-5-cis,13-trans-prostadienoic acid |
| 302 | 145 | dl-erythro-(4R)-methyl-9α,11α,15,16-tetrahydroxy-5-cis,13-trans,17-trans-prostatrienoic acid |
| 303 | 146 | dl-erythro-4-propyl-9α,11α,15,16-tetrahydroxy-5-cis,13-trans-prostadienoic acid |
| 304 | 147 | dl-threo-4-propyl-9α,11α,15,16-tetrahydroxy-5-cis,13-trans-prostadienoic acid |
| 305 | 148 | dl-erythro-4-propyl-9α,11α,15,16-tetrahydroxy-5-cis,13-trans-20-ethyl-prostadienoic acid |
| 306 | 149 | dl-erythro-4-propyl-9α,11α,15,16-tetrahydroxy-5-cis,13,17-trans-prostatrienoic acid |
| 307 | 150 | dl-erythro-4-ethyl-9α,11α,15,16-tetrahydroxy-5-cis,13-trans-prostadienoic acid |
| 308 | 151 | dl-threo-4-ethyl-9α,11α,15,16-tetrahydroxy-5-cis,13-trans-prostadienoic acid |
| 309 | 152 | dl-erythro-4-ethyl-9α,11α,15,16-tetrahydroxy-5-cis,13-trans-20-methyl-prostadienoic acid |
| 310 | 153 | dl-erythro-4-ethyl-9α,11α,15,16-tetrahydroxy-5-cis,13,17-trans-prostatrienoic acid |
| 311 | 154 | dl-erythro-4-ethyl-9α,11α,15,16-tetrahydroxy-13-trans-7a,7b-bishomo-prostenoic acid |
| 312 | 155 | dl-threo-4-ethyl-9α,11α,15,16-tetrahydroxy-13-trans-7a,7b-bishomo-prostenoic acid |
| 313 | 156 | dl-erythro-9α,11α,15,16-tetrahydroxy-13,17-trans-7a,7b-bishomo-prostadienoic acid |
| 314 | 157 | dl-erythro-9-α,15-dihydroxy-16-methoxy-13-trans-prostenoic acid |
| 315 | 158 | dl-erythro-9-α,15-dihydroxy-16-ethoxy-13-trans-prostenoic acid |
| 316 | 159 | dl-erythro-9α,15-dihydroxy-16-methoxy-3-thia-13-trans-prostenoic acid |
| 317 | 160 | dl-erythro-9α,15-dihydroxy-16-ethoxy-3-thia-13-trans-prostenoic acid |
| 318 | 161 | dl-erythro-9α,15-dihydroxy-16-methoxy-3-oxa-13-trans-prostenoic acid |
| 319 | 162 | dl-erythro-9α,15-dihydroxy-16-methoxy-3-thia-13-trans-7-homo-prostenoic acid |
| 320 | 163 | dl-erythro-9α,15-dihydroxy-16-methoxy-5-cis,13-trans-prostadienoic acid |
| 321 | 164 | dl-erythro-9α,15-dihydroxy-16-ethoxy-5-cis,13-trans-prostadienoic acid |
| 322 | 165 | dl-erythro-9α,15-dihydroxy-16-methoxy-2,3-methano-13-trans-prostenoic acid |
| 323 | 166 | dl-erythro-9α,15-dihydroxy-16-methoxy-13-trans-7-homo-prostenoic acid |
| 324 | 167 | dl-erythro-9α,15-dihydroxy-16-methoxy-13-trans-7a,7b-bishomo-prostenoic acid |
| 325 | 168 | dl-erythro-9α,11,15-trihydroxy-16-methoxy-13-trans-prostenoic acid |
| 326 | 169 | dl-erythro-9α,11α,15-trihydroxy-13-ethoxy-13-trans-prostenoic acid |
| 327 | 170 | l-erythro-methyl-9α,11α,15-trihydroxy-16-methoxy-13-trans-7a,7b-bishomo-prostenoate |
| 328 | 171 | dl-erythro-9α,11α,15-trihydroxy-16-methoxy-13-trans-7a,7b-bishomo-prostenoate |
| 329 | 172 | dl-erythro-9α,11α,15-trihydroxy-16-methoxy-5-cis,13-trans-prostadienoic acid |
| 330 | 173 | dl-erythro-9α,11α,15-trihydroxy-16-ethoxy-5-cis,13-trans-prostadienoic acid |
| 331 | 174 | l-erythro-methyl-9α,11α,15-trihydroxy-16-methoxy-5-cis,13-trans-prostadienoic acid |
| 332 | 175 | dl-erythro-(4R)-methyl-9α,11α,15-trihydroxy-16-methoxy-5-cis,13-trans-prostadienoic acid |
| 333 | 176 | dl-erythro-4-propyl-9α,11α,15-trihydroxy-16-methoxy-5-cis,13-trans-prostadienoic acid |

TABLE X-continued

| Example | Starting 9-oxo-prostenoic acids or esters of Example | Product 9α-hydroxy substituted prostenoic acids or esters and the corresponding 9β-ol |
|---|---|---|
| 334 | 177 | dl-erythro-4-ethyl-9α,11α,15-trihydroxy-16-methoxy-5-cis,13-trans-prostadienoic acid |
| 335 | 178 | dl-erythro-9α,11α,15-trihydroxy-16-methoxy-13-trans-7a,7b-bishomo-prostenoic acid |

EXAMPLE 336

Preparation of dl-erythro-9α,11α,15,16-tetrahydroxy-5-cis,13-trans-prostadienoic acid and its 15-epimer To a −20° C. stirred solution of 300 mg. (0.813 mmol) of dl-erythro-9-oxo-11α,15,16-trihydroxy-5-cis,13-trans-prostadienoic acid (Example 34) in 12.0 ml. of dry tetrahydrofuran, under an argon atmosphere is added dropwise 4.40 ml. of a 0.5 M solution (2.20 mmol.) of lithium perhydro-9b-boraphenalylhydride in tetrahydrofuran. The mixture is stirred and allowed to warm to −5° C. over a one hour period. Then, 0.18 g. of sodium hydroxide in 3.0 ml. of water and 2.0 ml. of a 30% solution of hydrogen peroxide are added and stirring continued for 5 minutes. This mixture is poured into 10 ml. of water, extracted twice with 20 ml. each of ethyl ether, and acidified to pH one with 3.0 N hydrochloric acid. The water solution is saturated with sodium chloride, extracted twice with 25 ml. of ether, the combinated organic phases dried with magnesium sulfate, filtered, and evaporated affording 290 mg. of the subject 9α-hydroxy product, exclusively, as a white viscous oil. It may be purified by crystallization from ethyl ether at −30° C. By the same procedure, reduction of dl-erythro-9-oxo-11α,15-epi,16-trihydroxy-5-cis,13-trans-prostadienoic acid (Example 34) is productive of the corresponding 15-epimeric racemate, dl-erythro-9α,11α,15-epi,16-tetrahydroxy-5-cis,13-trans-prostadienoic acid.

EXAMPLES 337–361

Following the method of Example 336, treatment of the 9-oxo-prostenoic acids or esters, listed below, or their 15-epimeric racemates, with lithium perhydro-9b-boraphenalylhydride in tetrahydrofuran is productive of the corresponding 9α-hydroxy prostenoic acids or esters or their 15-epimeric racemates of Table XI. This reduction results exclusively in 9α-hydroxy isomers as shown in the table.

TABLE XI

| Example | Starting 9-oxo-prostenoic acids or esters or their 15-epimeric racemates of Example | Product 9α-hydroxy substituted prostenoic acids or esters or their 15-epimers |
|---|---|---|
| 337 | 23 | dl-erythro-9α,15,16-trihydroxy-13-trans-prostenoic acid |
| 338 | 51 | dl-erythro-9α,15,16-trihydroxy-13-trans-19-methyl-prostenoic acid |
| 339 | 53 | dl-erythro-9α,15,16-trihydroxy-3-thia-13-trans-prostenoic acid |
| 340 | 58 | dl-erythro-9α,15,16-trihydroxy-3-oxa-13-trans-prostenoic acid |
| 341 | 67 | dl-threo-9α,15,16-trihydroxy-5-cis,13-trans-prostadienoic acid |
| 342 | 73 | dl-erythro-9α,15,16-trihydroxy-2,3-methano-13-trans-prostenoic acid |
| 343 | 157 | dl-erythro-9α,15-dihydroxy-16-methoxy-13-trans-prostenoic acid |
| 344 | 160 | dl-erythro-9α,15-dihydroxy-16-ethoxy-3-thia-13-trans-prostenoic acid |
| 345 | 161 | dl-erythro-9α,15-dihydroxy-16-methoxy-3-oxa-13-trans-prostenoic acid |
| 346 | 164 | dl-erythro-9α,15-dihydroxy-16-ethoxy-5-cis,13-trans-prostadienoic acid |
| 347 | 166 | dl-erythro-9α,15-dihydroxy-16-methoxy-13-trans-7-homo-prostenoic acid |
| 348 | 121 | dl-threo-9α,11α,15,16-tetrahydroxy-13-trans-prostenoic acid |
| 349 | 127 | l-erythro-methyl-9α,11α,15,16-tetrahydroxy-13-trans-prostenoate |
| 350 | 128 | l-threo-methyl-9α,11α,15,16-tetrahydroxy-13-trans-prostenoate |
| 351 | 129 | l-erythro-methyl-9α,11α,15,16-tetrahydroxy-13-trans,17-trans-prostadienoate |
| 352 | 130 | d-erythro-methyl-9α,11α,15,16-tetrahydroxy-13-trans-prostenoate |
| 353 | 131 | d-threo-methyl-9α,11α,15,16-tetrahydroxy-13-trans-prostenoate |
| 354 | 133 | dl-threo-9α,11α,15,16-tetrahydroxy-5-cis,13-trans-prostadienoic acid |
| 355 | 142 | dl-erythro-(4R)-methyl-9α,11α,15,16-tetrahydroxy-5-cis,13-trans-prostadienoic acid |
| 356 | 154 | dl-erythro-9α,11α,15,16-tetrahydroxy-13-trans-7a,7b-bishomo-prostenoic acid |
| 357 | 168 | dl-erythro-9α,11α,15-trihydroxy-16-methoxy-13-trans-prostenoic acid |
| 358 | 170 | l-erythro-methyl-9α,11α,15-trihydroxy-16-methoxy-13-trans-prostenoate |
| 359 | 171 | d-erythro-methyl-9α,11α,15-trihydroxy-16-methoxy-13-trans-prostenoate |
| 360 | 172 | dl-erythro-9α,11α,15-trihydroxy-16-methoxy-5-cis,13-trans-prostadienoic acid |
| 361 | 174 | l-erythro-methyl-9α,11α,15-trihydroxy-16-methoxy-5-cis,13-trans-prostadienoate |

EXAMPLE 362

Preparation of dl-erythro-9-oxo-13,14-dihydro-15,16-dihydroxy-prostanoic acid and its 15-epimeric racemate A solution of 400 mg. (1.13 mmol.) of dl-erythro-9-oxo-15,16-dihydroxy-13-trans-prostenoic acid (Example 23) in 25 ml. of ethyl acetate is hydrogenated at 20 p.s.i. of hydrogen pressure, at ambient temperature, over 150 mg. of a 5% rhodium on carbon catalyst. The mixture is shaken vigorously for 15 hours under these conditions. It is then filtered through a 5.0 cm pad of Celite and evaporated under vacuum to give 380 mg. of the subject product as an oil. Using the same procedure, hydrogenation of dl-erythro-9-oxo-15-epi,16-dihydroxy-13-trans-prostenoic acid is productive of the 15-epimeric subject product dl-erythro-9-oxo-13,14-dihydro-15-epi,16-dihydroxy-prostanoic acid.

EXAMPLES 363–384

By the method of Example 362, hydrogenation of the 13-trans-prostenoic acids or esters of Table XII, below, or their 15-epimeric racemates with 5% rhodium-on-carbon in ethyl acetate, is productive of the corresponding 13,14-dihydro prostanoic acids or esters or their 15-epimers listed in the Table.

acid in 2.0 ml. of ethyl ether, at 0° C. in an ice bath, is added dropwise with stirring, a solution of diazomethane in ethyl ether until an excess is added, as indicated by the yellow color of the mixture produced, stirring is continued at 0° C. for one hour, excess diazomethane is destroyed by dropwise addition of acetic acid, and the ether solvent is removed by evaporation under vacuum. The product is then evaporated three times with 10 ml. each of benzene to remove traces of acetic acid, under high vacuum at 40° C., to yield the methylated subject compound as a yellow oil. Following the same procedure with the 15-epimeric racemic acid is productive of the dl-erythro-methyl-9-oxo-11α,15-epi,16-trihydroxy-5-cis,13-trans-prostadienoate subject product.

EXAMPLES 386–408

Treatment of the various 9-oxo-15,16-dihydroxy or 15-hydroxy-16-alkoxy or 11α,15,16-trihydroxy or 11α,15-dihydroxy-16-alkoxy-13-trans-prostenoic acids Table XII

| Example | Starting 9-oxo-13-trans-prostenoic acids or esters or their 15-epimeric racemates of Example | Product 9-oxo-13,14-dihydro-15,16-dihydroxy or 11,15,16-trihydroxy or 15-hydroxy-16-alkoxy or 11,15-dihydroxy-16-alkoxy-prostanoic acids and esters or their 15-epimers |
|---|---|---|
| 363 | 47 | dl-threo-9-oxo-13,14-dihydro-15,16-dihydroxy-prostanoic acid |
| 364 | 49 | dl-erythro-9-oxo-13,14-dihydro-15,16-dihydroxy-20-methyl-prostanoic acid |
| 365 | 58 | dl-erythro-9-oxo-13,14-dihydro-15,16-dihydroxy-3-oxa-prostanoic acid |
| 366 | 73 | dl-erythro-9-oxo-13,14-dihydro-15,16-dihydroxy-2,3-methano-prostanoic acid |
| 367 | 80 | dl-erythro-9-oxo-13,14-dihydro-15,16-dihydroxy-7a,7b-bishomo-prostanoic acid |
| 368 | 157 | dl-erythro-9-oxo-13,14-dihydro-15-hydroxy-16-methoxy-prostanoic acid |
| 369 | 158 | dl-erythro-9-oxo-13,14-dihydro-15-hydroxy-16-ethoxy-prostanoic acid |
| 370 | 166 | dl-erythro-9-oxo-13,14-dihydro-15-hydroxy-16-methoxy-7-homo-prostanoic acid |
| 371 | 120 | dl-erythro-9-oxo-13,14-dihydro-11α,15,16-trihydroxy-prostanoic acid |
| 372 | 121 | dl-threo-9-oxo-13,14-dihydro-11α,15,16-trihydroxy-prostanoic acid |
| 373 | 122 | dl-erythro-9-oxo-13,14-dihydro-11α,15,16-trihydroxy-20-nor-prostanoic acid |
| 374 | 125 | dl-erythro-9-oxo-13,14-dihydro-11α,15,16-trihydroxy-19-methyl-prostanoic acid |
| 375 | 127 | l-erythro-methyl-9-oxo-13,14-dihydro-11α,15,16-trihydroxy-prostanoate |
| 376 | 128 | l-threo-methyl-9-oxo-13,14-dihydro-11α,15,16-trihydroxy-prostanoate |
| 377 | 130 | d-erythro-methyl-9-oxo-13,14-dihydro-11α,15,16-trihydroxy-prostanoate |
| 378 | 131 | d-threo-methyl-9-oxo-13,14-dihydro-11α,15,16-trihydroxy-prostanoate |
| 379 | 154 | dl-erythro-9-oxo-13,14-dihydro-11α,15,16-trihydroxy-7a,7b-bishomo-prostanoic acid |
| 380 | 155 | dl-threo-9-oxo-13,14-dihydro-11α,15,16-trihydroxy-7a,7b-bishomo-prostanoic acid |
| 381 | 168 | dl-erythro-9-oxo-13,14-dihydro-11α,15-dihydroxy-16-methoxy-prostanoic acid |
| 382 | 169 | dl-erythro-9-oxo-13,14-dihydro-11α,15-dihydroxy-16-ethoxy-prostanoic acid |
| 383 | 170 | dl-erythro-methyl-9-oxo-13,14-dihydro-11α,15-dihydroxy-16-methoxy-prostanoate |
| 384 | 178 | dl-erythro-9-oxo-13,14-dihydro-11α,15-dihydroxy-16-methoxy-7a,7b-bishomo-prostanoic acid |

EXAMPLE 385

Preparation of dl-erythro-methyl-9-oxo-11α,15,16-trihydroxy-5-cis,13-trans-prostadienoate and dl-erythro-methyl-9-oxo-11α,15-epi,16-trihydroxy-5-cis,13-trans-prostadienoate To a solution of 100 mg. (0.272 mmol of dl-erythro-9-oxo-11α,15,16-trihydroxy-5-cis,13-trans-prostadienoic of Table XIII or their 15-epimers with ethereal solutions of the diazoalkanes, also listed, by the procedure of Example 385, is productive of the corresponding alkyl prostenoate ester derivatives of the table, below.

Table XIII

| Example | diazoalkane | Starting 9-oxo-13-trans-prostenoic acids or esters or their 15-epimers of Example | Product alkyl 9-oxo-13-trans-prostenoates or their 15-epimeric racemates |
|---|---|---|---|
| 386 | diazomethane | 23 | dl-erythro-methyl-9-oxo-15,16-dihydroxy-13-trans-prostenoate |

Table XIII-continued

| Example | diazoalkane | Starting 9-oxo-13-trans-prostenoic acids or esters or their 15-epimers of Example | Product alkyl 9-oxo-13-trans-prostenoates or their 15-epimeric racemates |
|---|---|---|---|
| 387 | diazobutane | 47 | dl-threo-butyl-9-oxo-15,16-dihydroxy-13-trans-prostenoate |
| 388 | diazohexane | 53 | dl-erythro-hexyl-9-oxo-15,16-dihydroxy-3-thia-13-trans-prostenoate |
| 389 | diazononane | 58 | dl-erythro-nonyl-9-oxo-15,16-dihydroxy-3-oxa-13-trans-prostenoate |
| 390 | diazomethane | 67 | dl-threo-methyl-9-oxo-15,16-dihydroxy-5-cis,13-trans-prostadienoate |
| 391 | diazohexane | 72 | dl-erythro-hexyl-9-oxo-15,16-dihydroxy-5-cis,13-trans,17-trans-prostatrienoate |
| 392 | diazononane | 73 | dl-erythro-nonyl-9-oxo-15,16-dihydroxy-2,3-methano-13-trans-prostenoate |
| 393 | diazobutane | 81 | dl-threo-butyl-9-oxo-15,16-dihydroxy-13-trans-7a,7b-bishomo-prostenoate |
| 394 | diazomethane | 157 | dl-erythro-methyl-9-oxo-15-hydroxy-16-methoxy-13-trans-prostenoate |
| 395 | diazobutane | 158 | dl-erythro-butyl-9-oxo-15-hydroxy-16-ethoxy-13-trans-prostenoate |
| 396 | diazobutane | 158 | dl-erythro-butyl-9-oxo-15-hydroxy-16-ethoxy-13-trans-prostenoate |
| 397 | diazononane | 120 | dl-erythro-nonyl-9-oxo-11$\alpha$,15,16-trihydroxy-13-trans-prostenoate |
| 398 | diazomethane | 121 | dl-threo-methyl-9-oxo-11$\alpha$,15,16-trihydroxy-13-trans-prostenoate |
| 399 | diazohexane | 124 | dl-erythro-hexyl-9-oxo-11$\alpha$,15,16-trihydroxy-13-trans-20-ethyl-prostenoate |
| 400 | diazobutane | 125 | dl-erythro-butyl-9-oxo-11$\alpha$,15,16-trihydroxy-13-trans-19-methyl-prostenoate |
| 401 | diazononane | 133 | dl-threo-nonyl-9-oxo-11$\alpha$,15,16-trihydroxy-5-cis,13-trans-prostadienoate |
| 402 | diazomethane | 134 | dl-erythro-methyl-9-oxo-11$\alpha$,15,16-trihydroxy-5-cis,13-trans-20-nor-prostadienoate |
| 403 | diazobutane | 142 | dl-erythro-butyl-4(R)-methyl-9-oxo-11$\alpha$,15,16-trihydroxy-5-cis,13,-trans-prostadienoate |
| 404 | diazohexane | 147 | dl-threo-hexyl-4-propyl-9-oxo-11$\alpha$,15,16-trihydroxy-5-cis,13-trans-prostadienoate |
| 405 | diazomethane | 152 | dl-erythro-methyl-9-oxo-11$\alpha$,15,16-trihydroxy-5-cis,13-trans-20-methyl-prostadienoate |
| 406 | diazomethane | 168 | dl-erythro-methyl-9-oxo-11$\alpha$,15-dihydroxy-16-methoxy-13-trans-prostenoate |
| 407 | diazohexane | 173 | dl-erythro-hexyl-9-oxo-11$\alpha$,15-dihydroxy-16-ethoxy-5-cis,13-trans-prostadienoate |
| 408 | diazononane | 177 | dl-erythro-4-ethyl-nonyl-9-oxo-11$\alpha$,15-dihydroxy-16-methoxy-5-cis,13-trans-prostenoate |

EXAMPLE 409

Preparation of dl-threo-3,4-dihydroxy-1-octyne

A solution of 19 g. of crude dl-threo-3,4-dihydroxy-1-octyne (Example 12), containing 15% of the erythro isomer (Example 13), in 20 ml. of ethyl acetate and 80 ml. of hexane is applied to a 2¾"×55" dry column of silica gel and eluted with 50 liters of a 1:4 mixture of ethyl acetate in hexane. The column is cut up into 1.0" sections, and each fraction, dissolved in ethyl ether, is identified by the use of a thin layer chromatogram of silica gel, eluting with the above solvent system. Each fraction containing the less polar threo isomer is combined, filtered from the silica gel, evaporated under vacuum, with 200 ml. of benzene, and under high vacuum leaving 14.0 g. of the chromatographically pure subject compounds as an oil.

EXAMPLE 410

Preparation of dl-threo-3,4-bis-trimethylsilyloxy-1-octyne

Following the procedure of Example 33, 14.0 g. of dl-threo-3,4-dihydroxy-1-octyne (Example 409) is treated with timethylchlorosilane and imidazole in dimethylformamide to give 15.3 g. (55%) of the subject product as a light yellow oil.

EXAMPLE 411

Preparation of dl-threo-1-iodo-3,4-bis-trimethylsilyloxy-trans-1-octene

Using the procedure of Example 7, 15.3 g. of dl-threo-3,4-bis-trimethylsilyloxy-1-octyne (Example 410) is treated successively with a solution of diisamylborane in tetrahydrofuran, trimethylamine oxide, and solutions of sodium hydroxide, and iodine in tetrahydrofuran. After workup, the crude vinyl iodide is stirred for one hour at ambient temperature with 90 ml. of acetic acid, 30 ml. of tetrahydrofuran and 30 ml. of water. The solution is then evaporated under high vacuum at 40° C. The crude threo-vinyl iodide diol obtained is then chromatographed on a 3"×40" dry column of silica gel and eluted with chloroform to give 10.5 g. of purified product. This is treated again with trimethylchlorosilane and imidazole in dimethylformamide, as in Example 33, to give the subject product which is purified on a 2¾×36" dry column of silica gel, and eluted with hexane, to yield 11.0 g. (50%) of a yellow oil.

EXAMPLE 412

Preparation of 2-(7-carbethoxy-6-thiaheptyl)-1-methoximino-2-cyclopentene

To a stirred mixture of 24.2 g. (0.577 mols) of sodium hydride (57.2% in mineral oil) in 350 ml. of dimethoxyethane, under nitrogen, is added slowly 69 g. (0.575 mols) of ethyl 2-mercaptoacetate. The reaction mixture is stirred at room temperature for one hour and then a solution of 100 g. (0.363 mols) of 2-(5-methanesulfonyloxypentyl)-1-methoximino-2-cyclopentene (U.S. Pat. No. 3,836,581) in 300 ml. of dimethoxyethane is added dropwise and stirred at room temperature for 18 hours.

EXAMPLE 413

Preparation of 2-(7-carboxy-6-thiaheptyl)-2-cyclopentenone

A solution of 100 g. (0.333 mols) of 2-(7-carbethoxy-6-thiaheptyl)-1-methoximino-2-cyclopentene in 1800 ml. of acetone and 700 ml. of 2 N hydrochloric acid is refluxed for 5 hours. The mixture is cooled, the solvent is evaporated and the residue partitioned between water and diethyl ether. The organic phase is washed with water and saline, dried (MgSO₄) and evaporated to give 94 g. of subject product as a yellow oil. The solution is heated at reflux for one hour, cooled and poured into cold dilute hydrochloric acid and then extracted with ether. The combined ether extracts are washed with saline, dried over magnesium sulfate and evaporated to give 105 g. of subject product as a yellow oil.

EXAMPLE 414

Preparation of 2-(7-carbethoxy-6-thiaheptyl)-2-cyclopentenone

A mixture of 74 g. (0.306 mols) of 2-(7-carboxy-6-thiaheptyl)-2-cyclopentenone, 1200 ml. of ethanol and 1 g. p-toluenesulfonic acid is stirred and refluxed for 18 hours. The resulting solution is concentrated and the residue is dissolved in ether. The organic phase is washed with water, sodium bicarbonate solution and saline, dried (MgSO₄) and evaporated. The residue is distilled to give a light yellow oil, n.p. 147°–150° C. (0.07 Torr).

EXAMPLE 415

2-(6-Carbethoxy-5,6-methanohexyl)-cyclopent-2-en-1-one and 2-(6-Carboxy-5,6-methanohexyl)-cyclopent-2-en-1-one A mixture of 5.2 g. of dl-2(6-carbethoxy-5,6-methanohexyl)-3-methoximino-1-cyclopentene. (Example 4) and 38 ml. of 2 N hydrochloric acid in 95 ml. of acetone is refluxed for 2 hours, cooled, and partially evaporated in vacuo. The residue is partitioned between water and hexane. The organic phase is washed with water, dilute sodium bicarbonate solution, water, and brine, dried (MgSO₄), and evaporated in vacuo to yield crude 2-(6-carbethoxy-5,6-methanohexyl)-cyclopent-2-en-1-one which is purified by column-chromatography upon Florisil ® and with a hexane-methylene chloride gradient as eluting solvent. The sodium bicarbonate washings are acidified with hydrochloric acid and extracted with methylene chloride. The organic phase is washed with water and saturated brine, dried (MgSO₄), and evaporated in vacuo to yield 2-(6-carboxy-5,6-methanohexyl)cyclopent-2-en-1-one.

EXAMPLES 416–419

By the method of Example 3, reaction of 1-trimethylsilyl-3-tetrahydropyranyloxy-1-propene with n-butyllithium and subsequent treatment with the methyl ketones listed in Table XIV provides 1-trimethylsilyl-3-tetrahydropyranyloxy-4-alkyl-4-hydroxy-1-alkynes of the Table.

TABLE XIV

| EXAMPLE | STARTING METHYL KETONE | PRODUCT 1-trimethylsilyl-3-tetrahydropyranyloxy-4-alkyl-4-hydroxy-1-trimethylsilyl-1-alkyne |
|---------|------------------------|---------------------------------------------------------------------------------------------|
| 416     | 2-pentanone            | 1-trimethylsilyl-3-tetrahydropyranyloxy-4-methyl-4-hydroxy-1-octyne |
| 417     | 2-hexanone             | 1-trimethylsilyl-3-tetrahydropyranyloxy-4-methyl-4-hydroxy-1-nonyne |
| 418     | 2-heptanone            | 1-trimethylsilyl-3-tetrahydropyranyloxy-4-methyl-4-hydroxy-1-decyne |
| 419     | 2-butanone             | 1-trimethylsilyl-3-tetrahydropyranyloxy-4-methyl-4-hydroxy-1-heptyne |

EXAMPLES 420–423

By the procedure of Example 3, reaction of 1-trimethylsilyl-3-tetrahydropyranyloxy-1-butyne with n-butyllithium and subsequent treatment with the aldehydes listed in Table XV provides 1-trimethylsilyl-3-methyl-3-tetrahydropyranyloxy-4-hydroxy-1-alkynes of the Table.

TABLE XV

| EXAMPLE | STARTING ALDEHYDE | PRODUCT 1-trimethylsilyl-3-tetrahydropyranyloxy-3-alkyl-4-hydroxy-1-trimethylsilyl-1-alkyne |
|---------|-------------------|---------------------------------------------------------------------------------------------|
| 420     | butanal           | 1-trimethylsilyl-3-tetrahydropyranyloxy-3-methyl-4-hydroxy-1-octyne |
| 421     | pentanal          | 1-trimethylsilyl-3-tetrahydropyranyloxy-3-methyl-4-hydroxy-1-nonyne |
| 422     | hexanal           | 1-trimethylsilyl-3-tetrahydropyranyloxy-3-methyl-4-hydroxy-1-decyne |
| 423     | propanal          | 1-trimethylsilyl-3-tetrahydropyranyloxy-3-methyl-4-hydroxy-1-heptyne |

EXAMPLES 424–431

Hydrolysis of the 3-tetrahydropyranyloxy group of the alkynes listed in Table XVI by the method of Example 4 followed by removal of the terminal TMS group by the procedure of Example 6 followed by protection of the two hydroxyls as trimethylsilyl ethers by the procedure of Example 33 followed by treatment successively with a solution of diisamylborane in tetrahydrofuran, trimethylamine oxide, and solutions of sodium hydroxide and iodine in tetrahydrofuran by the procedure of Example 7, provides, after work-up and treatment with acetic acid, THF and water by the method of Example 411, the crude vinyl iodide diols of the Table.

These crude diols are purified by dry column chromatography.

TABLE XVI

| EXAMPLE | STARTING 1-ALKYNE | PRODUCT 1-iodo-3,4-dihydroxy-trans-1-alkene |
| --- | --- | --- |
| 424 | 416 | 1-iodo-3,4-dihydroxy-4-methyl-trans-1-octene |
| 425 | 417 | 1-iodo-3,4-dihydroxy-4-methyl-trans-1-nonene |
| 426 | 418 | 1-iodo-3,4-dihydroxy-4-methyl-trans-1-decene |
| 427 | 419 | 1-iodo-3,4-dihydroxy-4-methyl-trans-1-heptene |
| 428 | 416 | 1-iodo-3,4-dihydroxy-3-methyl-trans-1-octene |
| 429 | 417 | 1-iodo-3,4-dihydroxy-3-methyl-trans-1-nonene |
| 430 | 418 | 1-iodo-3,4-dihydroxy-3-methyl-trans-1-decene |
| 431 | 419 | 1-iodo-3,4-dihydroxy-3-methyl-trans-1-heptene |

EXAMPLES 432–439

Treatment of the vinyl iodide diols of Table XVII with trimethylchlorosilane and imidazole in dimethylformamide as in Example 33 provides, after column chromatography, the bistrimethylsiloxy vinyl iodides of the Table.

TABLE XVII

| EX. | STARTING DIOL | PRODUCT bis TMS ether |
| --- | --- | --- |
| 432 | 424 | 1-iodo-3,4-bistrimethylsilyloxy-4-methyl-trans-1-octene |
| 433 | 425 | 1-iodo-3,4-bistrimethylsilyloxy-4-methyl-trans-1-nonene |
| 434 | 426 | 1-iodo-3,4-bistrimethylsilyloxy-4-methyl-trans-1-decene |
| 435 | 427 | 1-iodo-3,4-bistrimethylsilyloxy-4-methyl-trans-1-heptene |
| 436 | 428 | 1-iodo-3,4-bistrimethylsilyloxy-3-methyl-trans-1-octene |
| 437 | 429 | 1-iodo-3,4-bistrimethylsilyloxy-3-methyl-trans-1-nonene |
| 438 | 430 | 1-iodo-3,4-bistrimethylsilyloxy-3-methyl-trans-1-decene |
| 439 | 431 | 1-iodo-3,4-bistrimethylsilyloxy-3-methyl-trans-1-heptene |

EXAMPLES 440–455

Treatment of the cyclopentenones listed in Tabe XVIII below with the pentynyl litheo cuprate prepared from the 1-iodo-trans-1-alkenyl derivative listed in Table XVIII, by the procedure of Example 14, provides the corresponding 9-oxo-11-tetrahydropyranyloxy-15,16-bistrimethylsilyloxy-3 or 4-methyl-13-trans prostanoic acid or ester which is subjected to hydrolysis by the procedure of Example 10 to provide the 11α,15α,16-trihydroxy prostaglandins and corresponding 15-epimers of the Table.

TABLE XVIII

| EXAMPLE | STARTING CYCLOPENTENONE | STARTING VINYL IODIDES | PRODUCT PROSTAGLANDIN |
| --- | --- | --- | --- |
| 440 | 2(6-carbotetrahydropyranyloxyhexyl)-4-tetrahydropyranyloxy-cyclopent-2-en-1-one | 424 | 9-oxo-11α,15α,16-trihydroxy-16-methyl-13-trans-prostenoic acid and the 15-epimer |
| 441 | same | 425 | 9-oxo-11α,15α,16-trihydroxy-16,20-dimethyl-13-trans-prostenoic acid and the 15-epimer |
| 442 | same | 426 | 9-oxo-11α,15α,16-trihydroxy-16-methyl-20-ethyl-13-trans-prostenoic acid and the 15-epimer |
| 443 | same | 427 | 9-oxo-11α,15α,16-trihydroxy-16-methyl-20-nor-13-trans-prostenoic acid and the 15-epimer |
| 444 | 2(6-carbomethoxy-hexyl)-4(R)-tetrahydropyranyloxycyclopent-2-en-1-one | 424 | Nat. methyl-9-oxo-11α,15α,16-trihydroxy-16-methyl-13-trans-prostenoate and the 15-epimer |
| 445 | same | 425 | Nat. Methyl-9-oxo-11α,15α,16-trihydroxy-16-20-dimethyl-13-trans-prostenoate and the 15-epimer |
| 446 | same | 426 | Nat. Methyl-9-oxo-11α,15α,16-trihydroxy-16-methyl-20-ethyl-13-trans-prostenoate and the 15-epimer |
| 447 | same | 427 | Nat. Methyl-9-oxo-11α,15α,16-trihydroxy-16-methyl-20-nor-13-trans-prostenoate and the 15-epimer |
| 448 | 2(6-carbotetrahydropyranyloxyhexyl)-4-tetrahydropyranyloxycyclopent-2-en-1-one | 428 | 9-oxo-11α,15α,16-trihydroxy-15-methyl-13-trans-prostenoic acid and the 15-epimer |
| 449 | same | 429 | 9-oxo-11α,15α,16-tridydroxy-15,20-dimethyl-13-trans-prostenoic acid and the 15-epimer |
| 450 | same | 430 | 9-oxo-11α,15α,16-trihydroxy-15-methyl-20-ethyl-13-trans-prostenoic acid and the 15-epimer |
| 451 | same | 431 | 9-oxo-11α,15α,16-trihydroxy- |

TABLE XVIII-continued

| EXAMPLE | STARTING CYCLOPENTENONE | STARTING VINYL IODIDES | PRODUCT PROSTAGLANDIN |
|---------|-------------------------|------------------------|------------------------|
| 452 | 2(6-carbomethyoxyhexyl)-4(R)-tetrahydropyranyloxy-cyclopent-2-en-1-one | 428 | 15-methyl-20-nor-13-trans-prostenoic acid and the 15-epimer Nat. Methyl-9-oxo-11α,15α,16-trihydroxy-15-methyl-13-trans-prostenoate and the 15-epimer |
| 453 | same | 429 | Nat. Methyl-9-oxo-11α,15α,16-trihydroxy-15,20-dimethyl-13-trans-prostenoate and the 15-epimer |
| 454 | same | 430 | Nat. Methyl-9-oxo-11α,15α,16-trihydroxy-15-methyl-20-ethyl-13-trans-prostenoate and the 15-epimer |
| 455 | same | 431 | Nat. Methyl-9-oxo-11α,15α,16-trihydroxy-15-methyl-20-nor-13-trans-prostenoate and the 15-epimer |

EXAMPLE 456

Treatment of the acids of Examples 440-443 and 448-451 with excess diazomethane or diazoethane will provide the corresponding methyl and ethyl esters, respectively.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed invention are considered to be within the purview and scope of this invention and the following claims.

I claim:

1. An optically active compound of the formula:

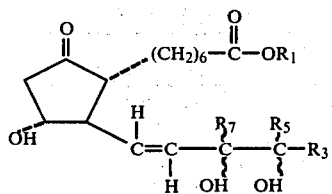

wherein $R_1$ is selected from the group consisting of hydroxy and alkoxy ($C_1$ to $C_3$); $R_3$ is alkyl ($C_3$ to $C_6$); $R_5$ is selected from the group consisting of hydrogen and alkyl ($C_1$ to $C_3$); and $R_7$ is selected from the group consisting of hydrogen and alkyl ($C_1$ to $C_3$); and the pharmacologically acceptable cationic salts thereof when $R_1$ is hydroxy.

2. The optical isomer according to claim 1 wherein $R_1$ is hydroxy, and $R_3$ is n-butyl; l-erythro-9-oxo-11α,15,16-trihydroxy-13-trans-prostenoic acid.

3. The racemic mixture according to claim 1 wherein $R_1$ is hydroxy, and $R_3$ is n-butyl; dl-erythro-9-oxo-11α,15,16-trihydroxy-13-trans-prostenoic acid.

4. The optical isomer according to claim 1 wherein $R_1$ is hydroxy, and $R_3$ is n-butyl; l-threo-9-oxo-11α,15,16-trihydroxy-13-trans-prostenoic acid.

5. The racemic mixture according to claim 1 wherein $R_1$ is hydroxy, and $R_3$ is n-butyl; dl-threo-9-oxo-11α,15,16-trihydroxy-13-trans-prostenoic acid.

6. The optical isomer that is l-erythro-9-oxo-11α,15-dihydroxy-16-methoxy-13-trans-prostenoic acid.

7. The racemic mixture that is dl-erythro-9-oxo-11α,15-dihydroxy-16-methoxy-13-trans-prostenoic acid.

* * * * *